US012383617B2

(12) United States Patent
Hubbell et al.

(10) Patent No.: US 12,383,617 B2
(45) Date of Patent: Aug. 12, 2025

(54) COMPOSITIONS AND METHODS CONCERNING IMMUNE TOLERANCE

(71) Applicants: The University of Chicago, Chicago, IL (US); Anokion SA, Ecublens (CH)

(72) Inventors: Jeffrey A. Hubbell, Chicago, IL (US); David Scott Wilson, Chicago, IL (US); Kym Brünggel, Chicago, IL (US); Kristen Marie Lorentz, Ecublens (CH)

(73) Assignees: The University of Chicago, Chicago, IL (US); Anokion SA, Ecublens (CH)

( * ) Notice: Subject to any disclaimer, the term of this patent is extended or adjusted under 35 U.S.C. 154(b) by 951 days.

(21) Appl. No.: 17/250,015

(22) PCT Filed: May 9, 2019

(86) PCT No.: PCT/US2019/031440
§ 371 (c)(1),
(2) Date: Nov. 3, 2020

(87) PCT Pub. No.: WO2019/217628
PCT Pub. Date: Nov. 14, 2019

(65) Prior Publication Data
US 2021/0244812 A1    Aug. 12, 2021

Related U.S. Application Data

(60) Provisional application No. 62/669,044, filed on May 9, 2018.

(51) Int. Cl.
| | |
|---|---|
| A61K 39/385 | (2006.01) |
| A61K 39/00 | (2006.01) |
| A61K 47/54 | (2017.01) |
| A61K 47/60 | (2017.01) |
| A61P 37/06 | (2006.01) |
| C07D 249/16 | (2006.01) |
| C08F 220/58 | (2006.01) |
| C08G 65/332 | (2006.01) |
| C08G 65/334 | (2006.01) |
| C08G 81/02 | (2006.01) |

(52) U.S. Cl.
CPC ........ *A61K 39/385* (2013.01); *A61K 39/0008* (2013.01); *A61K 39/001154* (2018.08); *A61K 39/001158* (2018.08); *A61K 39/4611* (2023.05); *A61K 39/4644* (2023.05); *A61K 47/549* (2017.08); *A61K 47/60* (2017.08); *A61P 37/06* (2018.01); *C07D 249/16* (2013.01); *C08F 220/58* (2013.01); *C08G 65/332* (2013.01); *C08G 65/3344* (2013.01); *C08G 81/025* (2013.01); *A61K 2039/6087* (2013.01); *A61K 2039/6093* (2013.01); *A61K 2239/38* (2023.05)

(58) Field of Classification Search
CPC .................................................. A61K 39/385
See application file for complete search history.

(56) References Cited

U.S. PATENT DOCUMENTS

| | | |
|---|---|---|
| 4,671,958 A | 6/1987 | Rodwell et al. |
| 4,741,900 A | 5/1988 | Alvarez et al. |
| 4,859,449 A | 8/1989 | Mattes |
| 4,867,973 A | 9/1989 | Goers et al. |
| 4,950,738 A | 8/1990 | King et al. |
| 5,086,002 A | 2/1992 | Hillyard et al. |
| 5,140,104 A | 8/1992 | Coughlin et al. |
| 5,156,840 A | 10/1992 | Goers et al. |
| 5,162,512 A | 11/1992 | King et al. |
| 5,227,165 A | 7/1993 | Domb et al. |
| 5,227,293 A | 7/1993 | Stengelin et al. |
| 5,346,696 A | 9/1994 | Kim et al. |
| 5,358,857 A | 10/1994 | Stengelin et al. |
| 5,470,570 A | 11/1995 | Taylor et al. |
| 5,487,890 A | 1/1996 | Taylor et al. |
| 5,681,571 A | 10/1997 | Holmgren et al. |
| 5,698,679 A | 12/1997 | Nemazee et al. |
| 5,718,915 A | 2/1998 | Virtanen et al. |
| 5,879,679 A | 3/1999 | Taylor et al. |
| 5,885,808 A | 3/1999 | Spooner et al. |
| 5,886,143 A | 3/1999 | Theodore et al. |
| 5,948,639 A | 9/1999 | Gimeno et al. |
| 5,985,826 A | 11/1999 | Theodore et al. |
| 5,994,104 A | 11/1999 | Anderson et al. |
| 5,997,861 A | 12/1999 | Virtanen et al. |
| 6,022,564 A | 2/2000 | Takechi et al. |
| 6,090,925 A | 7/2000 | Woiszwillo et al. |
| 6,120,770 A | 9/2000 | Adams et al. |

(Continued)

FOREIGN PATENT DOCUMENTS

| | | |
|---|---|---|
| CN | 1289256 | 3/2001 |
| CN | 1756560 | 4/2006 |

(Continued)

OTHER PUBLICATIONS

"EPFL School of Life Sciences—Annual Report SV 2011," 156 Pages (Dec. 31, 2011 ).
"Integer", Meriam-Webster, available online at https://www.merriam-webster.com/dictionary/integer, 12 pages (2019) (Year: 2019).
"SubName: Full=Phosphate ABC Transporter, Inner Membrane Subunit PstC;", XP002717162, Retrieved From EBI Accession No. UNIPROT:C7QKI6, Database Accession No. C7QKI6 (Oct. 13, 2009).
"SubName: Full=Putative Integron Gene Cassette Protein; Flags: Fragment;", XP002717159, Retrieved From EBI Accession No. UNIPROT:B0BIT0, Database Accession No. B0BIT0 (Feb. 26, 2008).

(Continued)

*Primary Examiner* — Paul V Ward
(74) *Attorney, Agent, or Firm* — Norton Rose Fulbright US LLP

(57) ABSTRACT

The present disclosure provides compositions comprising mannose-fused antigens to target mannose receptors. The compositions may be used to prevent immunity or reduce an immune response protein-based drugs that would otherwise elicit an immune response.

17 Claims, 7 Drawing Sheets

Specification includes a Sequence Listing.

(56) References Cited

U.S. PATENT DOCUMENTS

| | | | |
|---|---|---|---|
| 6,153,203 A | 11/2000 | Holmgren et al. | |
| 6,217,869 B1 | 4/2001 | Meyer et al. | |
| 6,224,794 B1 | 5/2001 | Amsden et al. | |
| 6,264,950 B1 | 7/2001 | Staerz | |
| 6,322,796 B1 | 11/2001 | Holmgren et al. | |
| 6,365,163 B1 | 4/2002 | Holmgren et al. | |
| 6,379,699 B1 | 4/2002 | Virtanen et al. | |
| 6,488,927 B2 | 12/2002 | Muzykantov et al. | |
| 6,512,103 B1 | 1/2003 | Dairaghi et al. | |
| 6,562,347 B1 | 5/2003 | Kwak et al. | |
| 6,703,488 B1 | 3/2004 | Burton et al. | |
| 6,737,057 B1 | 5/2004 | Zaghouani et al. | |
| 6,814,964 B2 | 11/2004 | Virtanen et al. | |
| 6,905,688 B2 | 6/2005 | Rosen et al. | |
| 6,953,675 B2 | 10/2005 | Leung et al. | |
| 7,041,287 B2 | 5/2006 | Muzykantov et al. | |
| 7,132,475 B2 | 11/2006 | Hubbel et al. | |
| 7,144,569 B1 | 12/2006 | Anderson et al. | |
| 7,148,329 B1 | 12/2006 | Figdor et al. | |
| 7,172,760 B2 | 2/2007 | Muzykantov et al. | |
| 7,175,988 B2 | 2/2007 | Roschke et al. | |
| 7,192,582 B2 | 3/2007 | Hudson et al. | |
| 7,285,642 B2 | 10/2007 | Figdor et al. | |
| 7,420,040 B2 | 9/2008 | Young et al. | |
| 7,420,041 B2 | 9/2008 | Young et al. | |
| 7,541,180 B2 | 6/2009 | Valiante et al. | |
| 7,585,508 B1 | 9/2009 | Prendergast | |
| 7,612,180 B2 | 11/2009 | Goldenberg et al. | |
| 7,704,943 B2 | 4/2010 | Griffin et al. | |
| 7,704,964 B2 | 4/2010 | Delcayre et al. | |
| 7,786,267 B2 | 8/2010 | Zurawski et al. | |
| 7,811,809 B2 | 10/2010 | Heyduk et al. | |
| 7,837,997 B2 | 11/2010 | Muzykantov et al. | |
| 7,884,190 B2 | 2/2011 | Cohen et al. | |
| 7,888,460 B2 | 2/2011 | Anderson et al. | |
| 7,892,743 B2 | 2/2011 | Owen et al. | |
| 7,932,294 B2 | 4/2011 | Satyam | |
| 7,994,283 B2 | 8/2011 | Valiante et al. | |
| 8,007,805 B2 | 8/2011 | George et al. | |
| 8,021,689 B2 | 9/2011 | Reddy et al. | |
| 8,057,798 B2 | 11/2011 | Zurawski et al. | |
| 8,058,400 B2 | 11/2011 | Figdor et al. | |
| 8,058,406 B2 | 11/2011 | Mi et al. | |
| 8,105,599 B2 | 1/2012 | Figdor et al. | |
| 8,236,934 B2 | 8/2012 | Banchereau et al. | |
| 8,252,902 B2 | 8/2012 | Barbas et al. | |
| 8,273,357 B2 | 9/2012 | Hacohen et al. | |
| 8,277,812 B2 | 10/2012 | Iannacone et al. | |
| 8,318,912 B2 | 11/2012 | Simon | |
| 8,323,696 B2 | 12/2012 | Hubbel et al. | |
| 8,329,144 B2 | 12/2012 | Anderson et al. | |
| 8,333,973 B2 | 12/2012 | Muzykantov et al. | |
| 8,343,497 B2 | 1/2013 | Shi et al. | |
| 8,343,498 B2 | 1/2013 | Alexis et al. | |
| 8,425,910 B2 | 4/2013 | Mi et al. | |
| 8,449,888 B2 | 5/2013 | Zurawski et al. | |
| 8,507,237 B2 | 8/2013 | Hermet et al. | |
| 8,518,410 B2 | 8/2013 | Zurawski et al. | |
| 8,551,476 B2 | 10/2013 | Mi et al. | |
| 8,562,998 B2 | 10/2013 | Shi et al. | |
| 8,580,253 B2 | 11/2013 | Rubin-Bejerano et al. | |
| 8,586,052 B2 | 11/2013 | Zurawski et al. | |
| 8,591,905 B2 | 11/2013 | Von Andrian et al. | |
| 8,592,364 B2 | 11/2013 | Swartz et al. | |
| 8,613,903 B2 | 12/2013 | Goldenberg et al. | |
| 8,617,823 B2 | 12/2013 | Rubin-Bejerano et al. | |
| 8,637,028 B2 | 1/2014 | Alexis et al. | |
| 8,673,293 B2 | 3/2014 | Martin et al. | |
| 8,685,408 B2 | 4/2014 | Tartour et al. | |
| 8,722,047 B2 | 5/2014 | Goldenberg et al. | |
| 8,728,481 B2 | 5/2014 | Banchereau et al. | |
| 8,859,629 B2 | 10/2014 | Van Delft et al. | |
| 8,889,140 B2 | 11/2014 | Lee et al. | |
| 8,906,381 B2 | 12/2014 | Iannacone et al. | |
| 8,932,595 B2 | 1/2015 | Iannacone et al. | |
| 8,961,991 B2 | 2/2015 | Zurawski et al. | |
| 8,992,917 B2 | 3/2015 | Goldenberg et al. | |
| 9,005,903 B2 | 4/2015 | Rubin-Bejerano et al. | |
| 9,066,984 B2 | 6/2015 | Mi et al. | |
| 9,102,730 B2 | 8/2015 | Zurawski et al. | |
| 9,102,734 B2 | 8/2015 | Zurawski et al. | |
| 9,187,561 B2 | 11/2015 | Goldenberg et al. | |
| 9,216,156 B2 | 12/2015 | Fleury et al. | |
| 9,233,072 B2 | 1/2016 | Alexis et al. | |
| 9,234,040 B2 | 1/2016 | Zurawski et al. | |
| 9,260,692 B2 | 2/2016 | Martin et al. | |
| 9,308,280 B2 | 4/2016 | Shi et al. | |
| 9,326,939 B2 | 5/2016 | Paulson et al. | |
| 9,416,186 B2 | 8/2016 | Zurawski et al. | |
| 9,439,859 B2 | 9/2016 | Alexis et al. | |
| 9,453,074 B2 | 9/2016 | Oh et al. | |
| 9,457,047 B2 | 10/2016 | Rubin-Bejerano et al. | |
| 9,474,717 B2 | 10/2016 | von Andrian et al. | |
| 9,517,257 B2 | 12/2016 | Hubbell et al. | |
| 9,518,087 B2 | 12/2016 | Hubbell et al. | |
| 9,522,183 B2 | 12/2016 | Paulson et al. | |
| 9,539,210 B2 | 1/2017 | von Andrian et al. | |
| 9,561,272 B2 | 2/2017 | Thomas et al. | |
| 9,688,991 B2 | 6/2017 | Levy et al. | |
| 9,751,945 B2 | 9/2017 | Ploegh et al. | |
| 9,814,780 B2 | 11/2017 | Hubbell et al. | |
| 9,850,296 B2 | 12/2017 | Hubbell et al. | |
| 9,878,048 B2 | 1/2018 | Hubbell et al. | |
| 9,901,645 B2 | 2/2018 | Hubbell et al. | |
| 9,901,646 B2 | 2/2018 | Hubbell et al. | |
| 10,046,056 B2 | 8/2018 | Hubbell et al. | |
| 10,800,838 B2 | 10/2020 | Hubbell et al. | |
| 10,821,157 B2 | 11/2020 | Hubbell et al. | |
| 10,919,963 B2 | 2/2021 | Hubbell et al. | |
| 10,940,209 B2 | 3/2021 | Hubbell et al. | |
| 10,946,079 B2 | 3/2021 | Hubbell et al. | |
| 10,953,101 B2 | 3/2021 | Hubbell et al. | |
| 2002/0004037 A1 | 1/2002 | Koteliansky et al. | |
| 2002/0038002 A1 | 3/2002 | Zaghouani | |
| 2002/0081298 A1 | 6/2002 | Zaghouani | |
| 2002/0103343 A1 | 8/2002 | Taylor et al. | |
| 2002/0187131 A1 | 12/2002 | Hawiger et al. | |
| 2002/0193572 A1 | 12/2002 | Leung et al. | |
| 2003/0022826 A1 | 1/2003 | Haynes | |
| 2003/0082643 A1 | 5/2003 | Hudson et al. | |
| 2003/0103967 A1 | 5/2003 | Zaghouani | |
| 2003/0104045 A1 | 6/2003 | Virtanen et al. | |
| 2003/0175921 A1 | 9/2003 | Barbas et al. | |
| 2003/0190676 A1 | 10/2003 | Barbas et al. | |
| 2003/0211078 A1 | 11/2003 | Heavner | |
| 2004/0052815 A1 | 3/2004 | Lycke | |
| 2004/0077843 A1 | 4/2004 | Burton et al. | |
| 2004/0146948 A1 | 7/2004 | Britton et al. | |
| 2004/0147721 A1 | 7/2004 | Valiante | |
| 2004/0185057 A1 | 9/2004 | Kirkby et al. | |
| 2004/0197314 A1 | 10/2004 | Delcayre et al. | |
| 2004/0258688 A1 | 12/2004 | Hawiger et al. | |
| 2005/0031628 A1 | 2/2005 | George et al. | |
| 2005/0053579 A1 | 3/2005 | Galipeau et al. | |
| 2005/0113297 A1 | 5/2005 | Francois et al. | |
| 2005/0118168 A1 | 6/2005 | Figdor et al. | |
| 2005/0201973 A1 | 9/2005 | Virtanen et al. | |
| 2005/0203022 A1 | 9/2005 | Gotwals et al. | |
| 2005/0220804 A1 | 10/2005 | Figdor et al. | |
| 2005/0250936 A1 | 11/2005 | Oppermann et al. | |
| 2006/0034864 A1 | 2/2006 | Zaghouani | |
| 2006/0127929 A1 | 6/2006 | Swager et al. | |
| 2006/0153881 A1 | 7/2006 | Narum et al. | |
| 2006/0173168 A1 | 8/2006 | Carlock et al. | |
| 2006/0178299 A1 | 8/2006 | Anderson et al. | |
| 2006/0257412 A1 | 11/2006 | Bowdish et al. | |
| 2006/0280679 A1 | 12/2006 | Bowdish et al. | |
| 2007/0059794 A1 | 3/2007 | Ideno et al. | |
| 2007/0111222 A1 | 5/2007 | Chasin et al. | |
| 2007/0122409 A1 | 5/2007 | Zaghouani | |
| 2007/0190615 A1 | 8/2007 | Cohen et al. | |
| 2007/0218053 A1 | 9/2007 | Zaghouani | |
| 2008/0031899 A1 | 2/2008 | Reddy et al. | |
| 2008/0131428 A1 | 6/2008 | Young et al. | |

(56) References Cited

U.S. PATENT DOCUMENTS

| | | |
|---|---|---|
| 2008/0160041 A1 | 7/2008 | Figdor et al. |
| 2008/0175971 A1 | 7/2008 | Anderson et al. |
| 2008/0178299 A1 | 7/2008 | Merkle et al. |
| 2008/0206262 A1 | 8/2008 | Banchereau et al. |
| 2008/0213267 A1 | 9/2008 | Young et al. |
| 2008/0227707 A1 | 9/2008 | Carlock et al. |
| 2008/0233143 A1 | 9/2008 | Jackson et al. |
| 2008/0241170 A1 | 10/2008 | Zurawski et al. |
| 2008/0254044 A1 | 10/2008 | Zurawski |
| 2008/0261262 A1 | 10/2008 | Godfrin |
| 2008/0274092 A1 | 11/2008 | Godfrin et al. |
| 2008/0305104 A1 | 12/2008 | Young et al. |
| 2008/0318852 A1 | 12/2008 | Anderson et al. |
| 2009/0004218 A1 | 1/2009 | Hacohen et al. |
| 2009/0017039 A1 | 1/2009 | Mi et al. |
| 2009/0123467 A1 | 5/2009 | Bedi et al. |
| 2009/0130104 A1 | 5/2009 | Muzykantov et al. |
| 2009/0142263 A1 | 6/2009 | Young et al. |
| 2009/0149656 A1 | 6/2009 | Singaram et al. |
| 2009/0181011 A1 | 7/2009 | Zaghouani |
| 2009/0191118 A1 | 7/2009 | Young et al. |
| 2009/0202622 A1 | 8/2009 | Fleury et al. |
| 2009/0269285 A1 | 10/2009 | Anderson et al. |
| 2009/0280132 A1 | 11/2009 | Zaghouani |
| 2009/0317381 A1 | 12/2009 | Plaut et al. |
| 2009/0324538 A1 | 12/2009 | Wong et al. |
| 2010/0003266 A1 | 1/2010 | Simon |
| 2010/0003338 A1 | 1/2010 | Hubbell et al. |
| 2010/0015131 A1 | 1/2010 | Mi et al. |
| 2010/0055189 A1 | 3/2010 | Hubbell et al. |
| 2010/0092425 A1 | 4/2010 | Von Andrian et al. |
| 2010/0098718 A1 | 4/2010 | Valiante |
| 2010/0129392 A1 | 5/2010 | Shi et al. |
| 2010/0129439 A1 | 5/2010 | Alexis et al. |
| 2010/0129820 A1 | 5/2010 | Kool et al. |
| 2010/0222407 A1 | 9/2010 | Segura et al. |
| 2010/0233251 A1 | 9/2010 | Von Andrian et al. |
| 2010/0239575 A1 | 9/2010 | Banchereau et al. |
| 2010/0285015 A1 | 11/2010 | Muzykantov et al. |
| 2010/0291080 A1 | 11/2010 | Lee et al. |
| 2010/0291082 A1 | 11/2010 | Zurawski |
| 2010/0297114 A1 | 11/2010 | Zurawski |
| 2010/0310612 A1 | 12/2010 | DuFour et al. |
| 2010/0316620 A1 | 12/2010 | Bourgeaux et al. |
| 2010/0322929 A1 | 12/2010 | Zurawski et al. |
| 2010/0330115 A1 | 12/2010 | Zurawski et al. |
| 2011/0014171 A1 | 1/2011 | Bourgeaux et al. |
| 2011/0033426 A1 | 2/2011 | Martin et al. |
| 2011/0044912 A2 | 2/2011 | Anderson et al. |
| 2011/0045049 A1 | 2/2011 | Rubin-Bejerano et al. |
| 2011/0064709 A1 | 3/2011 | Miller et al. |
| 2011/0064754 A1 | 3/2011 | Taylor et al. |
| 2011/0082075 A1 | 4/2011 | Prendergast |
| 2011/0091493 A1 | 4/2011 | Mohamadzadeh et al. |
| 2011/0105379 A1* | 5/2011 | Shulman ............... A61K 47/54 536/18.3 |
| 2011/0123536 A1 | 5/2011 | Chermann et al. |
| 2011/0143994 A1 | 6/2011 | Lycke |
| 2011/0177532 A1 | 7/2011 | Rubin-Bejerano et al. |
| 2011/0200632 A1 | 8/2011 | Jackson et al. |
| 2011/0206759 A1 | 8/2011 | Swartz et al. |
| 2011/0268804 A1 | 11/2011 | Shi et al. |
| 2011/0268805 A1 | 11/2011 | Alexis et al. |
| 2011/0293644 A1 | 12/2011 | Anderson et al. |
| 2011/0311542 A1 | 12/2011 | Mi et al. |
| 2012/0004643 A1 | 1/2012 | Zurawski et al. |
| 2012/0009140 A1 | 1/2012 | Godfrin et al. |
| 2012/0014960 A1 | 1/2012 | Mi et al. |
| 2012/0027808 A1 | 2/2012 | Iannacone |
| 2012/0039989 A1 | 2/2012 | Hubbel et al. |
| 2012/0058180 A1 | 3/2012 | Kren et al. |
| 2012/0076831 A1 | 3/2012 | Miller et al. |
| 2012/0087890 A1 | 4/2012 | Iannacone et al. |
| 2012/0107301 A1 | 5/2012 | Bowdish et al. |
| 2012/0121570 A1 | 5/2012 | Godfrin |
| 2012/0121592 A1 | 5/2012 | Oh et al. |
| 2012/0128635 A1 | 5/2012 | Gregory et al. |
| 2012/0129210 A1 | 5/2012 | Bourgeaux et al. |
| 2012/0178139 A1 | 7/2012 | Hubbel et al. |
| 2012/0207745 A1 | 8/2012 | Godfrin et al. |
| 2012/0237513 A1 | 9/2012 | Zurawski et al. |
| 2012/0276095 A1 | 11/2012 | Langermann et al. |
| 2012/0282281 A1 | 11/2012 | Banchereau et al. |
| 2013/0004427 A1 | 1/2013 | El-Sayed et al. |
| 2013/0022634 A1 | 1/2013 | Lycke |
| 2013/0053543 A1 | 2/2013 | Davis et al. |
| 2013/0059299 A1 | 3/2013 | Parr et al. |
| 2013/0071413 A1 | 3/2013 | Simon |
| 2013/0078216 A1 | 3/2013 | Dunlevy et al. |
| 2013/0078267 A1 | 3/2013 | Anderson et al. |
| 2013/0101463 A1 | 4/2013 | Mambrini et al. |
| 2013/0115230 A1 | 5/2013 | Simon |
| 2013/0129790 A1 | 5/2013 | Alexis et al. |
| 2013/0164364 A1 | 6/2013 | Paulson et al. |
| 2013/0171074 A1 | 7/2013 | Barbas et al. |
| 2013/0171233 A1 | 7/2013 | Paulson et al. |
| 2013/0236533 A1 | 9/2013 | Von Andrian et al. |
| 2013/0287810 A1 | 10/2013 | Mohamadzadeh et al. |
| 2013/0287857 A1 | 10/2013 | Von Andrian et al. |
| 2013/0295120 A1 | 11/2013 | Zurawski et al. |
| 2013/0318648 A1 | 11/2013 | Anderson et al. |
| 2013/0323786 A1 | 12/2013 | Mi et al. |
| 2013/0336991 A1 | 12/2013 | Mi et al. |
| 2014/0037736 A1 | 2/2014 | Shi et al. |
| 2014/0079728 A1 | 3/2014 | Jackson et al. |
| 2014/0127198 A1 | 5/2014 | Zurawski et al. |
| 2014/0127301 A1 | 5/2014 | Alexis et al. |
| 2014/0134168 A1 | 5/2014 | Zurawski et al. |
| 2014/0199315 A1 | 7/2014 | Mi et al. |
| 2014/0205630 A1 | 7/2014 | Tartour |
| 2014/0212445 A1 | 7/2014 | Martin et al. |
| 2014/0227268 A1 | 8/2014 | Banchereau et al. |
| 2014/0234344 A1 | 8/2014 | Banchereau et al. |
| 2014/0308238 A1 | 10/2014 | Rubin-Bejerano et al. |
| 2014/0314865 A1 | 10/2014 | Von Andrian et al. |
| 2014/0377291 A1 | 12/2014 | Fischbach et al. |
| 2014/0377838 A1 | 12/2014 | Maynard et al. |
| 2015/0104478 A1 | 4/2015 | Lee et al. |
| 2015/0166659 A1 | 6/2015 | Goldenberg et al. |
| 2015/0191730 A1 | 7/2015 | Levy et al. |
| 2015/0250862 A1 | 9/2015 | Cantor et al. |
| 2015/0299329 A1 | 10/2015 | Zurawski et al. |
| 2015/0307545 A1 | 10/2015 | Jackson et al. |
| 2016/0015821 A1 | 1/2016 | Hubbell et al. |
| 2016/0022792 A1 | 1/2016 | Zurawski et al. |
| 2016/0024212 A1 | 1/2016 | Goldenberg et al. |
| 2016/0031988 A1 | 2/2016 | Zurawski et al. |
| 2016/0058792 A1 | 3/2016 | Quintana et al. |
| 2016/0060324 A1 | 3/2016 | Paulson et al. |
| 2016/0060358 A1 | 3/2016 | Hay |
| 2016/0083468 A1 | 3/2016 | Mi et al. |
| 2016/0108096 A1 | 4/2016 | Thompson et al. |
| 2016/0243248 A1 | 8/2016 | Hubbell et al. |
| 2016/0346384 A1 | 12/2016 | Porcelli et al. |
| 2016/0354453 A1 | 12/2016 | Hubbell et al. |
| 2016/0375126 A1 | 12/2016 | Oh et al. |
| 2017/0007708 A1 | 1/2017 | Hubbell et al. |
| 2017/0020926 A1 | 1/2017 | Mata-Fink et al. |
| 2017/0066825 A1 | 3/2017 | Hubbell et al. |
| 2017/0066828 A1 | 3/2017 | Goldenberg et al. |
| 2017/0121379 A1 | 5/2017 | Zhang et al. |
| 2017/0137513 A1 | 5/2017 | Vallera et al. |
| 2017/0252417 A1 | 9/2017 | Irvine et al. |
| 2017/0296636 A9* | 10/2017 | Hubbell ............... A61K 47/549 |
| 2017/0320933 A1 | 11/2017 | Mannie |
| 2017/0326213 A1 | 11/2017 | Jajosky et al. |
| 2018/0000916 A1 | 1/2018 | Zurawski et al. |
| 2018/0094071 A1 | 4/2018 | Zurawski et al. |
| 2018/0100011 A1 | 4/2018 | Hubbell et al. |
| 2018/0104284 A1 | 4/2018 | Wallecha et al. |
| 2018/0112034 A1 | 4/2018 | Maynard |
| 2018/0117171 A1 | 5/2018 | Mooney et al. |
| 2018/0271986 A1 | 9/2018 | Hubbell et al. |
| 2018/0303951 A1 | 10/2018 | Hubbell et al. |

(56) References Cited

U.S. PATENT DOCUMENTS

| | | |
|---|---|---|
| 2019/0382479 A1 | 12/2019 | Hubbell et al. |
| 2020/0101146 A1 | 4/2020 | Hubbell et al. |
| 2020/0101169 A1 | 4/2020 | Hubbell et al. |
| 2020/0121762 A1 | 4/2020 | Hubbell et al. |
| 2020/0129601 A1 | 4/2020 | Hubbell et al. |
| 2020/0129625 A1 | 4/2020 | Hubbell et al. |
| 2020/0129629 A1 | 4/2020 | Hubbell et al. |

FOREIGN PATENT DOCUMENTS

| | | |
|---|---|---|
| CN | 101443351 | 5/2009 |
| CN | 101750244 | 6/2010 |
| CN | 102791293 | 11/2012 |
| CN | 103282380 | 9/2013 |
| CN | 103547272 | 1/2014 |
| CN | 106432371 | 2/2017 |
| EP | 0119650 | 9/1984 |
| EP | 0175617 | 10/1991 |
| EP | 0088695 | 6/1992 |
| EP | 0173629 | 6/1992 |
| EP | 0480041 | 6/1993 |
| EP | 0308208 | 12/1993 |
| EP | 0251455 | 5/1994 |
| EP | 0294294 | 5/1995 |
| EP | 0789715 | 8/1997 |
| EP | 0808366 | 11/1997 |
| EP | 0722340 | 4/1998 |
| EP | 0505357 | 3/1999 |
| EP | 0602290 | 8/1999 |
| EP | 0978564 | 2/2000 |
| EP | 1012308 | 6/2000 |
| EP | 630407 | 8/2000 |
| EP | 1046651 | 10/2000 |
| EP | 1093464 | 4/2001 |
| EP | 1301541 | 4/2003 |
| EP | 0743856 | 7/2003 |
| EP | 1370588 | 12/2003 |
| EP | 1409009 | 4/2004 |
| EP | 1292621 | 9/2006 |
| EP | 1838734 | 10/2007 |
| EP | 1853313 | 11/2007 |
| EP | 1028978 | 1/2008 |
| EP | 1086137 | 6/2008 |
| EP | 1938836 | 7/2008 |
| EP | 1440156 | 8/2008 |
| EP | 1619208 | 10/2008 |
| EP | 1996700 | 12/2008 |
| EP | 1996701 | 12/2008 |
| EP | 1045861 | 3/2009 |
| EP | 2125012 | 12/2009 |
| EP | 2178896 | 4/2010 |
| EP | 1516881 | 6/2010 |
| EP | 2238986 | 10/2010 |
| EP | 2315779 | 5/2011 |
| EP | 1417229 | 6/2011 |
| EP | 2344185 | 7/2011 |
| EP | 2344187 | 7/2011 |
| EP | 2394657 | 12/2011 |
| EP | 2394661 | 12/2011 |
| EP | 2406290 | 1/2012 |
| EP | 2428226 | 3/2012 |
| EP | 2478917 | 7/2012 |
| EP | 2066294 | 10/2012 |
| EP | 2527363 | 11/2012 |
| EP | 2598120 | 6/2013 |
| EP | 2618817 | 7/2013 |
| EP | 2620157 | 7/2013 |
| EP | 2630967 | 8/2013 |
| EP | 1904104 | 9/2013 |
| EP | 1991564 | 9/2013 |
| EP | 2115129 | 11/2013 |
| EP | 2684889 | 1/2014 |
| EP | 1443963 | 5/2014 |
| EP | 1664270 | 5/2014 |
| EP | 2115002 | 8/2014 |
| EP | 1605974 | 11/2014 |
| EP | 1850832 | 12/2014 |
| EP | 2114985 | 12/2014 |
| EP | 2283358 | 4/2015 |
| EP | 2213742 | 1/2016 |
| EP | 2982695 | 2/2016 |
| EP | 2983791 | 2/2016 |
| EP | 2989123 | 3/2016 |
| EP | 2346528 | 4/2016 |
| EP | 2406286 | 5/2016 |
| EP | 2205273 | 9/2016 |
| EP | 3091034 | 11/2016 |
| EP | 2406288 | 12/2016 |
| EP | 2406289 | 2/2017 |
| EP | 2217269 | 4/2017 |
| EP | 2344186 | 4/2017 |
| EP | 2630966 | 4/2017 |
| JP | S5742852 A | 3/1982 |
| JP | S59173762 A | 10/1984 |
| JP | H09-509572 | 9/1997 |
| JP | 2003-519619 | 6/2003 |
| JP | 2004-526452 | 9/2004 |
| JP | 2007-510915 | 4/2007 |
| JP | 2007-312776 | 12/2007 |
| JP | 2009-505049 | 2/2009 |
| JP | 2009-060894 | 3/2009 |
| JP | 2009-149664 | 7/2009 |
| JP | 2013-516967 | 5/2013 |
| JP | 2014-159492 | 9/2014 |
| JP | 2014-532799 | 12/2014 |
| JP | 106432371 | 2/2017 |
| JP | 2017507180 | 3/2017 |
| JP | 2018-072431 | 8/2018 |
| WO | WO 1991/008770 | 6/1991 |
| WO | WO 1992/05801 | 4/1992 |
| WO | WO 1992/22310 | 12/1992 |
| WO | WO 1995/06737 | 3/1995 |
| WO | WO 1995/22977 | 8/1995 |
| WO | WO 1996/023882 | 8/1996 |
| WO | WO 1996/040245 | 12/1996 |
| WO | WO 1998/06737 | 2/1998 |
| WO | WO 1999/036437 | 7/1999 |
| WO | WO 1999/38536 | 8/1999 |
| WO | WO 00/01732 | 1/2000 |
| WO | WO 2000/074717 | 12/2000 |
| WO | WO 2001/022995 | 4/2001 |
| WO | WO 2001/025793 | 4/2001 |
| WO | WO 2002/004522 | 1/2002 |
| WO | WO 2002/072799 | 9/2002 |
| WO | WO 2002/083262 | 10/2002 |
| WO | WO 2002/102407 | 12/2002 |
| WO | WO 2003/064464 | 8/2003 |
| WO | WO 2003/066820 | 8/2003 |
| WO | WO 2003/104273 | 12/2003 |
| WO | WO 2004/034966 | 4/2004 |
| WO | WO 2004/035619 | 4/2004 |
| WO | WO 2004/045520 | 6/2004 |
| WO | WO 2004/098645 | 11/2004 |
| WO | WO 2005/045436 | 5/2005 |
| WO | WO 2005/105129 | 11/2005 |
| WO | WO 2006/002382 | 1/2006 |
| WO | WO 2006/016247 | 2/2006 |
| WO | WO 2006/093524 | 9/2006 |
| WO | WO 2007/008300 | 1/2007 |
| WO | WO 2007/017556 | 2/2007 |
| WO | WO 2007/095748 | 8/2007 |
| WO | WO 2007/097934 | 8/2007 |
| WO | WO 2007/098254 | 8/2007 |
| WO | WO 2007/099387 | 9/2007 |
| WO | WO 2007/099446 | 9/2007 |
| WO | WO 2007/101698 | 9/2007 |
| WO | WO 2007/150020 | 12/2007 |
| WO | WO 2008/063849 | 5/2008 |
| WO | WO 2009/018500 | 2/2009 |
| WO | WO 2009/019317 | 2/2009 |
| WO | WO 2009/056332 | 5/2009 |
| WO | WO 2009/078796 | 6/2009 |
| WO | WO 2009/086552 | 7/2009 |
| WO | WO 2009/120893 | 10/2009 |

(56) References Cited

FOREIGN PATENT DOCUMENTS

| WO | WO 2010/042870 | 4/2010 |
|---|---|---|
| WO | WO 2010/045518 | 4/2010 |
| WO | WO 2010/060155 | 6/2010 |
| WO | WO 2010/076517 | 7/2010 |
| WO | WO 2010/085509 | 7/2010 |
| WO | WO 2011/012715 | 2/2011 |
| WO | WO 2011/051346 | 5/2011 |
| WO | WO 2011/086143 | 7/2011 |
| WO | WO 2011/092715 | 8/2011 |
| WO | WO 2011/112482 | 9/2011 |
| WO | WO 2012/021512 | 2/2012 |
| WO | WO 2012/057671 | 5/2012 |
| WO | WO 2012/083185 | 6/2012 |
| WO | WO 2012/112690 | 8/2012 |
| WO | WO 2012/167088 | 12/2012 |
| WO | WO 2013/121296 | 8/2013 |
| WO | WO 2013/160865 | 10/2013 |
| WO | WO 2014/011465 | 1/2014 |
| WO | WO 2014/023709 | 2/2014 |
| WO | WO 2014/052545 | 4/2014 |
| WO | WO 2014/135528 | 9/2014 |
| WO | WO 2014/169255 | 10/2014 |
| WO | WO 2015/140648 | 9/2015 |
| WO | WO 2015/157595 | 10/2015 |
| WO | WO 2015/171863 | 11/2015 |
| WO | WO 2015/175957 | 11/2015 |
| WO | WO 2016/022971 | 2/2016 |
| WO | WO 2016/044655 | 3/2016 |
| WO | WO 2016/044661 | 3/2016 |
| WO | WO 2016/070050 | 5/2016 |
| WO | WO 2016/210447 | 12/2016 |
| WO | WO 2017/015141 | 1/2017 |
| WO | WO 2017/023779 | 2/2017 |
| WO | WO 2017/025889 | 2/2017 |
| WO | WO 2017/041053 | 3/2017 |
| WO | WO 2017/044308 | 3/2017 |
| WO | WO 2017/046652 | 3/2017 |
| WO | WO 2017/058996 | 4/2017 |
| WO | WO 2017/066484 | 4/2017 |
| WO | WO 2017/109134 | 6/2017 |
| WO | WO 2017/112899 | 6/2017 |
| WO | WO 2017/139498 | 8/2017 |
| WO | WO 2017/139787 | 8/2017 |
| WO | WO 2016104647 | 10/2017 |
| WO | WO 2017/192785 | 11/2017 |
| WO | WO 2017/192786 | 11/2017 |
| WO | WO 2018/232176 | 12/2018 |
| WO | WO 2019/098682 | 5/2019 |
| WO | WO 2019/191079 | 10/2019 |
| WO | WO 2019/0215590 | 11/2019 |
| WO | WO 2021/053589 | 3/2021 |

OTHER PUBLICATIONS

"SubName: Full=Putative Transcriptional Regulator, ArsR Family;", XP002717163, Retrieved From EBI Accession No. UNIPROT:D2RZT2, Database Accession No. D2RZT2 (Mar. 2, 2010).

"SubName: Full=Putative Uncharacterized Protein;", XP002717158, Retrieved From EBI Accession No. UNIPROT:C0NJE0, Database Accession No. C0NJE0 (May 5, 2009).

"SubName: Full=Putative Uncharacterized Protein;", XP002717160, Retrieved From EBI Accession No. UNIPROT:B9PUP0, Database Accession No. B9PUP0 (Mar. 24, 2009).

"SubName: Full=Uncharacterized Protein;", XP002717157, Retrieved From EBI Accession No. UNIPROT:B5E9K2 Database Accession No. B5E9K2 (Oct. 14, 2008).

Ahmed et al., "Carbohydrate-based materials for targeted delivery of drugs and genes to the liver." Nanomedicine (Lond.) (205) 10(14), 2263-2288.

Albert et al., "Immature dendritic cells phagocytose apoptotic cells via vI35 and CD36, and cross-present antigens to cytotoxic T lymphocytes," Journal of Experimental Medicine, vol. 188(7): 1359-1368 (Oct. 5, 1998).

Amagai, et al., "Desmoglein as a target in skin disease and beyond", J Invest Dermatol, Mar. 2012; in 23 pages.

Andre et al., "Determination of modulation of ligand properties of synthetic complex-type biantennary N-glycans by introduction of bisecting GlcNAc in silico, in vitro and in vivo" Eur. J. Biochem. 2004;271(1):118-134.

Arnaboldi et al., "Suppression of Th 1 and Th17, but not Th2, responses in a CD8+ T cell-mediated model of oral tolerance," Mucosal Immunology, vol. 2(5):427-438 (Sep. 2009).

Bailon et al., "Rational design of a potent, long-lasting form of interferon: A 40 kDa branched polyethylene glycol-conjugated interferon-2a for the treatment of hepatitis C," Bioconjugate Chemistry, vol. 12(2):195-202 (2001).

Baker, et al. "Hybrid Insulin Peptides are Autoantigens in Type 1 Diabetes", Diabetes, Sep. 2019, vol. 68, pp. 1830-1840.

Benaglia et al. "Searching for More Effective Agents and Conditions for the RAFT Polymerization of MMA: Influence of Dithioester Substituents, Solvent, and Temperature" Macromolecules 2005, 38, 3129-3140 (Year: 2005).

Bielekova et al., "Expansion and Functional Relevance of High-Avidity Myelin-Specific CD4 T Cells in Multiple Sclerosis," J Immunol 2004; 172:3893-3904.

Bigbee et al., "Binding specificities of eight monoclonal antibodies to human glycophorin A—studies with McM, and MkEn(UK) variant human erythrocytes and M- and MNv-type chimpanzee erythrocytes," Dec. 1, 1984, J. Immunol., 133(6): 3149-3155 (1984).

Blancher et al., "Reactivity of anti-glycophorin monoclonal antibodies (Mabs) in tests with red cells of non-human primates," Jan. 1, 1997, Transfus Clin Biol 4, 81-85 (1997).

Boyer et al. "Bioapplications of RAFT Polymerization". Chem. Rev. 2009, 109, 5402-5436 (Year: 2009).

Brack et al., "Tumor-targeting properties of novel antibodies specific to the large isoform of tenascin-C," Clinic Cancer Research, vol. 12(10):3200-3208 (May 15, 2006).

Bursch et al., "Langerhans cells are not required for the COB T cell response to epidermal self-antigens," Journal of Immunology, vol. 182(8):4657-4664 (Apr. 15, 2009).

Caja et al., "Antibodies in celiac disease: implications beyond diagnostics," Cellular & Molecular Immunology (2011) 8, 103-109.

Calvaresi and Hergenrother. "Glucose conjugation for the specific targeting and treatment of cancer"; Chem Sci. Jun. 2013; 4(6): 2319-2333 (Year: 2013).

Cao et al., "Molecular Beacon Aptamers for Protein Monitoring in Real-Time and in Homogeneous Solutions," Current Proteomics, 2:31-401, (2005).

Chasis et al., "Signal Transduction by Glycophorin A: Role of Extracellula Rand Cytoplasmic Domains in a Modulatable Process", The Journal of Cell Biology, 107:1351-1357, (Oct. 1988).

Cheremisinoff. Condensed Encyclopedia of Polymer Engineering Terms, Butterworth-Heinemann, 2001, pp. 39-81. (Year: 2001).

Chiarantini et al., "Red Blood Cells as Delivery System for Recombinant HSV-1 Glycoprotein B: Immunogenicity and Protection in Mice," Vaccine, 15(3):276-280, (1997).

Ciccocioppo, R. et al, "The immune recognition of gluten in coeliac disease", British Society for Immunology, Clinical and Experimental Immunology, Feb. 1, 2005, pp. 408-416.

Clements et al., "The Crystal Structure of Myelin Oligodendrocyte Glycoprotein, a key autoantigen in multiple sclerosis," Proc. Natl. Acad. Sci. (PNAS) vol. 100: 11059-11064 (Sep. 2003).

Coulstock et al., "Liver-targeting of interferon-alpha with tissue-specific domain antibodies" Plos One, Public Library of Science, US, vol. 8, No. 2, Jan. 1, 2013.

Craig et al., "Processing of C3b-Opsonized Immune Complexes Bound to Non-Complement Receptor 1 (CR1) Sites on Red Cells: Phagocytosis, Transfer and Associations with CR1," *J. Immunol* 2005, 174, 3059-3066.

Crispe et al., "Cellular and molecular mechanisms of liver tolerance," Immunol Rev., 213: 101-118 (2006).

Dane et al., "Isolation of cell specific peptide ligands using fluorescent bacterial display libraries-" Journal of Immunological Methods, vol. 309(1-2):120-129, (Jan. 2006).

(56) References Cited

OTHER PUBLICATIONS

Darrah et al., "IL-10 production differentially influences the magnitude, quality, and protective capacity of Th1 responses depending on the vaccine platform," Journal of Experimental Medicine, vol. 207(7):1421-1433 (2010).

Deng, et al., "Disulfide-Based Self-Immolative Linkers and Functional Bioconjugates for Biological Applications." Macromolecular Rapid Communication, Advanced Science News (2020), 41, 1900531, in 14 pages.

Dennis et al., "Albumin Binding as a General Strategy forImproving the Pha rmacokinetics of Proteins-" Journal of Biological Chemistry, vol. 277(38):35035-35043 (Sep. 20, 2002).

Devalapally et al., "Poly(ethylene oxide)-modified Poly(beta-amino ester) Nanoparticles as a pH-sensitive System for Tumor-targeted Delivery of Hydrophobic Drugs: Part 3. Therapeutic Efficacy and Safety Studies in Ovarian CanceRXenog Raft Model," Cancer Chemotherapy Pharmacology, 59:477-484, (2007).

Dhalluin et al., "Structural and biophysical characterization of the 40 kDa PEG-interferon-2a and its individual positional isomers," Bioconjugate Chemistry, vol. 16(3):504-517 (2005).

Di Lorenzo et al., "Translational Mini-Review Series on Type 1 Diabetes: Systemic analysis of T cell epitopes in autoimmune diabetes," 2007, Clin Exp Immunol, vol. 148: 1-146.

Dienst et al., "Specific occlusion of mu rine and human tumor vasculature by VCAM-1-targeted recombinant fusion proteins," Journal of The National Cancer Institute, vol. 97(10):733-747, (2005).

Dieterich et al., "Identification of Tissue Transglutaminase as the Autoantigen of Celiac Disease," Nature Medicine vol. 3 p. 797-801 (1997).

Dominguez-Soto, et al., "The DC-SIGN-related lectin LSECtin mediates antigen capture and pathogen binding by human myeloid cells" www.bloodjournal.org. Immunobiology, Jun. 15, 2007, vol. 109, No. 12, pp. 5337-5345.

Dornmair Klaus et al: "T-cell-mediated autoimmunity: Novel techniques to characterize autoreactive T-cell receptors", American Journal of Pathology, vol. 163, No. 4, Oct. 2003 (Oct. 2003), pp. 1215-1226, ISSN: 0002-9440.

Ducan, R. Development of HPMA copolymer-anticancer conjugates: Clinical experience and lessons learnt. Advanced Drug Delivery Reviews 61 (2009) pp. 1131-1148.

Ferguson et al., "Armed response: How dying cells influence T-cell functions," Immunology Review, vol. 241 (1):77-88 (May 2011).

Fife et al., "Insulin-induced remission in new-onset NOD mice is maintained by the PD-1-PD-L 1 pathway," The Journal of Experimental Medicine, vol. 203(12):2737-2747, (Nov. 27, 2006).

Fishburn, "The pharmacology of PEGylation: balancing PD with PK to generate novel therapeutics," Journal of Pharmaceutical Sciences vol. 97(10):4167-4183 (Oct. 10, 2008).

Folgori A et al: "A general strategy to identify mimotopes of pathological antigens using only random peptide libraries and huamn sera", EMBO (European Molecular Biology Organization) Journal, vol. 13, No. 9, May 1, 1994 (May 1, 1994), pp. 2236-2243, ISSN: 0261-4189.

Fonsatti et al., "Targeting cancer vasculature via endoglin/CD105: A novel antibody-based diagnostic and therapeutic strategy in solid tumours," Cardiovascular Research, vol. 86(1):12-19, (2010).

Gadaleta et al., "Trans-arterial chemoembolization as a therapy for liver tumours: New clinical developments and suggestions for combination with angiogenesis inhibitors," Critical Reviews in Oncology/Hematology, vol. 80:40-53 (2011).

Gao et al., "In situ growth of a stoichiometric PEG-like conjugate at a protein's N-terminus with significantly improved pharmacokinetics-" Proceedings of the National Academy Sciences vol. 106(36): 15231-15236 (Sep. 8, 2009).

Geng et al., "Site-directed conjugation of "clicked" glycopolymers for form glycoprotein mimics: binding to mammalian lectin and induction of immunological function." J Am Chem Soc. Dec. 12, 2007;129(49):15156-63.

Getts et al., "Have We Overestimated the Benefit of Human(ized) Antibodies?" Landes Bioscience, 2(6):682-694, (Nov./Dec. 2010).

Getz et al., "Protease-Resistant Peptide Ligands From a Knottin Scaffold Library," ACS Chemical Biology, 8 Pages, (May 26, 2011).

Godsel et al., "Prevention of autoimmune myocarditis through the induction of antigen-specific peripheral immune tolerance-" Circulation vol. 103(12):1709-1714 (2001).

Gorovits et al., "Proposed mechanism of off-target toxicity for antibody-drug conjugates driven by mannose receptor uptake," Cancer Immunol Immunother (2013) 62:217-233.

Gorzelany et al., "Protein replacement therapies for rare diseases: a breeze for regulatory approval?" Science Translational Medicine 5, 178fs10 (2013).

Granoff et al., "A Novel Mimetic Antigen Eliciting Protective Antibody to Neisseria meningitidis" J Immunol 2001; 167:6487-6496.

Green et al., "Immunogenic and tolerogenic cell death," National Review of Immunology vol. 9(5):353-363, (May 2009).

Grimm et al., "Memory of tolerance and induction of regulatory T cells by erythrocyte-targeted antigens." *Scientific Reports* 2015, 5:159907, 11 pages.

Gupta et al., "Expression, purification, and characterization of an anti-RBCFab-p24 fusion protein for hemagglutination-based rapid detection of antibodies to HIV in whole blood." Protein Expression and Purification 26 (2002) 162-170.

Gurwitz, "Peptide Mimetics: Fast-Forward Look" Drug Development Research 78:231-235, Year 2017.

Hackel et al., "Picomolar affinity fibronectin domains engineered utilizing loop length diversity, recursive mutagenesis, and loop shuffling," Journal of Molecular Biology, vol. 381(5):1238-1252, (Sep. 19, 2008).

Hall et al., "Identification of peptide ligands facilitating nanoparticle attachment toerythrocytes," Biotechnology Progess, vol. 23(3):749-754 (2007).

Hasselberg et al, "ADP-ribosylation controls the outcome of tolerance or enhanced priming following mucosal immunization" The Journal of Immunology, Aug. 24, 2016.

Hirosue et al., "Antigen delivery to dendritic cells by poly(propylene sulfide) Nanoparticles with disulfide conjugated peptides: Crosspresentation and T cell activation." Vaccine 28, Elsevier Inc. (2010) p. 7897-7906.

Holz et al., "CD8+ T cell tolerance following antigen recognition on hepatocytes," Journal of Autoimmunity, vol. 34 (1):15-22 (2010).

https://en.wikipedia.org/wiki/Reteplase accessed Apr. 13, 2020, printed Apr. 23, 2020 in 2 pages.

https://en.wikipedia.org/wiki/Tenecteplase, accessed Apr. 13, 2020, printed Apr. 23, 2020 in 4 pages.

Huang et al., "Characterization of poly(ethylene glycol) and PEGylated products by LC/MS with postcolumn addition of amines," Analytical Chemistry, vol. 81(2):567-577 (Jan. 15, 2009).

Huang et al., "Tumor infarction in mice by antibody-directed targeting of tissue factor to tumor vasculature," Science, vol. 275(5299):547-550 (Jan. 24, 1997).

Ichikawa et al., "Hepatic stellate cells function as regulatory bystanders," Journal of Immunology, vol. 186 (10):5549-5555 (May 15, 2011).

Immunogenic, Definition of Immunogenic by Merriam-Webster, https://www.merriam-webster.com/dictionary/immunogenic[May 10, 2019 11:59:27 AM], retrieved on May 10, 2019, in 9 pages.

International Search Report and Written Opinion from corresponding PCT Application No. PCT/IB2013/000684, 12 pages, dated Jul. 9, 2013.

International Search Report and Written Opinion from corresponding PCT Application No. PCT/US2011/047078, 4 pages, dated May 1, 2012.

International Search Report for Application No. PCT/EP2014/054161 issued on May 26, 2014.

Jain, et al., "Mutual prodrugs containing bio-cleavable and drug releasable disulfide linkers." Bioorganic Chemistry 49, Elsevier Inc. (2013) p. 40-48.

Janeway et al., "The complement system and innate immunity," Immunology: the Immune System in Health and Disease, 5th Edition. New York: Garland Science (2001).

(56) References Cited

OTHER PUBLICATIONS

Janeway et al., Immuno Biology, 8th Edtition, Garland Science (2012).
Jewett et al., "Cu-free click cycloaddition reactions in chemical biology," Chem Soc Rev. Apr. 2010; 39(4): 1272-1279.
Jones et al., "Localization of Pectic Galactan in Tomato Cell Walls Using a Monoclonal Antibody Specific to (1->4)-β-D-Galactan" Plant Physiol. 1997; 113:1405-1412.
Julyan et al "Preliminary clinical study of the distribution of HPMA copolymers bearing doxorubicin and galactosamine" Journal of Controlled Release 57 (1999) pp. 281-290.
Karim et al. "Hepatic expression and cellular distribution of the glucose transporter family"; World J Gastroenterol Dec. 14, 2012; 18(46): 6771-6781 (Year: 2012).
Keefe et al.,"Aptamers as therapeutics," Nature Reviews Drug Discovery, vol. 9(7):537-550 (2010).
Kenrick et al., "Bacterial Display Enables Efficient and Quantitative Peptide Affinity Maturation," Protein Engineering Design & Selection, vol. 23(1 ):9-17 (2010).
Khandelwal et al., "Assessment of survival of aging erythrocyte in circulation and attendant changes in size and CD147 expression by a novel two step biotinylation method," Experimental Gerontology, vol. 41(9):855-861 (Aug. 4, 2006).
Kim et al "Imaging and therapy of liver fibrosis using bioreducible polyethylenimine/siRNA complexes conjugated with N-acetylglucosamine as a targeting moiety" Biomaterials 34:6504-6514 (2013).
Kim et el., "Specific Binding of Glucose-derivatized Polymers to the Asialoglycoprotein Receptor of Mouse Primary Hepatocytes." The Journal of Biological Chemistry, vol. 276, No. 38, pp. 35312-35319, Sep. 21, 2001.
Kina et al., "The Monoclonal Antibody TER-119 Recognizes a Molecule Associated with Glycophorin A and Specifically Marks the Late Stages of Murine Erythroid Lineage," British Journal of Haematolgy, vol. 109:280-287 (2000).
King et al. "Antibody responses to bee melittin (Api m 4) and hornet antigen 5 (Dol m 5) in mice treated with the dominant T-cell Epitope peptides" Journal of Allergy and Clinical Immunology, vol. 101, Issue 3, Mar. 1998, pp. 397-403.
Klebe. "Optimization of Lead Structures", Drug Design, Springer-Verlag Berlin Heidelberg 2013, pp. 153-171. (Year: 2013).
Kontos et al., "Engineering antigens for in situ erythrocyte binding induces T-cell deletion," Proceeding of the National Academy Sciences, Dec. 17, 2012, vol. 110, No. 1, p. E60-E68.
Kontos et al., "Improving Protein Pharmacokinetics by Engineering Erythrocyte Affinity," Molecular Pharmaceutics, 2010, vol. 7, No. 6, p. 2141-2147.
Kontos, "Engineering Erythrocyte Affinity for Improved Pharmacokinetics and Immune Tolerogenesis", Thesis, 106 Pages (Jun. 23, 2011).
Kontos, et al., "Engineering antigen-specific immunological tolerance", www.sciencedirect.com, Current Opinion in Immunology, Jul. 8, 2015, 35:80-88.
Kopecek et al. "HPMA copolymers: Origins, early developments, present, and future." Advanced Drug Delivery Reviews 62, (2010) pp. 122-149.
Kravtzoff et al., "Tolerance Evaluation of L-asparaginase loaded in red blood cells," 1996, Eur J Clin Pharmacol, vol. 51: 221-225.
Krebber et al., "Reliable Cloning of Functional Antibody Variable domains from Hybridomas and Spleen Cell Repertoires Employing a Reengineered Phage Display System," Journal of Immunological Methods, vol. 201 :35-55 (1997).
La Rosa, et al., "The Innate Immune System in Allograft Rejection and Tolerance," J. Immunol., 2007, 178:7503-7509.
Langer et al., "Optimization of the Preparation Process for Human Serum Albumin (HSA) Nanoparticles," International Journal of Pharmaceutics, 257:169-180, (2003).
Lee et al., "Aptamers as Molecular Recognition Elements for Electrical Nanobiosensors," Analytical and Bioanalytical Chemistry, 390:1023-1032, (2008).
Lee et al., "Signaling pathways downstream of pattern-recognition receptors and their cross talk," Annual Review of Biochemistry, vol. 76:447-480 (Feb. 28, 2007).
Lehrman et al., "The Binding of Fucose-containing Glycoproteins by Hepatic Lectins" The Journal of Biological Chemistry Jun. 5, 1986; 261, 7426-7432.
Lepenies et al., "Targeting C-type lectin receptors with multivalent carbohydrate ligands." Adv. Drug Deliv. Rev. (2013).
Li et al., "Targeting self- and foreign antigens to dendritic cells via DC-ASGPR generates IL-10pproducing suppressive CD4+ T cells," Jan. 2, 2012, Journal of Experimental Medicine 209, 109-121 (2012).
Liu et al. "Hapten may play an important role in food allergen-related intestinal immune inflammation," North American Journal of Medical Sciences, vol. 3. No. 3. (Mar. 2011).
Liu et al., "Immune tolerance after delivery of dying cells to dendritic cells in situ," Journal of Experimental Medicine, vol. 196(8): 1091-1097 (Oct. 21, 2002).
Liu et al., "Functional Nucleic Acid Sensors", Chemical Reviews, 109(5):1948-1998, (May 2009).
Lobst et al., "Selective Sugar Binding to the Carbohydrate Recognition Domains of the Rat Hepatic and Macrophage Asialoglycoprotein Receptors." The Journal of Biological Chemistry, vol. 271, No. 12, Issue Mar. 22, 1996, 6686-6693.
Loma et al., "Multiple Sclerosis: Pathogenesis and Treatment" Department of Neurology, Curr. NeuropharmacOLOGY, 9:409-416, Year 2011.
Lorentz et al., "Engineered binding to erythrocytes induces immunological tolerance to E. coli asparaginase." Sci. Adv. 2015, 2015;1:e1500112, 10 pages.
Luo et al., "ECDI-fixed allogeneic splenocytes induce donor-specific tolerance for long-term survival of islet transplants via two distinct mechanisms," Proceedings of National Academy of Science, vol. 105(38):14527-14532 (Sep. 23, 2008).
Lutolf et al., "Synthesis and Physicochemical Characterization of End-Linked Poly(ethylene glycol)-co-peptide Hydrogels Formed by Michael-Type Addition," Biomacromolecules, 4:713-722, (Feb. 1, 2003).
Lutolf et al., "Systematic modulation of Michael-type reactivity of thiols through the use of charged amino acids," Bioconjugate Chemistry vol. 12(6):1051-1056 (2001).
Lutterotti, A. et al., "Antigen-Specific Tolerance by Autologous Myelin Peptide-Coupled Cells: A Phase 1 Trial in Multiple Sclerosis," Science Translational Medicine 5, 188ra75-188ra75 (2013).
Magnani et al., "Red blood cells as an antigen-delivery system," Biotechnol Appl Biochem. Oct. 1992; 16(2):188-94.
Maluccio et al., "Transcatheter arterial embolization with only particles for the treatment of unresectable hepatocellular carcinoma-" Journal of Vascular and Interventional Radiology, vol. 19(6):862-869 (2008).
Mamidyala, S. et al., "Glycomimetic ligands for the human asialoglycoprotein receptor" J. Am Chem. Soc. Feb. 1, 2012, 134(4), pp. 1978-1981.
Martini, S., Nielsen, M., Peters, B. et al. The Immune Epitope Database and Analysis Resource Program 2003-2018: reflections and outlook. Immunogenetics 72, 57-76 (2020).
Maynard et al., "Antibody engineering," Annual Review of Biomedical Engineering, vol. 2:339-376 (2000).
Meager et al., "Anti-cytokine autoantibodies in autoimmunity: preponderance of neutralizing autoantibodies against interferon-alpha, interferon-omega and interleukin-12 in patients with thymoma and or myasthenia gravis" Clinical and Experimental Immunology, Wiley-Blackwell Publishing Ltd, GB, vol. 132, No. 1, Apr. 1, 2003.
Medina et al., "Targeting hepatic cancer cells with pegylated dendrimers displaying N-acetylgalactosamine and SP94 peptide ligands" Advanced Healthcare Materials, vol. 2, Issue 10, pp. 1337-1350, Oct. 2013.
Meyer et al. Metformin and Insulin in Type 1 Diabetes; Diabetes Care 26:1655-1656, Year: 2003.
Miller et al., "Antigen-specific tolerance strategies for the prevention and treatment of autoimmune disease," Nature Reviews Immunology 7(9):665-677, (Sep. 2007).

(56) References Cited

OTHER PUBLICATIONS

Mitea, C. et al., "A Universal Approach to Eliminate Antigenic Properties of Alpha-Gliadin Peptides in Celiac Disease." PLoS One, vol. 5, Issue 12, e15637, pp. 1-9, Dec. 2010.
Moad et al., "Mechanism and Kinetics of Dithiobenzoate-Mediated RAFT Polymerization—Status of the Dilemma." Macromolecular Journals Chem. Phys. 2014, 215: 9-26.
Moghimi et al., "Stealth liposomes and long circulating nanoparticles: critical issues in pharmacokinetics, opsonization and protein-binding properties," Progress in Lipid Research, vol. 42(6):463-478 (2003).
Mohandas et al., "Red cell membrane: past, present, and future," Blood, vol. 112(10):3939-3948 (Nov. 15, 2008).
Moreau et al., "PEPOP: Computational design of immunogenic peptides" BioMed Central, Jan. 30, 2008, 15 pages.
Moss et al. "Glossary of Class Names of Organic Compounds and Reactive Intermediates Based on Structure", Pure & Appl. Chem., vol. 67, Nos. 819, pp. 1307-1375, 1995 (Year: 1995).
Mueller, "Mechanisms maintaining peripheral tolerance," Nature Immunology, vol. 11(1 ):21-27 (Jan. 2010).
Murphy, "Antigen Recognition by B-Cell and T-cell Receptors," 2012, Janeway's Immuno Biology, 8th Edition, Chapter 4, Garland Science Taylor & Francis Goup, London and New York.
Murray et al. "The Mouse Immune Response to Carrier Erythrocyte Entrapped Antigens," Vaccine, 24:6129-6139, (2006).
Muzykantov, "Drug Delivery by Red Blood Cells: Vascular Carriers Designed by Mother Nature", Expert Opinion Drug Delivery, 7(4 ):403-427, (Apr. 2010).
Nakayama, et al., "Determining Antigen Specificity of Human Islet Infiltrating T Cells in Type 1 Diabetes", Frontiers in Immunology, Mar. 8, 2019, vol. 10, pp. 1-7.
Nardin et al., "How are immune complexes bound to the primate erythrocyte complement receptor transferred to acceptor phagocytic cells," *Mol. Immunol.* 1999, 36, 827-835.
Nishikawa et al. "Galactosylated proteins are recognized by the liver according to the surface density of galactose moieties" The American journal of physiology Jun. 1995; 268(5 Pt 1):G849-56, Abstract.
O'Neil et al., "Extracellular matrix binding mixed micelles for drug delivery applications," Journal of Control Release, vol. 137(2):146-151, (Mar. 27, 2009).
Parmeggiani et al., "Designed armadillo repeat proteins as general peptide-binding scaffolds: consensus design and computational optimization of the hydrophobic core," Journal of Molecular Biology, vol. 376(5):1282-1304 (2008).
Pasut et al., "PEG conjugates in clinical development oruse as anticancer agents: An overview," Advanced Drug Delivery Reviews, vol. 61(13):1177-1188 (2009).
Qin et al., "Galactosylated N-2-Hydroxypropyl Methacrylamide-b-N-3-Guanidinopropyl Methacrylamide Block Copolymers as Hepatocyte-Targeting Gene Carriers," Bioconjugate Chem. 22:1503-1512 (2011).
Qin, et al., Preparation and bioactivity of anti-hum red blood cell ScFv and CSFV E@ bifunctional fusion protein, Chin J. Biotech 2010, Jan. 25: 26(1): 28-34, Chinese Journal of Biotechnology (2010).
Rajpal, Arvind, et al. "A general method for greatly improving the affinity of antibodies by using combinatorial libraries", PNAS, www.pnas.org/cgi/doi/10.1073/pnas.0503543102, vol. 102 No. 24, pp. 8466-8471, Jun. 14, 2005.
Reddy et al., "Exploiting lymphatic transport and complement activation in nanoparticle vaccines," Nature Biotechnology, vol. 25(10):1159-1164 (Oct. 2007).
Reddy et al., "In vivo targeting of dendritic cells in lymph nodes with poly(propylene sulfide) nanoparticles," Journal of Controlled Release, vol. 112(1):26-34, (Mar. 10, 2006).
Reinagel et al., "The Primate Erythrocyte Complement Receptor (CR1) as a Priveleged Site: Binding of Immunoglobulin G to Erythrocyte CR1 Does Not Target Erythrocytes for Phagocytosis," 1997, Blood, vol. 89: p. 1068-1077.
Rice et al., "Directed evolution of a biterminal bacterial display scaffold enhances the display of diverse peptides," Protein Engineering, Design & Selection, vol. 21(7):435-442 (2008).
Rigopoulou et al., "Asialoglycoprotein receptor (ASGPR) as target autoantigen in liver autoimmunity: Lost and found," Autoimmunity Reviews, 12 (2012) 260-269.
Rockey et al., "Synthesis and radiolabeling of chelator-RNA aptamerbioconjugates with copper-64 for targeted molecular imaging-" Bioorganic & Medicinal Chemistry, vol. 19(13):4080-4090 (2011).
Ruoslahti et al., "Targeting of drugs and nanoparticles to tumors," Journal of Cell Biology, vol. 188(6):759-768 (2010).
Rybak et al., "The extra-domain A of fibronectin is a vascular marker of solid tumors and metastases," Cancer Research, vol. 67(22):10948-10957 (2007).
Saibeni et al., "Antibodies to tissue-type plasminogen activator (t-PA) in patients with inflammatory bowel disease: high prevalence, interactions with functional domains of t-PA and possible implications in thrombosis," J. Thrombosis and Haemostasis, 4:1510-1516 (2006).
Saint-Lu, N. et al., "Targeting the allergen to oral dendritic cells with mucoadhesive chitosan particles enhances tolerance induction," Allergy, vol. 64(7):1003-1013 (2009).
Sakaguchi et al., "Regulatory T Cells and Immune Tolerance," Cell 133, May 30, 2008, 775-787.
Sampson, "Aptamers and SELEX: the technology," World Patent Information, vol. (25):123-129 (2003).
Savla et al., "Tumor targeted quantum dot-mucin 1 aptamer-doxorubicin conjugate for imaging and treatment of cancer," Journal of Controlled Release, vol. 153(1):16-22, Feb. 20, 2011.
Schliemann et al., "In vivo biotinylation of the vasculature in B-cell lymphoma identifies BST-2 as a target for antibody-based therapy," Vascular Blood, vol. 115(3):736-744 (Jan. 21, 2010).
Seamons et al. Immune Tolerance to Myelin Proteins (Immunologic Research 2003; 28/3:201-221).
Sehon et al., "Conversion of Antigens to Tolerogenic Derivatives by Conjugation with Monomethoxypolyethylene Glycol", The Pharmacology and Toxicology of Proteins, pp. 205-219 (1987).
Sehon et al., The Pharmacology and Toxicology of Proteins, Proceedings of Cetus—UCLA Symposium Held at Lake Tahoe, Ca, Feb. 21-28, 1987, Alan r. Liss, Inc.—New York.
Seymour et al., "Hepatic Drug Targeting: Phase I evaluation of polymer-bound doxorubicin" Journal of Clinical Oncology, vol. 20, No. 6, Mar. 15, 2002, pp. 1668-1676.
Seymour et al., "N-(2-Hydroxypropyl)methacrylamide copolymers targeted to the hepatocyte galactose-receptor: pharmacokinetics in DBA2 mice." Br. J. Cancer (1991) 63, pp. 859-866.
Shan et al., "Structural Basis for Gluten Intolerance in Celiac Sprue," Science, 297, 2275 (2002).
Shen "A galactosamine-mediated drug delivery carrier for targeted liver cancer therapy" Pharmacological Research 64 (2011) 410-419.
Sheridan "Fresh from the biologic pipeline-2009," Nature Biotechnology, vol. 28(4):307-310 (Apr. 2010).
Sigma-Aldrich, "RAFT Agents," available online at https://www.sigmaaldrich.com/materials-science/material-science-products.html?TablePage=103936134, 4 pages (accessed on Sep. 21, 2020) (Year: 2020).
Silverman et al., "Engineered cystine-knot peptides that bind vβ3 integrin with antibody-like affinities," Journal of Molecular Biology, vol. 382(4):1064-1075 (Jan. 30, 2009).
Sørensen et al., "Role of sialic acid for platelet life span: exposure of β-galactose results in the rapid clearance of platelets from the circulation by asialoglycoprotein receptor-expressing liver macrophages and hepatocytes." Blood, Aug. 20, 2009. vol. 114, No. 8.
Spitzer et al., "ScFv-Mediated in Vivo Targeting of DAF to Erythrocytes Inhibits Lysis by Complement," Molecular Immunology, vol. 40:911-919 (Oct. 30, 2003).
St. Clair et al., "New Reagents on the Horizon for Immune Tolerance," Sep. 20, 2006, Annu. Rev. Med. 2007. 58:329-46.
Staud et al., "Liver uptake and hepato-biliary transfer of galactosylated proteins in rats are determined by the extent of galactosylation" Biochimica et Biophysica Acta May 1999; 1427(2):183-192, Abstract.

(56) References Cited

OTHER PUBLICATIONS

Steiner et al., "Efficient selection of DARPins with sub-nanomolar affinities using SRP phage display," Journal of Molecular Biology, vol. 382(5):1211-1227 (2008).
Stern et al., "Promoting Tolerance to Proteolipid protein-induced experimental autoimmune encephalomyelitis through targeting dendritic cells," Proc. Natl. Acad. Sci. (PNAS) vol. 107: 17280-17285, (Oct. 2010).
Sun, et al., "Comparison between Ovalbumin and Ovalbumin Peptide 323-339 Responses in Allergic Mice: Humoral and Celluler Aspects," Scandinavian Journal of Immunology, vol. 71: 329-335 (Jan. 2010).
Supplementary European Search Report from corresponding PCT Application No. PCT/US2011047078, 21 Pages, Dated Jan. 22, 2014.
Taneja et al., "Lessons from animal models for human autoimmune diseases," Sep. 1, 2001, Nature Immunology, vol. 2, No. 9, 781-784 (Sep. 2001).
Taylor et al., "Anti-glycophorin single-chain Fv fusion to low-affinity mutant erythropoietin improves red blood cell-lineage specificity", Protein Engineering, Design & Selection, vol. 23, No. 4 pp. 251-260, 2010.
Teitelbaum et al., Immunomodulation of experimental autoimmune encephalomyelitis by oral administration of copolymer 1. Pro. Natl. Acad. Sci. USA vol. 96, pp. 3842-3847, Mar. 1999.
Thijssen et al., "Galectin-1 is essential in tumor angiogenesis and is a target for antiangiogenesis therapy-", Proceeding of the National Academy Sciences, vol. 103(43):15975-15980 (2006).
Thomson et al., "Antigen-presenting cell function in the tolerogenic liver environment," National Reviews Immunology, vol. 10(11):753-766 (Nov. 2010).
Tobio et al., "Stealth PLA-PEG Nanoparticles as Protein Carriers for Nasal Administration," Pharmaceutical Research, 15(2):270-275, (1998).
Trahtenherts, A. et al., "An internalizing antibody specific for the human asialoglycoprotein receptor" Hybridoma, vol. 28, No. 4, Aug. 1, 2009.
Turley et al., "Prospects for Antigen-Specific Tolerance Based Therapies for the Treatment of Multiple Selerosis," Results and Problems in Cell Differentiation, 51 :217-235, (2010).
Tye-Din, et al. "Comprehensive, Quantitive Mapping of T Cell Epitopes in Gluten in Celiac Disease", www.Science TranslationalMedicine.org, Jul. 21, 2010, vol. 2 Issue 41, in 14 pages.
Updike et al., "Infusion of red blood cell-loaded asparaginase in monkey: Immunologic, metabolic, and toxicologic consequences," 1983, J Lab Clin Med, vol. 101(5): p. 679-691.
Van Der Vlies et al., "Synthesis of pyridyl disulfide-functionalized nanoparticles for conjugating thiol-containing small molecules, peptides, and proteins," Bioconjugate Chemistry, vol. 21(4):653-662 (2010).
Velluto et al., "PEG-b-PPS Diblock Copolymer Aggregates for Hydrophobic Drug Solubilization and Release: Cyclosporin A as an Example," Molecular Pharmaceutics, 11 Pages, (May 2, 2008).
Vogl et al., "Review on transarterial chemoembolization in hepatocellular carcinoma: Palliative, combined, neoadjuvant, bridging, and symptomatic indications," European Journal Radiology, vol. 72(3):505-516 (2009).
Walker et al., "Anti-serum albumin domain antibodies in the development of highly potent, efficacious and long-acting interferon," Protein Engineering Design & Selection, vol. 23(4):271-278 (2010).
Wan, "Regulatory T cells: immune suppression and beyond," May 1, 2010, Cell Mol Immunol. May 2010; 7(3):204-210.
Wang et al in "Diagnostic imaging and therapeutic application of nanoparticles targeting the liver"; J. Mater. Chem. B, 2015, 3, 939. (Year: 2015).
Wang et al., "Synthesis and Micellization of Thermoresponsive Galactose-Based Diblock Copolymers," J Polymer Sci. 49:3280-3290 (2011).
Weisser et al., "Applications of single-chain variable fragment antibodies in therapeutics and diagnostics," Biotechnology Advances, vol. 27(4):502-520 (2009).
Wilcock, H. et al. "End Group Removal and Modification of RAFT polymers," Polymer Chemistry, vol. 1, Jan. 1, 2010, pp. 149-157.
Wilson et al., "Rapid Whole Blood Assay for HIV-1 Seropositivity Using an Fab-Peptide Conjugate," Journal of Immunological Methods, vol. 138:111-119 (1991).
Wilson, D.B., "Kent et al. Replying to: D.B. Wilson", Nature, 438, 2005.
Wu, Herren, "Simultaneous Humanization and Affinity Optimization of Monoclonal Antibodies", Methods in Molecular Biology, vo. 207: Recombinant Antibodies for Cancer Therapy: Methods and Protocols, Tolowa, NJ, pp. 197-212, Jan. 1, 2003.
Yamazaki et al., "CD8+ CD205+ splenic dendritic cells are specialized to induce Foxp3+ regulatory T cells," Journal of Immunology, vol. 181(10):6923-6933 (2008).
Yeste Ada et al: "Antigen Microarrays for the Study of Autoimmune Diseases", Clinical Chemistry, vol. 59, No. 7, Jul. 2013 (Jul. 2013), pp. 1036-1044, ISSN: 0009-9147(print).
Yoo et al., "N-Acetylgalactosamino dendrons as clearing agents to enhance liver targeting of model antibody-fusion protein." Bioconjugate Chemistry, vol. 24, No. 12, Dec. 18, 2013, pp. 2088-2103.
Zaitsev et al., "Targeting of a Mutant Plasminogen Activator to Circulating Red Blood Cells for Prophylactic Fibrinolysis", The Journal of Pharmacology and Experimental Therapeutics, 332(3):1022-1031 and 976 (Nov. 30, 2009).
Zhao, X. et al "Construction and characterization of an anti-asialoglycoprotein receptor single-chain variable-fragment-targeted melittin" Biotechnology and Applied Biochemistry, Nov.-Dec. 2011; 58(6): pp. 405-411.
Zhong et al., "Ligand-directed Reduction-Sensitive Shell-Sheddable Biodegradable Micelles Actively Deliver Doxorubicin into the Nuclei of Target Cancer Cells," Biomacromalecules 14:3723-3730 (2013).
English translation of Office Communication issued in Japanese Patent Application No. 2020-563514, dated Feb. 7, 2024.
Li et al., "Shape Effect of Glyco-Nanoparticles on Macrophage Cellular Uptake and Immune Response," ACS Macro Letters, 5(9):1059-1064, 2016.
Brunggel, K. L., Introducing tolerance to foreign and partly foreign proteins by erythrocyte binding and artificial glycosylations. 2018. Ecole Polytecnique Federale de Lausanne, Thesis 8190.
Office Action issued in Corresponding Singapore Application No. 11202011078V, dated Jun. 30, 2022.
International Search Report and Written Opinion issued in Corresponding PCT Application No. PCT/US2019/31440, dated Sep. 13, 2019.
Office Action issued in corresponding Japanese Application No. 2020563514 dated Jun. 19, 2023.
English translation of Office Communication issued in Chinese Patent Application No. 201980045533.2, dated Nov. 8, 2024.
Chungsong et al., "Bioconjugate Strategies for the Induction of Antogen-Specific Tolerance in Autoimmune Diseases," Bioconjug. Chem., 29(3):719-732, 2018.
Schuette et al., "Mannose receptor induces T-cell tolerance via inhibition of CD45 and up-regulation of CTLA-4," PNAS, 113(38):10649-10654, 2016.

* cited by examiner

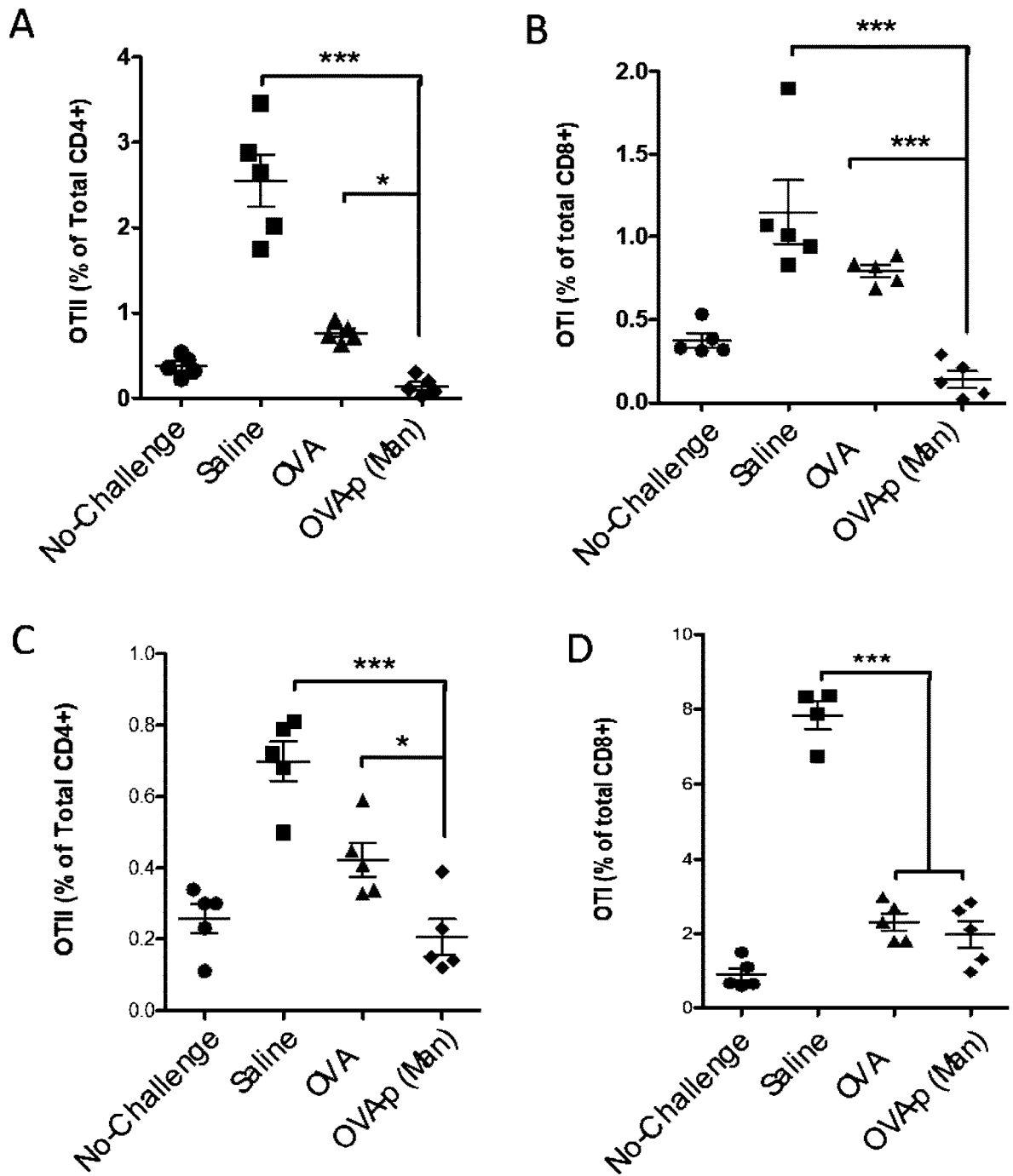
FIG. 1A-D

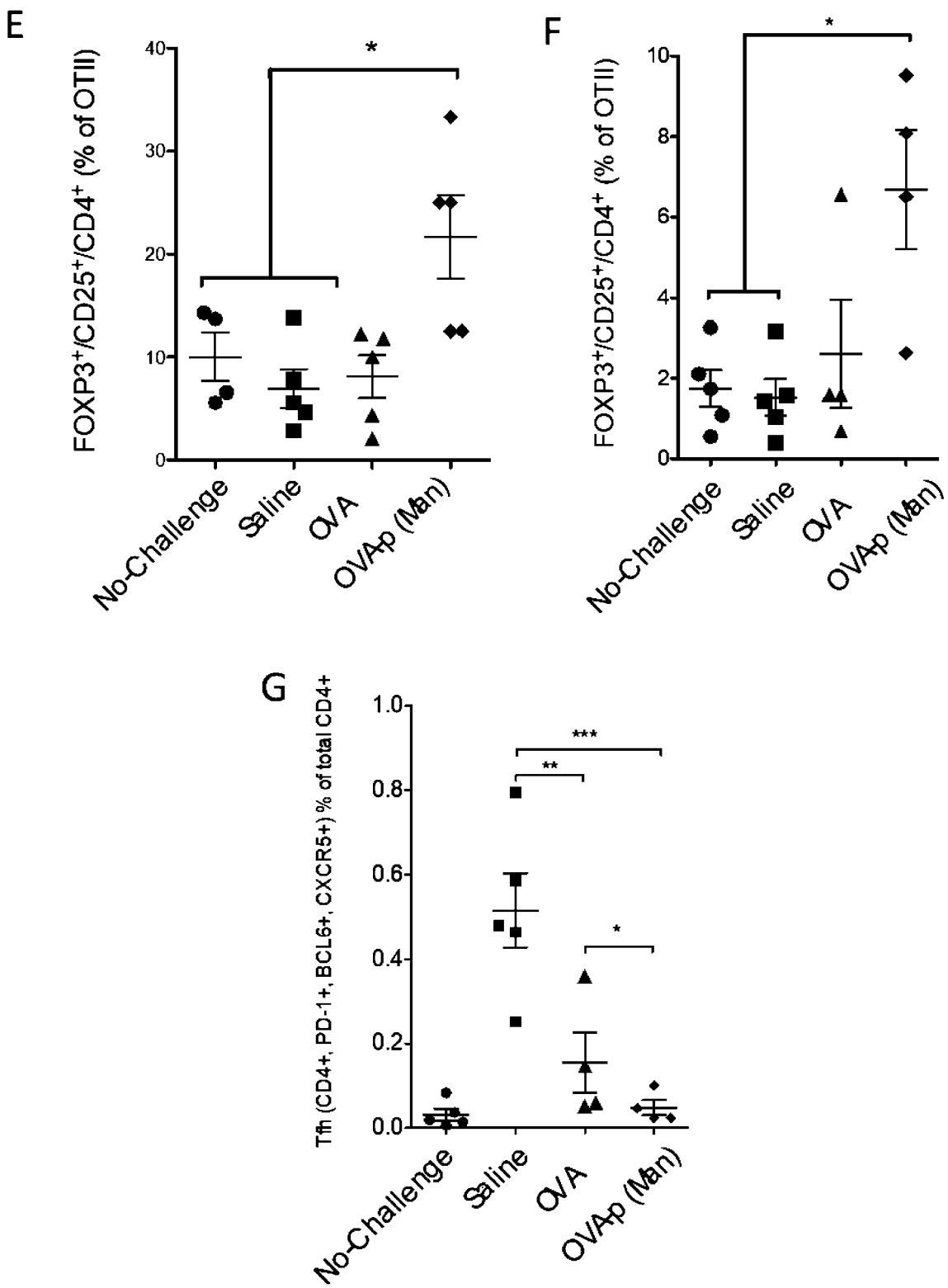
FIG. 1E-G

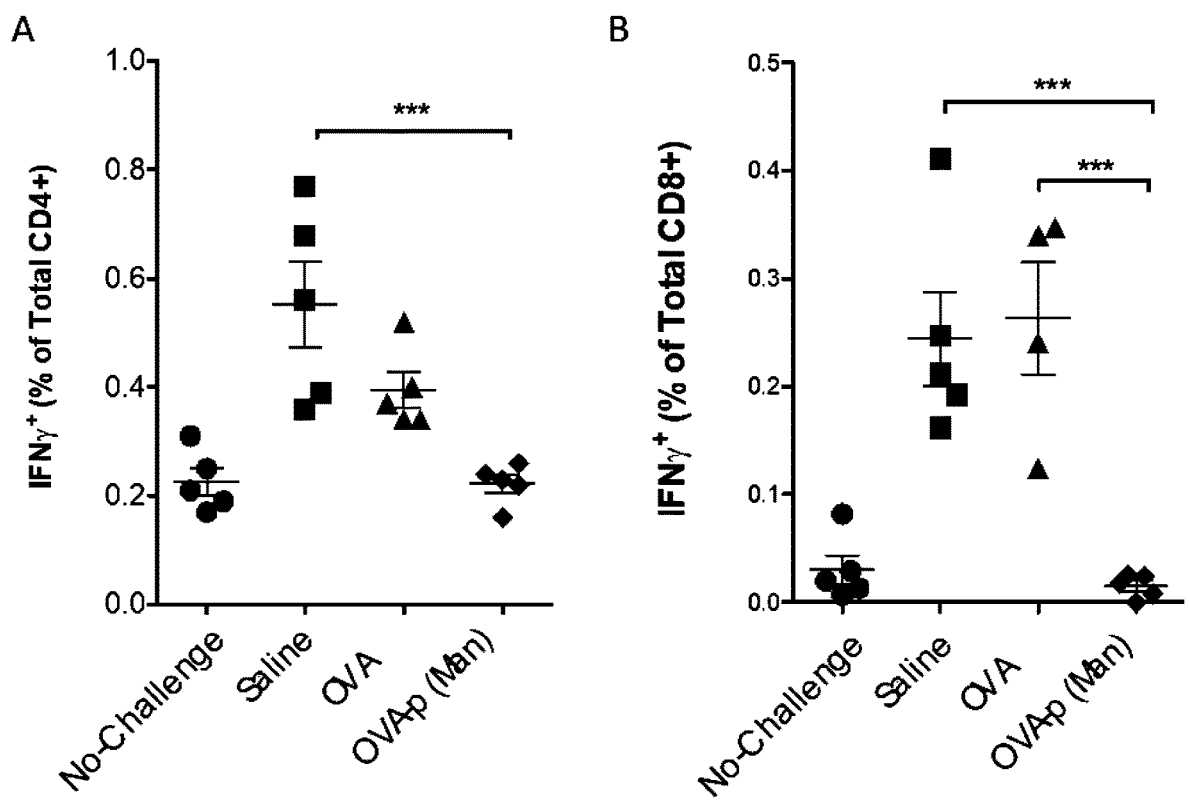
FIG. 2A-B

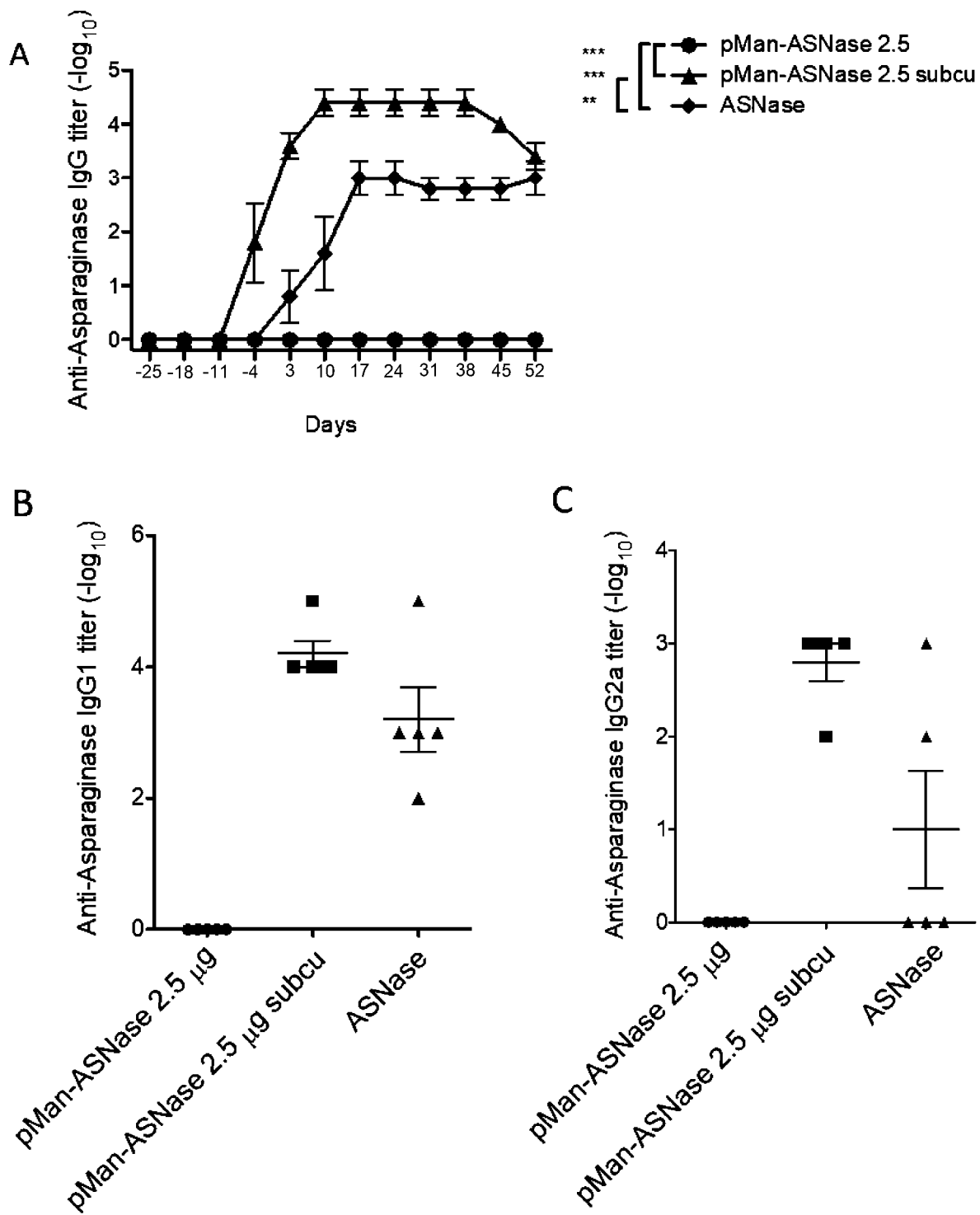
FIG. 3A-C

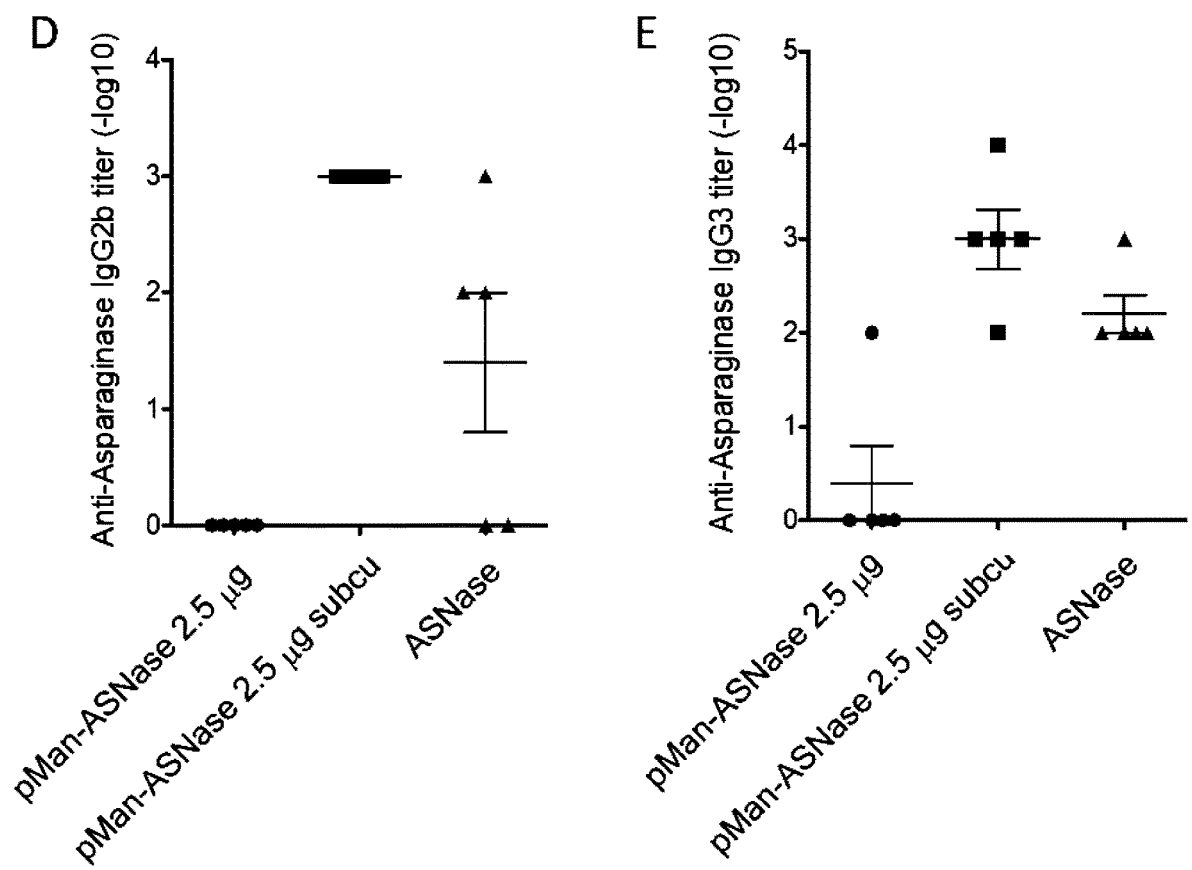
FIG. 3D-E

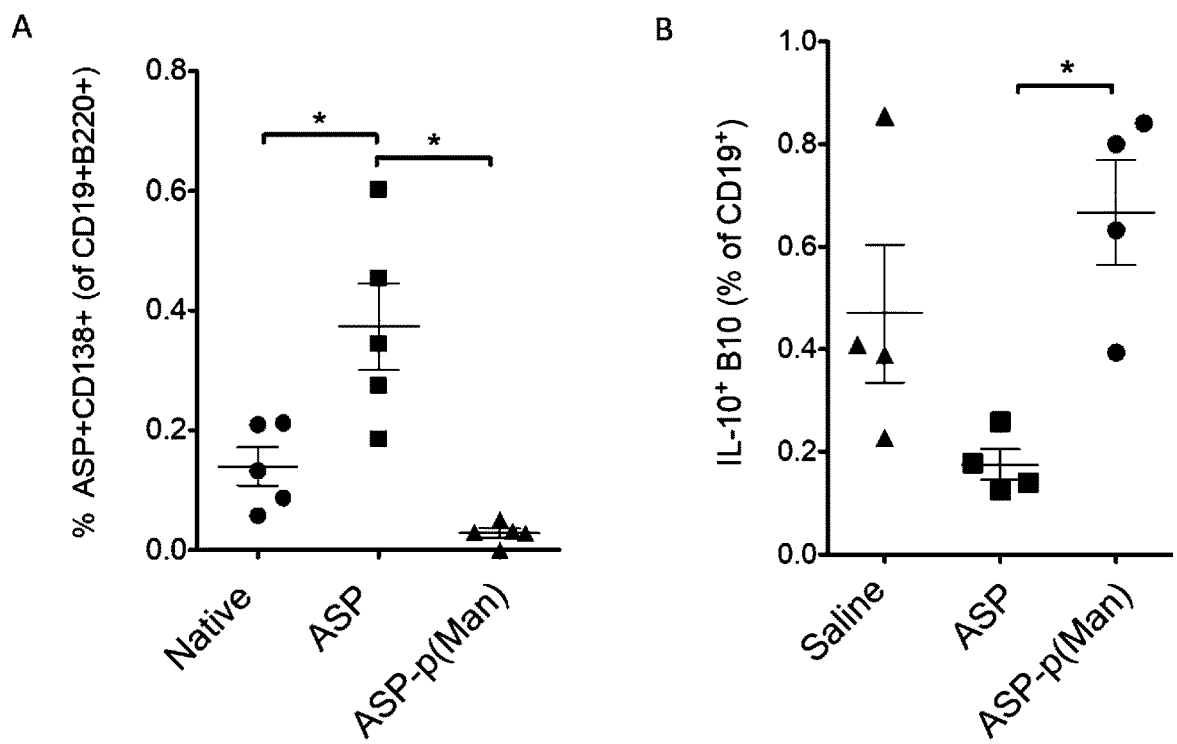
FIG. 4A-B
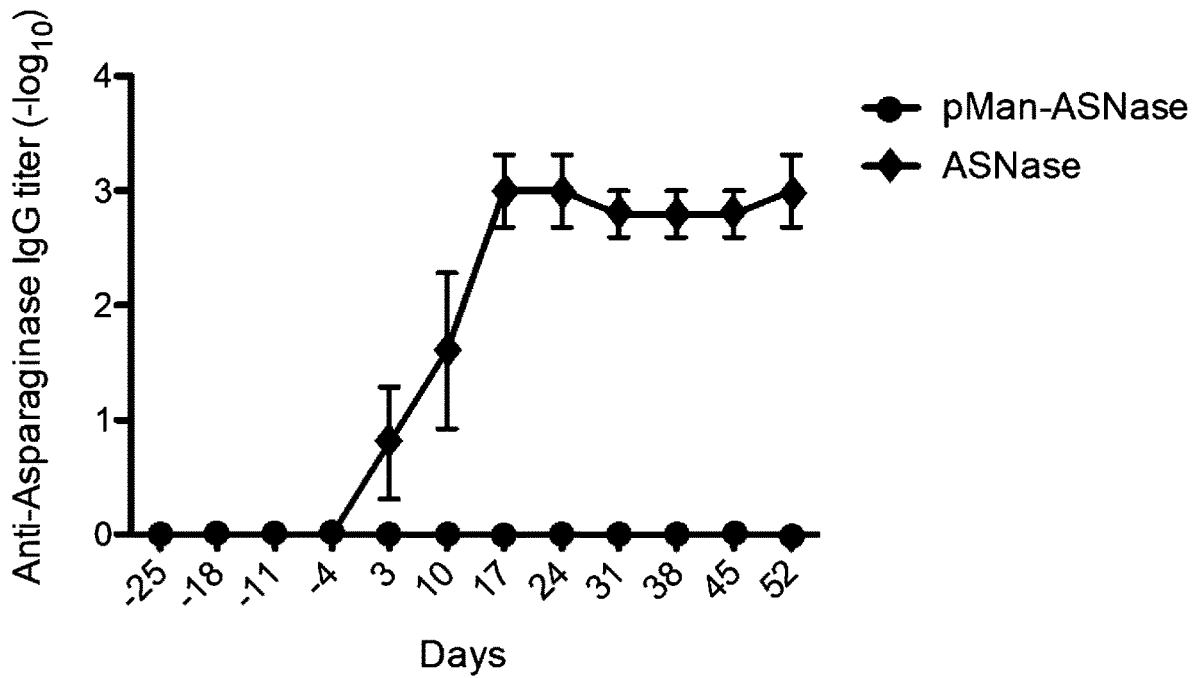
FIG. 5

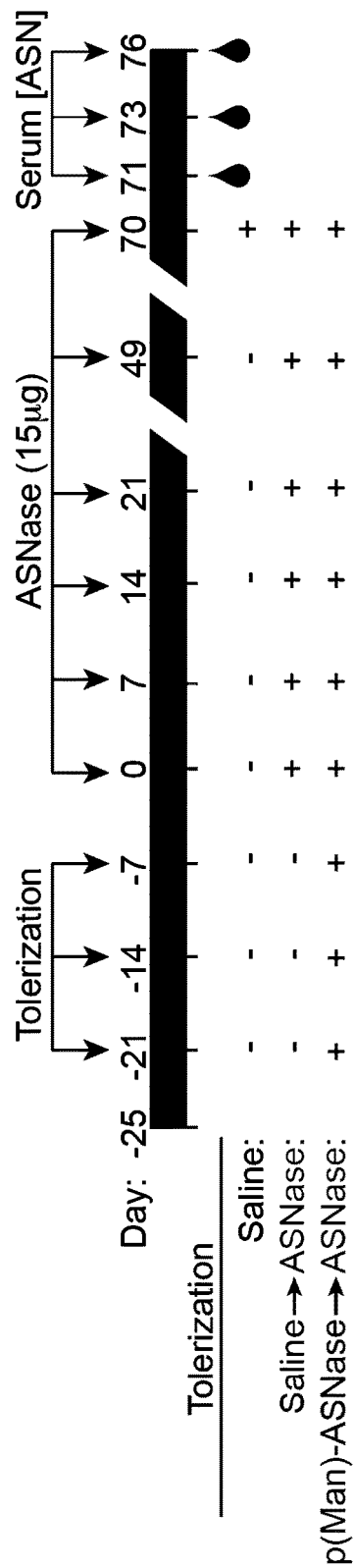
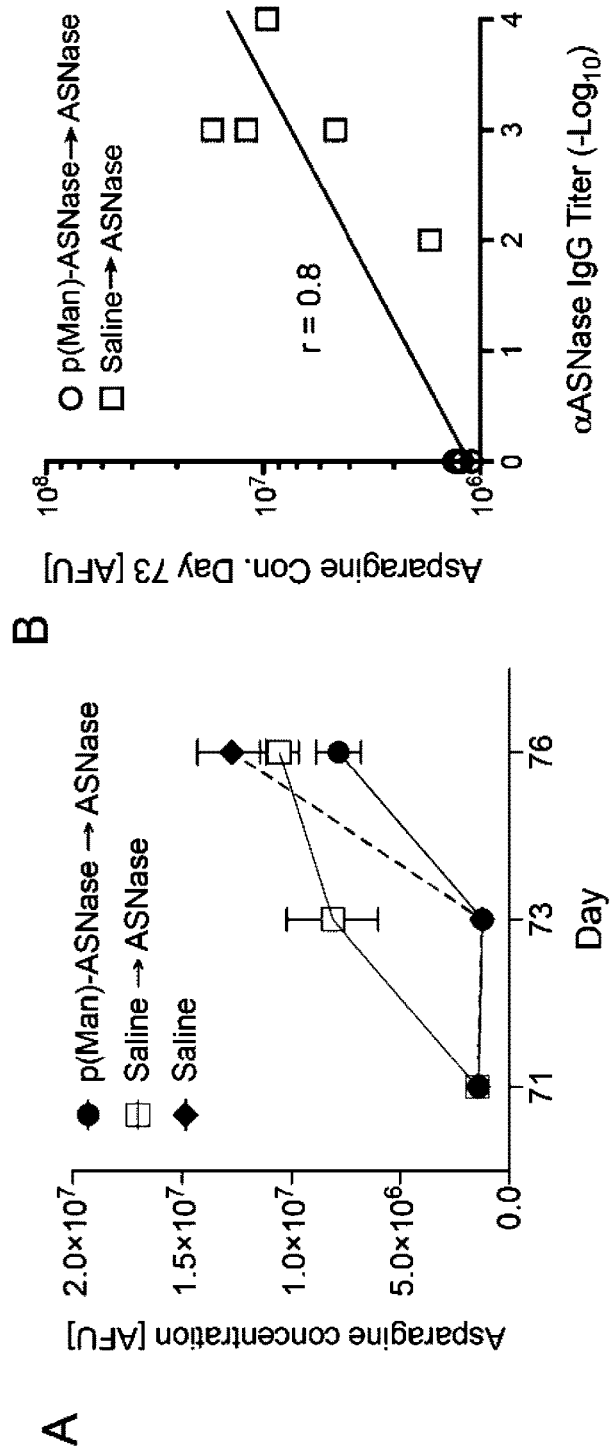
FIG. 6
FIG. 7A-B

COMPOSITIONS AND METHODS CONCERNING IMMUNE TOLERANCE

CROSS-REFERENCE TO RELATED APPLICATIONS

This application is a national phase application under 35 U.S.C. § 371 of International Application No. PCT/US2019/031440 filed May 9, 2019, which claims priority to U.S. Provisional Patent Application No. 62/669,044, filed May 9, 2018, all of which are incorporated in their entirety by reference.

BACKGROUND OF THE INVENTION

1. Field

Embodiments of the present invention relate generally to the fields of organic chemistry, biochemistry, and immunology.

2. Background

Small molecules, e.g., non-peptide or nucleic acid-based molecules having a molecular weight of less than 500 Daltons, have historically dominated the FDA's new molecular entity (NME) approvals. Since the FDA's approval of insulin as the first drug produced by recombinant DNA technology in 1982, protein-based drug approvals have experienced an upward trend, as demonstrated by the almost yearly increase in FDA biologics license application (BLA) approvals in the last 23 years.

A primary difference between a small molecule drug and a protein-based drug lies in the ability of antigen presenting cells to take up proteins, including protein-based drugs, process them, and present them as peptides to the major histocompatibility complex (MHC) class I and II to the immune system. Protein-based drugs are expressed and purified to be free of any pathogen-associated molecular patterns (PAMPs) and danger associated molecules (DAMPs). Notwithstanding the anti-immunogenic design of protein-based drugs, a significant portion of patients who are treated with these drugs develop antibodies against the drugs (anti-drug antibodies).

These and other examples demonstrate that protein-based drug immunogenicity can revert the effect of therapy for certain patients or even render a new approach to treat a disease inefficient. The negative effects provided by anti-drug antibodies highlight the need to develop a platform that allows clinicians induce tolerance to foreign and partly foreign proteins.

Technologies to induce antigen-specific immunological tolerance are still in their infancy, but are needed to prevent immunity to many protein-based drugs, to reverse immunity to allergens, and to prevent and reverse immunity to autoimmune antigens.

SUMMARY

A useful tolerogenic drug would consist of an antigen and a tolerance inducing component. The tolerance inducing component can be a chemical conjugated entity, part of a fusion protein, nanoparticles, or cells that are pulsed with the antigen. Ideally, a tolerance-inducing drug is based on the drug it tries to tolerize against, and can easily be modified.

Disclosed herein are compositions and methods for inducing tolerance towards therapeutic proteins, e.g., protein-based drugs. In some aspects, the present disclosure provides therapeutic, polymer-tethered antigens that include mannose monomers or derivatives thereof. In some embodiments, derivatives of mannose include optionally substituted mannose substituents. In several embodiments, the mannose derivative comprises a mannose with a phosphate at the C1, C2, C3, C4, C5, and/or C6 position. In several embodiments, the targeting moiety comprises mannose-6-phosphate. In some embodiments, compositions including a mannose or mannose-derived moiety induce tolerance to immunogenic protein-based therapeutics, delete antigen-specific CD4 and CD8 T cells, elevate levels of regulatory T cell responses and IL-10 producing Breg cells, and/or reduce antigen-specific plasma cells and memory B cells. The compositions disclosed herein may be targeted for delivery to antigen-presenting cells including, but not limited to, hepatocytes, LSECs, Kupffer cells, and stellate cells. In some aspects, the compositions disclosed herein exhibit affinity for and specifically bind to mannose-binding receptors.

In several embodiments, there are provided compounds, as well as compositions comprising such compounds, of Formula 1:

$$X—[Y(Z)_p]_m—R^2 \qquad \text{Formula 1}$$

where X comprises an antigen, a tolerogenic portion thereof, or a mimetic thereof, Y comprises a linker moiety, Z comprises a moiety that specifically targets a mannose receptor, p is an integer from about 2 to about 250, m is an integer from about 1 to about 100, and $R^2$ is any of functional groups I-III:

I

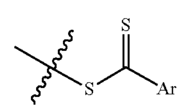

II

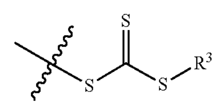

III where Ar is a substituted or unsubstituted aromatic group, where $R^3$ is any carbon-containing linear or heterocyclic moiety, and $R^{11}$ is hydrogen or an alkyl group.

In several embodiments, the moiety that specifically targets a mannose receptor is selected from the group consisting of α-linked mannose, β-linked mannose, substituted mannose, mannose-6-phosphate, N-acetyl mannosamine, and mannan having β(1-4), α(1-6), α(1-2), and/or α(1-3) linkages. In several embodiments, a plurality of these targeting moieties are used in combination in order to enhance targeting of and/or binding to the mannose receptor.

In several embodiments, Y is a linker resulting from reaction of at least one of a N-hydroxysuccinamidyl linker, maleimide linker, PEG linker, vinylsulfone linker, pyridyl di-thiol-poly(ethylene glycol) linker, pyridyl di-thiol linker, n-nitrophenyl carbonate linker, NHS-ester linker, and nitrophenoxy poly(ethylene glycol)ester linker. In some embodiments, Y is covalently bound to X.

Depending on the embodiment, the following portion of Formula 1 (—[Y(Z)p]-) is represented by one of Formula Ya to Yr:
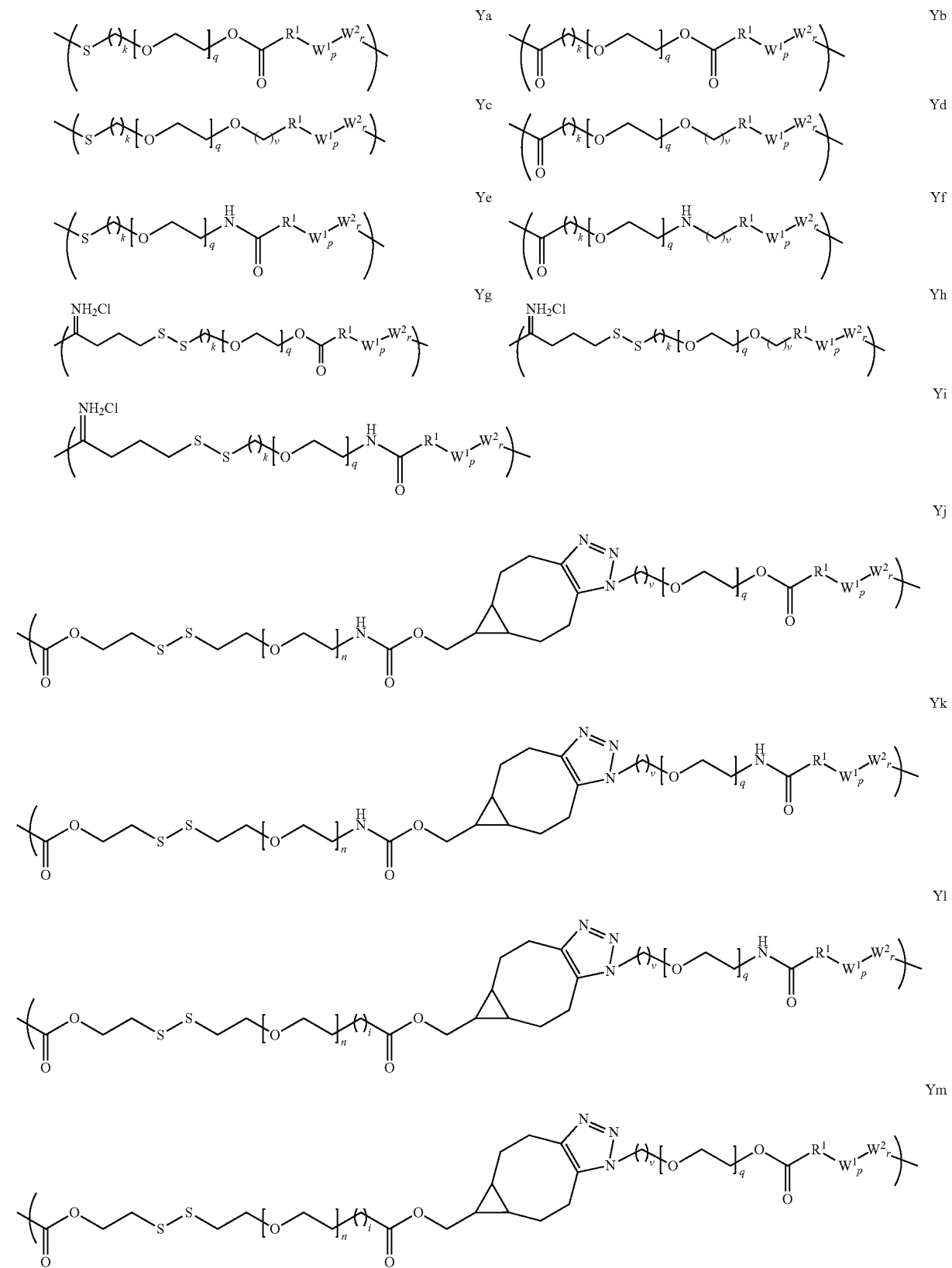

-continued

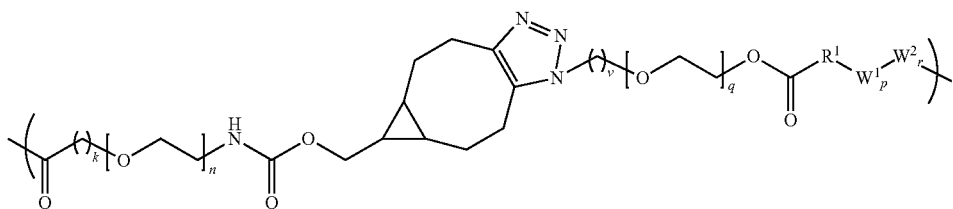
Yn

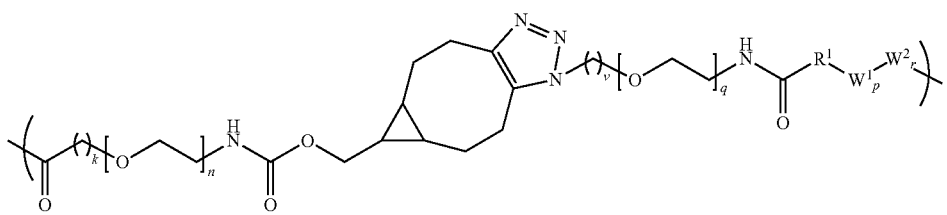
Yo

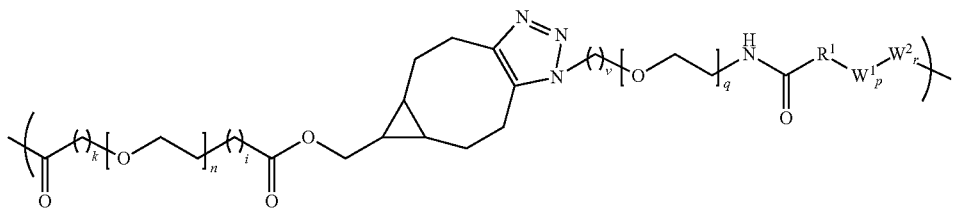
Yp

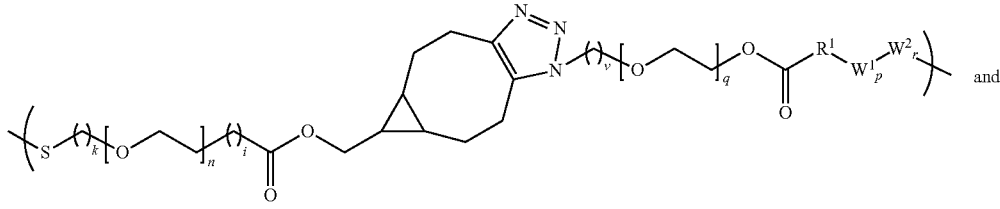
Yq and

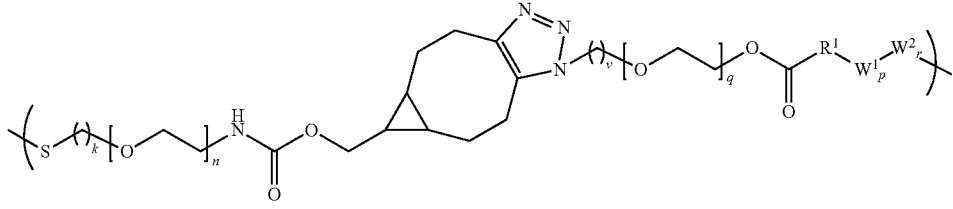
Yr where
n is an integer from about 1 to about 100;
q is an integer from about 1 to about 44;
k is an integer from about 1 to about 12;
i is an integer from 0 to about 20;
v is an integer from about 1 to about 4;
p is an integer from about 2 to about 250;
r is an integer from 0 to about 250;
$R_1$ is —$CH_2$—, —$(CH_2)_2$—C($CH_3$)(CN)—, —$(CH_2)_2$—C($CH_3$)($CH_3$)—, —$(CH_2)_2$—CH($CH_3$)— or —CH($CH_3$)—;
$W^1$ and $W^2$ are as defined below:

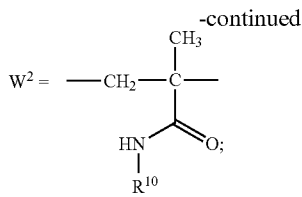

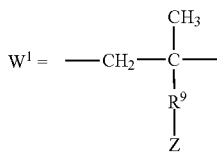

$R^9$ is a direct bond, —$(CH_2)_2$—NH—C(O)— (an ethylaceetamido group or "EtAcN") or —$(CH_2)_2$—(O—$CH_2$—$CH_2$)$_t$—NH—C(O)— (a pegylated ethylacetamido group or "Et-PEGt-AcN")
t is an integer from 1 to 5, Z is mannose or a mannose receptor-targeting moiety; and $R^{10}$ is an aliphatic group, an alcohol, an aliphatic amine-containing group, or an aliphatic alcohol.

In several embodiments, Y is an antibody, antibody fragment, peptide or other ligand that binds to X.

In several embodiments, X is an antigen against which a patient may develop or has developed an unwanted immune response. For example, depending on the embodiment, the antigen may be a foreign transplant antigen, an alloantigen, an autoimmune antigen, a food antigen, an animal antigen, a plant antigen, an environmental antigen, a therapeutic antigen, a synthetic self-antigen, or a tolerogenic (e.g., immunogenic, or capable of inducing an immune response) portion thereof. In several embodiments, X is an asparaginase antigen or an ovalbumin antigen. In several embodiments, the antigen is comprised in a vesicle, cell fragment, or cell.

In several embodiments, the antigen comprises at least one autoimmune antigen or tolerogenic portion thereof. In several embodiments, the at least one autoimmune antigen comprises at least one of an immunogenic fragment or fragments of myelin basic protein (MPB), an immunogenic fragment or fragments of myelin oligodendrocyte glycoprotein (MOG), an immunogenic fragment or fragments of myelin proteolipid protein (PLP), MBP, MOG, or PLP. In several embodiments, the at least one autoimmune antigen comprises at least one of SEQ ID Nos. 23-47. In several embodiments, the at least one autoimmune antigen comprises at least one of SEQ ID Nos. 24, 25, 27, 28, 31, 32, 33, 34, 35, 36, 43, 44, 45, 46, and 47. In some embodiments, the compound optionally further comprises at least one of SEQ ID NOs: 29, 38, 39, 40, 41, and 42. In several embodiments, such compounds are for use in treatment of or prevention of multiple sclerosis. In some embodiments, such compounds are administered for the use of preventing multiple sclerosis in a subject predicted to have multiple sclerosis. In some aspects, such compounds are administered to a subject presenting one or more symptoms of multiple sclerosis.

In several embodiments, the at least one autoimmune antigen comprises at least one of insulin, proinsulin, pre-proinsulin, glutamic acid decarboxylase-65 (GAD-65 or glutamate decarboxylase 2), GAD-67, glucose-6 phosphatase 2, islet-specific glucose 6 phosphatase catalytic subunit related protein (IGRP), insulinoma-associated protein 2 (IA-2), insulinoma-associated protein 2β (IA-2β), ICA69, ICA12 (SOX-13), carboxypeptidase H, Imogen 38, GLIMA 38, chromogranin-A, HSP-60, carboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, and SST G-protein coupled receptors 1-5, or an immunogenic fragment of any of these antigens. In several embodiments, the autoimmune antigen comprises an immunogenic fragment of proinsulin. Optionally an immunogenic fragment of IA-2, GAD-65, GAD-67, insulin, and/or IGRP is included. In several embodiments, the at least one autoimmune antigen comprises at least one of SEQ ID NOs: 1-19, or an immunogenic fragment of any of SEQ ID NOs: 1-19. In several embodiments, the at least one autoimmune antigen comprises at least one of SEQ ID NOs: 4-19. In several embodiments, such compounds are for use in the treatment or prevention of Type 1 Diabetes. In some embodiments, such compounds are administered for the use of preventing Type 1 Diabetes in a subject predicted to have Type 1 Diabetes. In some aspects, such compounds are administered to a subject presenting one or more symptoms of Type I Diabetes.

In several embodiments, the antigen comprises a food antigen, or a tolerogenic portion thereof. In several embodiments, the antigen comprises at least one of tissue transglutaminase, high molecular weight glutenin, low molecular weight glutenin, gluten, alpha-gliadin, gamma-gliadin, omega-gliadin, hordein, secalin, avenin, and deamidated forms thereof. In several embodiments, the antigen comprises a tolerogenic portion of at least one of tissue transglutaminase, high molecular weight glutenin, low molecular weight glutenin, gluten, alpha-gliadin, gamma-gliadin, omega-gliadin, hordein, secalin, avenin, and deamidated forms thereof. In several embodiments, the antigen comprises at least one of SEQ ID NOs. 54-61. In several embodiments, such compounds are for use in the treatment or prevention of Celiac Disease. In some embodiments, such compounds are administered for the use of preventing Celiac Disease in a subject predicted to have Celiac Disease. In some aspects, such compounds are administered to a subject presenting one or more symptoms of Celiac Disease.

In several embodiments, the mannose receptor is mannose-6-phosphate receptor. In several embodiments, Y and X are connected through a bond configured to cleave when the compound reaches a target area. Advantageously, this cleavage, in several embodiments, is triggered when the compound is at a target site (e.g., site where the mannose receptor is bound). This allows, in several embodiments, delivery of the free antigen to the target site.

In several embodiments, Ar is selected from:

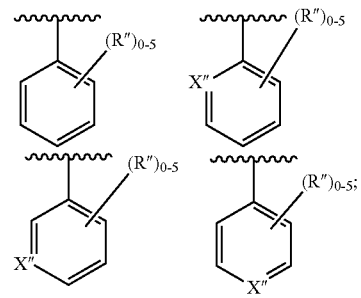

where each instance of R", when present, is independently selected from an optionally substituted C1-6-alkyl, optionally substituted C1-6 alkoxy, optionally substituted amino, OH, or halogen and wherein, X" is a heteroatom. In several embodiments, X" is N. In several embodiments, R11 is C1-6-alkyl. In several embodiments, R11 is —CH3. In several embodiments, R3 is C1-6-alkyl.

There are also provided herein, compositions comprising the compounds as described above, or elsewhere herein. Likewise, there are provided for herein uses of these compounds for inducing tolerance (or treating an unwanted immune response) to an antigen, a tolerogenic portion (or portions) of one or more antigens, and/or to mimetics of the antigens or portions of antigens. Also provided are uses of such compounds in the preparation of a medicament for inducing tolerance (or treating an unwanted immune response) to an antigen, a tolerogenic portion (or portions) of one or more antigens, and/or to mimetics of the antigens or portions of antigens.

Certain aspects of the disclosure are directed towards compositions comprising a compound of Formula 1:

$$X-[Y(Z)_p]_m-R^2 \qquad \text{Formula 1}$$

where X comprises an antigen or a tolerogenic portion thereof, Y comprises a linker moiety, Z comprises a moiety that specifically targets a mannose receptor, p is an integer from about 2 to about 250, m is an integer from about 1 to about 100, $R^2$ is any of functional groups I-III:

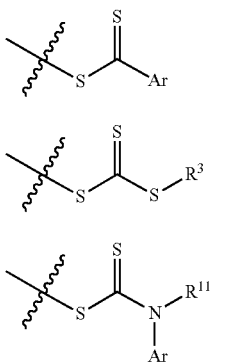

where Ar is a substituted or unsubstituted aromatic group, $R^3$ is any carbon-containing linear or heterocyclic moiety, and $R^{11}$ is hydrogen or an alkyl group. In some embodiments, $R^2$ comprises an end-capping group. In some embodiments, $R^2$ when disconnected from the construct, forms a stable or substantially stable free radical. In some embodiments, $R^2$ is a reversible addition-fragmentation chain transfer (RAFT) agent for a living polymerization. In some embodiments, $R^2$ can be reversibly added and removed to the construct to lengthen the linker region. In some embodiments, $R^2$ is a RAFT agent. In some embodiments, $R^2$ is not a RAFT agent. In some embodiments, $R^2$ is H or is absent. In some embodiments, $R^2$ is an optionally substituted dithiobenzoate, a trithiocarbonate, or a xanthate. In some embodiments, $R^3$ or $R^{11}$ may be hydrogen, optionally substituted alkyl, optionally substituted cycloalkyl, optionally substituted aryl, or optionally substituted heteroaryl. In some embodiments, $R^3$ is hydrogen, optionally substituted $C_6$-aryl, or $C_{1-6}$-alkyl (optionally substituted with halogen, or hydroxyl). In some embodiments, Ar as provided above is phenyl (optionally substituted with one or more OH groups, $NH_2$ groups, and/or halogens). In some embodiments, $R^2$ is one of the functional groups:

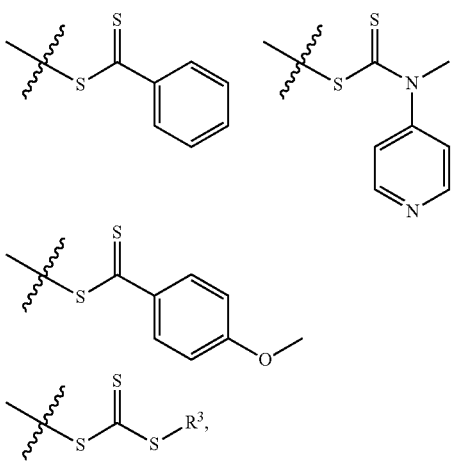

where $R^3$ is as defined above. In several embodiments, Ar in any of functional groups I or II is an optionally substituted $C_6$-$C_{14}$ aryl or an optionally substituted heteroaryl having 6 to 14 ring members of which 1-4 are heteroatoms. In several embodiments, the optionally substituted $C_6$-$C_{14}$ aryl is optionally substituted with one or more functional groups selected from $C_1$-$C_6$alkyl, amino, halogen, —OH, or combinations thereof. In several embodiments, Ar is selected from the group consisting of:

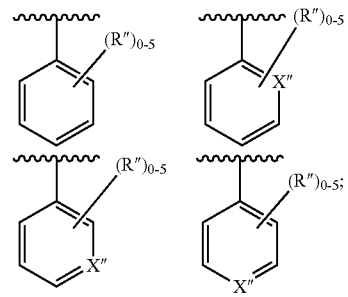

where each instance of R'', when present, is independently selected from an optionally substituted $C_{1-6}$-alkyl, optionally substituted $C_{1-6}$ alkoxy, optionally substituted amino, OH, or halogen. In several embodiments, X'' is a heteroatom. In several embodiments, X'' is N. In several embodiments, $R^{11}$ is $C_{1-6}$-alkyl. In several embodiments, $R^{11}$ is —$CH_3$. In several embodiments, $R^3$ is $C_{1-6}$-alkyl.

In some embodiments, Y and X are connected via a bond that cleaves or is configured to cleave at a target site for the compound. In several embodiments, Y and X are bonded through a disulfanyl ethyl ester or a disulfide bond. In several embodiments, the bond between Y and X is configured to cleave when the compound of Formula 1 reaches its biological target (e.g., the liver, liver cells, and/or the cytosol of cells in the liver) in a patient. In several embodiments, the Y—X bond cleaves in the presence of a cellular reducing agent (e.g., glutathione). In some embodiments, advantageously, once the bond between X and Y is cleaved, X is left in its native form and/or an active form. In some embodiments, once X is cleaved from Y, it is in a form that is more active than when bound to Y. In some embodiments, dithiol-containing compounds, particularly disulfanylethyl carbamate-containing links between X and Y (named including a free amine of X, otherwise named a "disulfanyl ethyl ester" without including the free amine of X) are advantageous as having the ability to cleave and release an antigen in its original form once inside a cell, for example as illustrated below (where Y' indicates the remaining portion of the linker and X and Z are as defined)

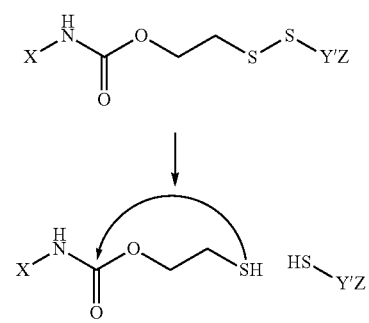

-continued

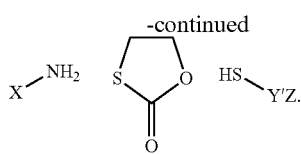

In several embodiments, the liver targeting moiety of the compound of Formula 1 is not galactose, galactosamine, N-acetylgalactosamine, glucose, glucoseamine and/or N-acetylglucosamine.

In some embodiments, Y is a linker. In several embodiments, Y is a reaction product resulting from one or more reactions involving at least one of the following: N-hydroxysuccinamidyl (NHS) linker, NHS ester linker, PEG linker, maleimide linker, vinylsulfone linker, pyridyl di-thiol-poly(ethylene glycol) linker, pyridyl di-thiol linker, n-nitrophenyl carbonate linker, or a nitrophenoxy poly(ethylene glycol)ester linker. The linker may have one or more mannose moieties or mannose receptor-targeting moieties bound to it. In several embodiments, Y comprises an antibody, an antibody fragment, a peptide, or a disulfanyl ethyl ester to which one or more mannose moieties or mannose receptor-targeting moieties are bound. In some aspects, —[Y(Z)$_p$]— is a group represented by one of Formula Ya to Yr:

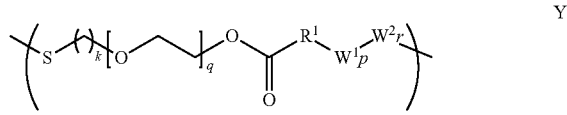 Ya

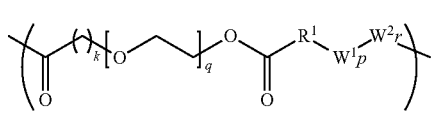 Yb

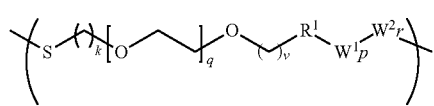 Yc

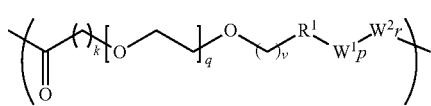 Yd

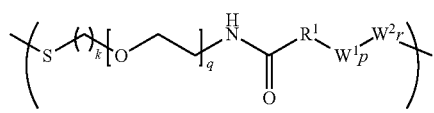 Ye

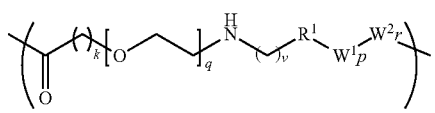 Yf

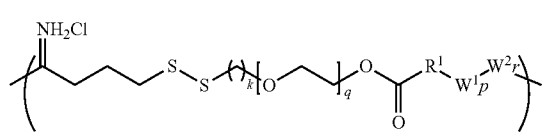 Yg

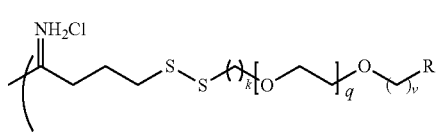 Yh

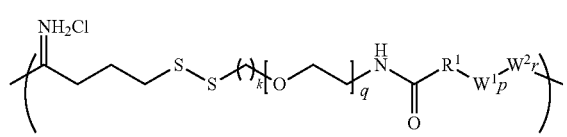 Yi

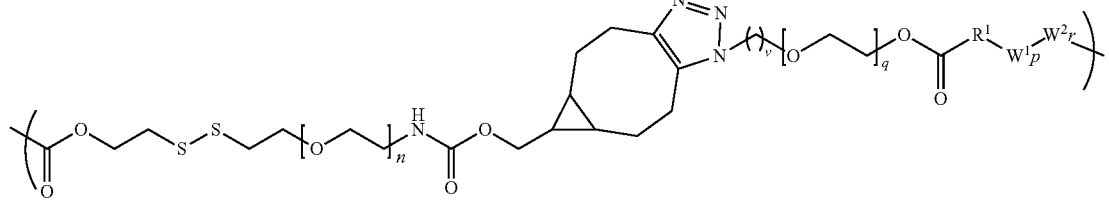 Yj

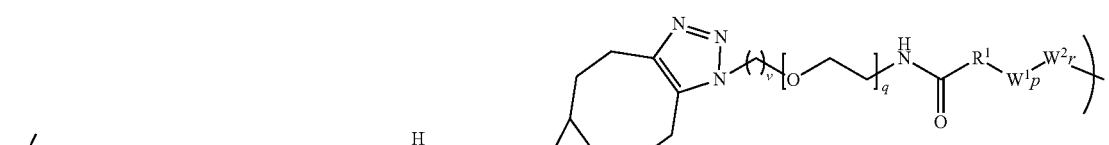 Yk

 Yl

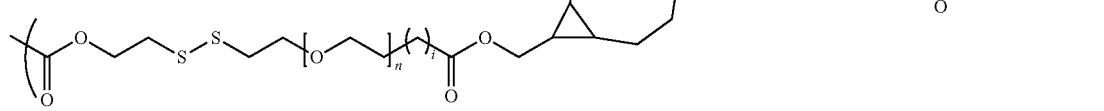

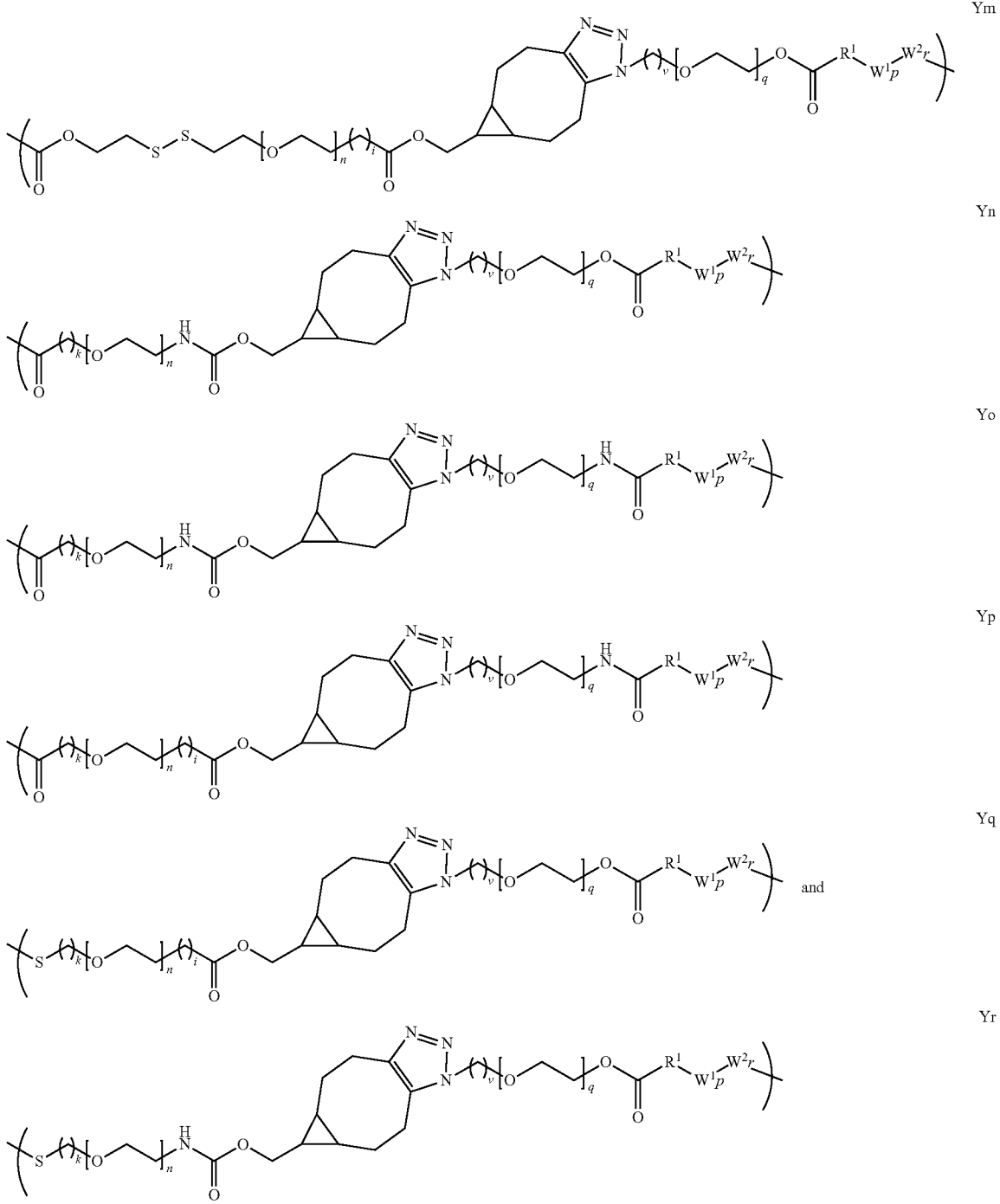

where the left, opening parentheses "(" signifies the location of the bond between X and Y, the right, closing parentheses ")" signifies the location of the bond between Y and $R^2$. In several embodiments, n is an integer greater than or equal to about: 1, 10, 20, 40, 50, 75, 100, 150 or ranges including and/or spanning the aforementioned values. In several embodiments, n is an integer greater than or equal to about: 1, 2, 3, 4, 5, 10, 15, 20, 30, 40, 50, or ranges including and/or spanning the aforementioned values. In several embodiments, q is an integer greater than or equal to about: 1, 10, 20, 40, 50, 75, 100, 150 or ranges including and/or spanning the aforementioned values. In several embodiments, q is an integer greater than or equal to about: 1, 2, 3, 4, 5, 10, 15, 20, 30, 40, 50, 75, 100, 150, or ranges including and/or spanning the aforementioned values. In several embodiments, k is an integer greater than or equal to about: 1, 2, 3, 4, 5, 10, 15, 20, or ranges including and/or spanning the aforementioned values. In several embodiments, v is an integer greater than or equal to about: 1, 2, 3, 4, 5, 10, 15, 20, or ranges including and/or spanning the aforementioned values.

In several embodiments, k is 2. In several embodiments, v is 2. In several embodiments, n is 4. In several embodiments, n is 44. In several embodiments, q is 3. As used herein, variables disclosed as having structure, a value, or a range of values for one embodiment, may also have those values when the variable is used in another embodiment (even where the variable is not defined with respect to that other embodiment). In several embodiments, n is an integer from 1 to 100. In several embodiments, q is an integer from 1 to 44. In several embodiments, k is an integer from 1 to 12. In several embodiments, i is an integer from 0 to 20. In several embodiments, v is an integer from 1 to 4. In several embodiments, $R_1$ is —$CH_2$—, —$(CH_2)_2$—C$(CH_3)(CN)$—, —$(CH_2)_2$—C$(CH_3)(CH_3)$—, —$(CH_2)_2$—CH$(CH_3)$— or —CH$(CH_3)$—. In several embodiments, $W^1$ and $W^2$ are as depicted below:

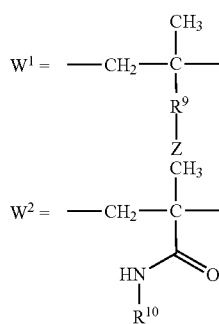

where Z is mannose or a mannose receptor-targeting moiety, $R^9$ is a direct bond, —$(CH_2)_2$—NH—C(O)— (an ethylaceetamido group or "EtAcN") or —$(CH_2)_2$—(O—$CH_2$—$CH_2)_t$—NH—C(O)— (a pegylated ethylacetamido group or "Et-PEG$_t$-AcN"), t is an integer from 1 to 5, p is an integer from 2 to 250, $R^{10}$ is an aliphatic group, an alcohol, an aliphatic amine-containing group, or an aliphatic alcohol, and r is an integer from 0 to 250. In several embodiments, —$W^1_p$-$W^2_r$— (e.g., as provided in —$[Y(Z)_p]$— or in linker structures) is a random copolymer or block copolymer of $W_1$ and $W_2$. In several embodiments, the number of repeat units of $W^1$ is denoted as p and wherein p is an integer of at least about 1. In several embodiments, the number of repeat units of $W^2$ is denoted as r and wherein r is an integer of at least about 1. In some embodiments, $R^{10}$ is a $C_f$alkyl or $C_f$alkylOH$_g$, where f represents the number of carbons in the alkyl group and is an integer between 0 and 10, and g represents the number of hydroxyl groups present on the alkyl group and is an integer between 0 and 10. In some embodiments, $R^{10}$ is 2-hydroxyethyl. In some aspects —$W^1_p$-$W^2_q$— represents a block copolymer or a random copolymer of $W^1$ and $W^2$ monomers.

In several embodiments, the linker comprises a polymeric chain with pendant liver targeting moieties decorating the polymeric chain. In some embodiments, the polymeric chain (or Y) comprises Y' as disclosed elsewhere herein. In several embodiments, the polymeric chain comprises an acrylate portion (e.g., acrylate-based polymers and/or acrylate-based copolymers). In several embodiments, the acrylate portion comprises one or more acrylate units (e.g., acrylate derivatives, including methacrylates and derivatives thereof) comprising a pendant liver targeting agent. In several embodiments, the polymeric chain comprises a hydrophilic portion and/or region. In several embodiments, the hydrophilic portion comprises a length of one or more regions having —$(CH_2CH_2O)_s$— where s is an integer from about 1 to about 44. In several embodiments, s is an integer greater than or equal to about: 1, 2, 3, 4, 5, 10, 15, 20, 30, 40, 50, 75, 100, 150, or ranges including and/or spanning the aforementioned values. In some embodiments, the hydrophilic portion comprises one or more polyethylene glycol (PEG) regions. In some embodiments, the PEG may have polydispersity as measured by the weight average molecular weight in g/mol (Mw) of the PEG divided by the number average molecular weight in g/mol (Mw) of the PEG (e.g., Mw/Mn). In some embodiments, the PEG chains have a number average or weight average molecular weight (g/mol) of equal to or at least about: 500, 1000, 2000, 5000, 10000, or ranges including and/or spanning the aforementioned values. In several embodiments, the polymeric chain is optionally substituted. In some embodiments, the polymeric chain comprises pendant hydrophilic groups such as a —OH, —SO(OH)$_2$, optionally substituted polyether, optionally substituted polyamino, and the like.

In several embodiments, the antigen and liver targeting portion of the compound are joined using click chemistry, for example, by functionalizing the antigen with a first linker arm comprising an alkynyl group (or an azide), functionalizing the liver targeting moiety with a second linker arm comprising an azide (or an alkynyl group), and clicking them together via "click" chemistry. In some embodiments, an alkynyl group that can be clicked in copper-free conditions is used. In some embodiments, —$[Y(-Z)_p]$— is a group represented by one or more of Formulae AI-AIV:

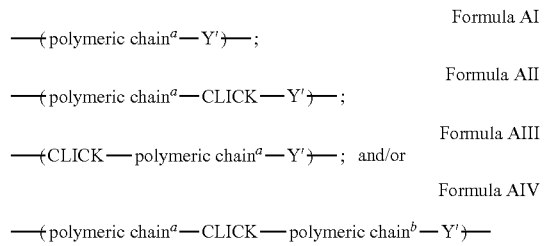

where the left, opening parentheses "(" signifies the location of the bond between X and Y, the right, closing parentheses ")" signifies the location of the bond between Y and $R^2$, Y' is a random copolymer or block copolymer of two or more different types of repeat units, wherein at least one type of repeat unit comprises a pendant Z group, (or plurality of pendant Z groups) where Z is mannose and/or a mannose receptor-targeting moiety. In some embodiments, Y' is a random copolymer or block copolymer of $W^1$ and $W^2$, where $W^1$ and $W^2$ are as depicted below:

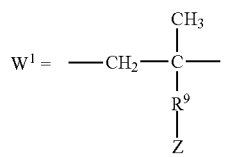

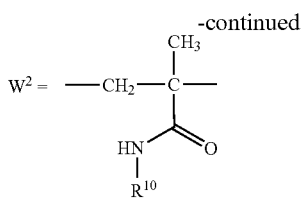

where Z is mannose and/or a mannose receptor-targeting moiety (including, but not limited to, one or more of mannosamine, N-acetylmannosamine, or N-acetylglucosamine), $R^9$ is a direct bond, optionally substituted —C(O)—NH—$(CH_2)_2$— (an ethylaceetamido group or "EtAcN") or optionally substituted —C(O)—NH—$(CH_2)_2$—(O—$CH_2$—$CH_2$)$_t$— (a pegylated ethylacetamido group or "Et-PEG$_t$-AcN"), t is an integer from 1 to 5. In some embodiments, t is an integer of equal to or at least about: 1, 2, 3, 4, 5, 10, 20, or ranges including and/or spanning the aforementioned values. In several embodiments, $R^{10}$ is an aliphatic group, an alcohol, an aliphatic amine-containing group, or an aliphatic alcohol. In some embodiments, $R^9$ or $R^{10}$ are independently optionally substituted alkyl, an optionally substituted polyether, or optionally substituted polyamino. In some embodiments, $R^{10}$ is an optionally substituted $C_f$alkyl, optionally substituted $C_f$alkylOH$_g$, or an optionally substituted —($C_f$alkylOH$_g$)—O)$_e$—H where f represents the number of carbons in the alkyl group and is an integer between 0 and 10, g represents the number of hydroxyl groups present on the alkyl group and is an integer between 0 and 10, and e represents the number of alkyl/ether repeat units and is an integer between 0 and 10. In some embodiments, e, f, and g are independently selected integers of equal to or at least about: 0, 1, 2, 3, 4, 5, 10, or ranges including and/or spanning the aforementioned values. In some embodiments, $R^{10}$ is a 2-hydroxyethyl (e.g., —$CH_2CH_2OH$). In some embodiments, $R^{10}$ is an optionally substituted 2-hydroxyethyl. In some embodiments, $R^{10}$ is an optionally substituted polyether.

In some embodiments, Y' is represented as —$W^1_p$-$W^2_r$—. As noted elsewhere herein, —$W^1_p$-$W^2_r$— may represent a block copolymer or a random copolymer of $W^1$ and $W^2$ monomers having p repeat units of $W^1$ and r repeat units of $W^2$. In some embodiments, p is an integer equal to or greater than about: 1, 50, 85, 100, 150, 165, 200, 225, 250, 300, 400, or ranges including and/or spanning the aforementioned values. In some embodiments, r is an integer equal to or greater than about: 1, 50, 85, 100, 150, 165, 200, 225, 250, 300, 400, or ranges including and/or spanning the aforementioned values. In some embodiments, Y' is a homopolymer of $W^1$ or $W^2$. In some embodiments, r is 0. In some embodiments, the sum of p and r is an integer equal to or greater than about: 1, 50, 85, 100, 150, 165, 170, 200, 225, 250, 300, 400, 600, 800, or ranges including and/or spanning the aforementioned values.

In some embodiments, polymeric chain$^a$ and polymeric chain$^b$ are present or optionally not present. In some embodiments, where present, polymeric chain$^a$ and polymeric chain$^b$ can independently comprise hydrophilic polymers. In some embodiments, where present, polymeric chain$^a$ and polymeric chain$^b$ can independently comprise one or more optionally substituted —($CH_2CH_2O$)$_s$—, optionally substituted —($CH_2$)$_u$—, or optionally substituted alkylene. In several embodiments, u is an integer less than or equal to about: 1, 5, 10, 20, or ranges including and/or spanning the aforementioned values. In some embodiments, polymeric chain$^a$ and polymeric chain$^b$ comprise or consist of one or more of the following structures, or a portion thereof:

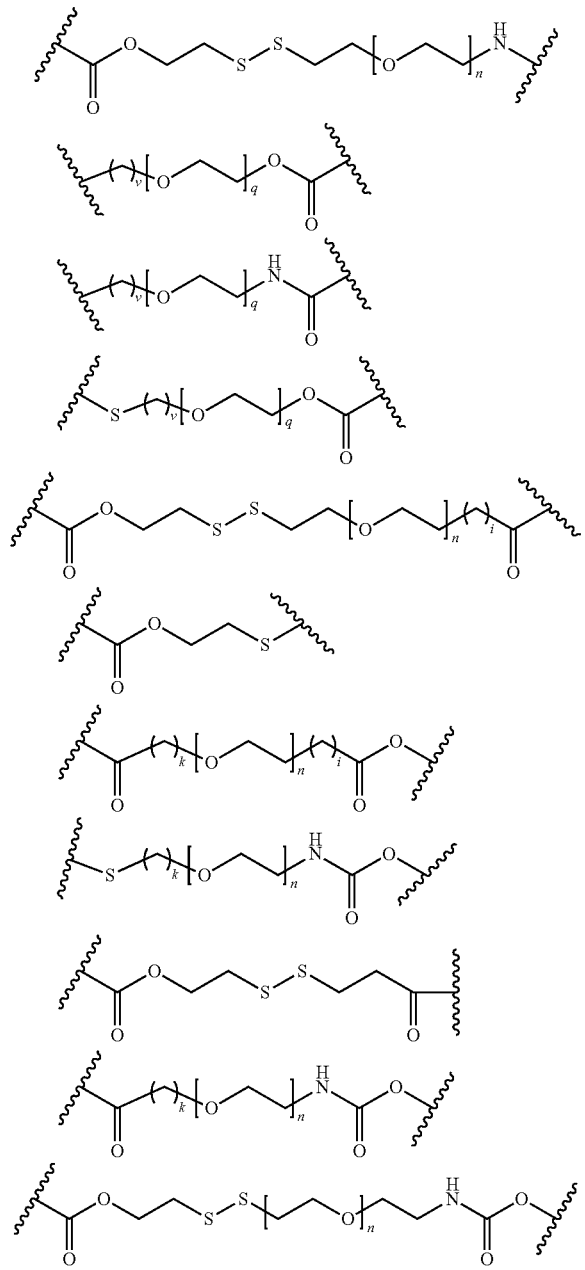

wherein the variables (e.g., i, k, n, q, v, etc.) are as disclosed elsewhere herein. In several embodiments, for example, n is an integer from about 1 to about 100, q is an integer from about 1 to about 100, k is an integer from about 1 to about 20, i is an integer from about 0 to about 20, and v is an integer from about 1 to about 20. In several embodiments, n or q represents the number of repeat units in a PEG chain. In some embodiments, the PEG chain may have some polydispersity. In some embodiments, n and q do not indicate a number of repeat units but instead independently indicate the presence of a PEG polymer chain having a Mn (in g/mol) or Mw (in g/mol) of equal to or at least about 500, 1000, 2000, 5000, 10000, or ranges including and/or spanning the aforementioned values. In some embodiments, k, i, and v can each independently comprise an optionally substituted alkylene.

In several embodiments, n is an integer greater than or equal to about: 1, 10, 20, 40, 50, 75, 100, 150 or ranges including and/or spanning the aforementioned values. In several embodiments, n is an integer greater than or equal to about: 1, 2, 3, 4, 5, 10, 15, 20, 30, 40, 50, or ranges including and/or spanning the aforementioned values. In several embodiments, q is an integer greater than or equal to about: 1, 10, 20, 40, 50, 75, 100, 150 or ranges including and/or spanning the aforementioned values. In several embodiments, q is an integer greater than or equal to about: 1, 2, 3, 4, 5, 10, 15, 20, 30, 40, 50, 75, 100, 150, or ranges including and/or spanning the aforementioned values. In several embodiments, k is an integer greater than or equal to about: 1, 2, 3, 4, 5, 10, 15, 20, or ranges including and/or spanning the aforementioned values. In several embodiments, v is an integer greater than or equal to about: 1, 2, 3, 4, 5, 10, 15, 20, or ranges including and/or spanning the aforementioned values. In several embodiments, k is 2. In several embodiments, v is 2. In several embodiments, n is 4. In several embodiments, n is 44. In several embodiments, q is 3. As used herein, variables disclosed as having structure, a value, or a range of values for one embodiment, may also have those values when the variable is used in another embodiment (even where the variable is not defined with respect to that other embodiment).

In several embodiments, the "CLICK" group and/or —[Y(—Z)$_p$]—, more generally, comprises the following functional unit:

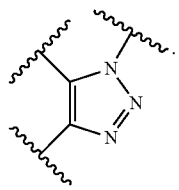 [SMILES: *c1nnn(*)c1*]

In several embodiments, the "CLICK" group and/or —[Y(—Z)$_p$]—, more generally, comprises one or more of the following units (each of which may be optionally substituted):

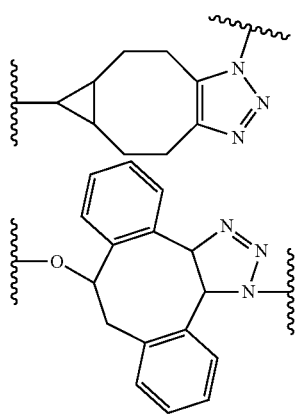

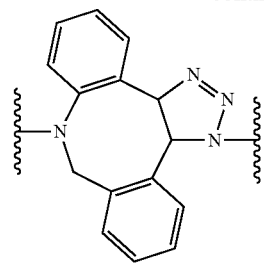

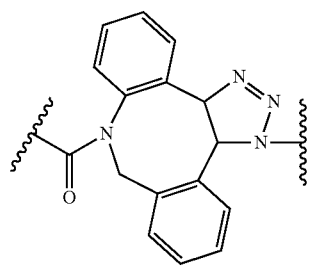

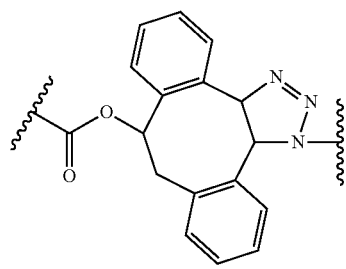

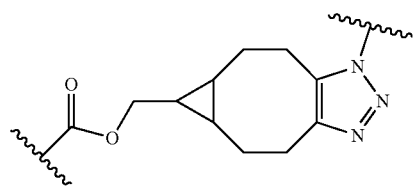

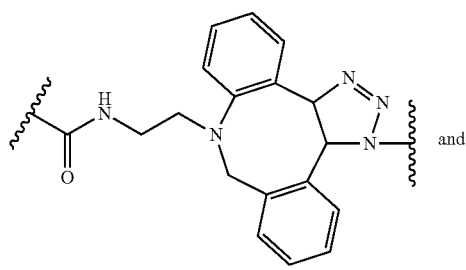

and

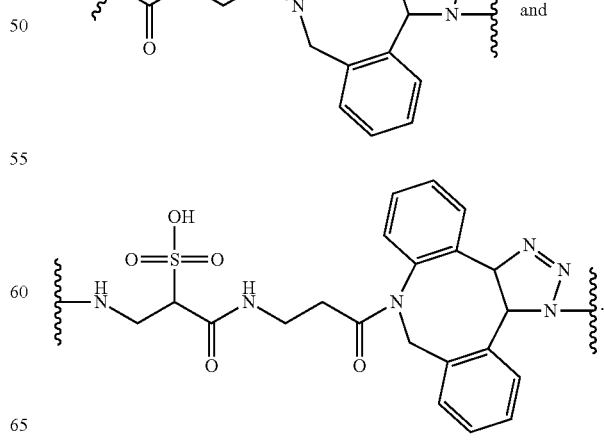

In several embodiments, —[Y(—Z)p]- comprises the one or more of the following functional units:

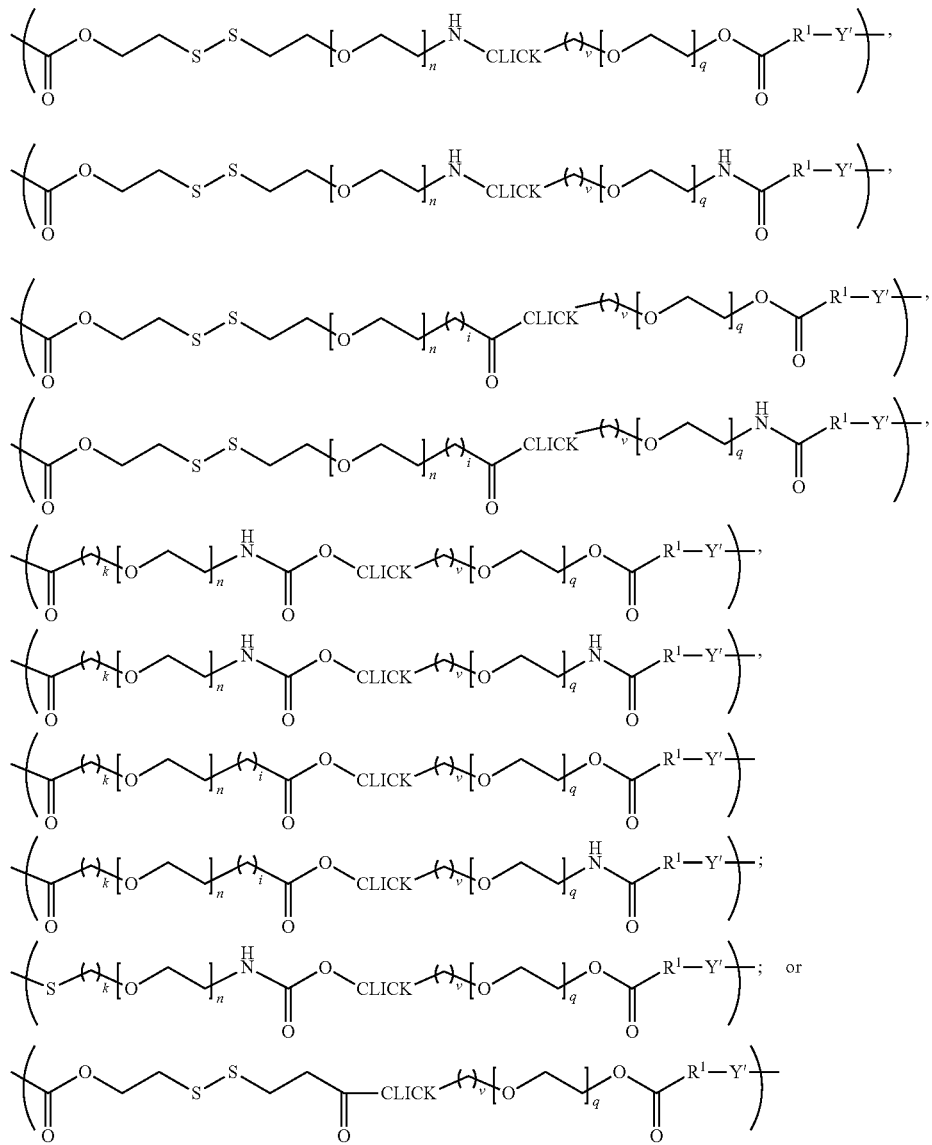

wherein each variable (e.g., i, k, n, q, v, CLICK, $R^1$, Y', etc.) is as disclosed elsewhere herein. In some embodiments, for example, n is an integer from about 1 to about 44, q is an integer from about 1 to about 44, k is an integer from about 1 to about 12, i is an integer from about 0 to about 20, v is an integer from about 1 to about 4, and $R_1$ is —$CH_2$—, —$(CH_2)_2$—$C(CH_3)$(CN)—, —$(CH_2)_2$—$C(CH_3)(CH_3)$—, —$(CH_2)_2$—CH$(CH_3)$—, —CH$(CH_3)$—, or is absent.

In several embodiments, —[Y(Z)$_p$]— is a group represented by any one or more of Formula Ya' to Yr':

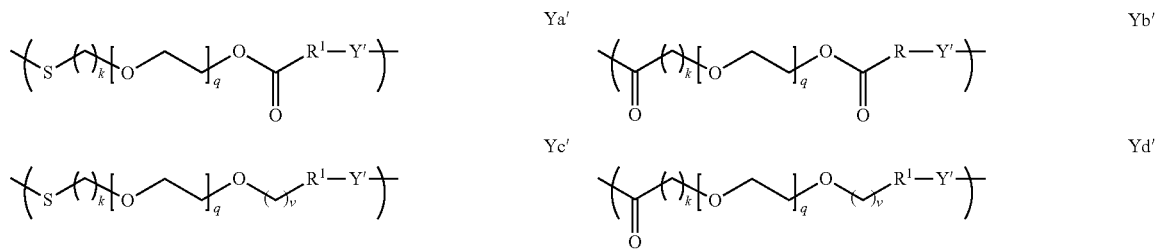

-continued
Ye'
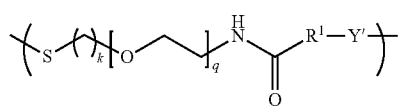
Ye''
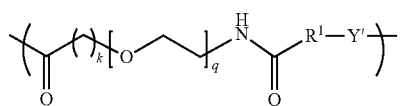
Yf'
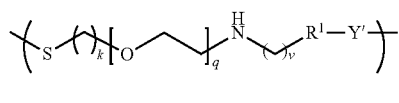
Yf''
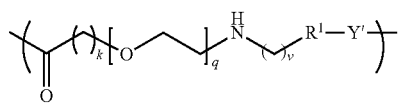
Yg'
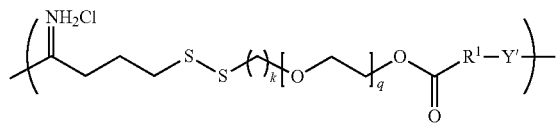
Yh'
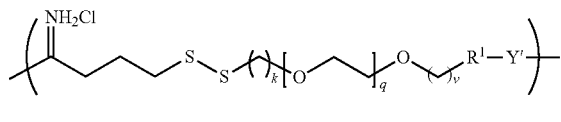
Yi'
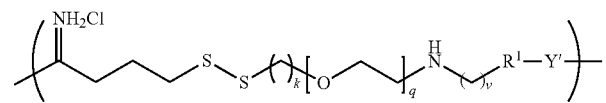
Yj'
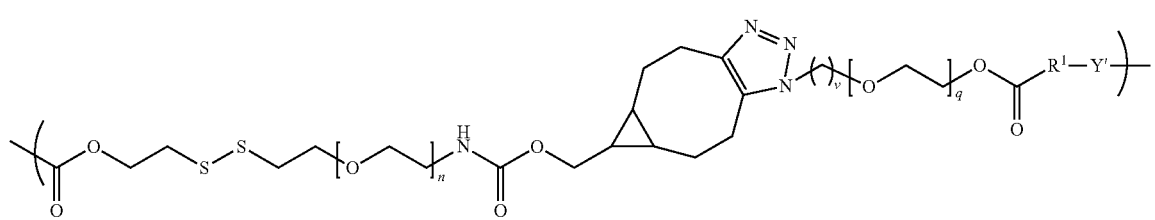
Yk'
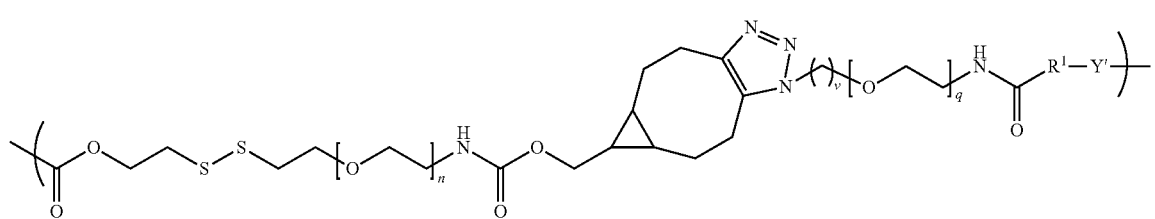
Yl'
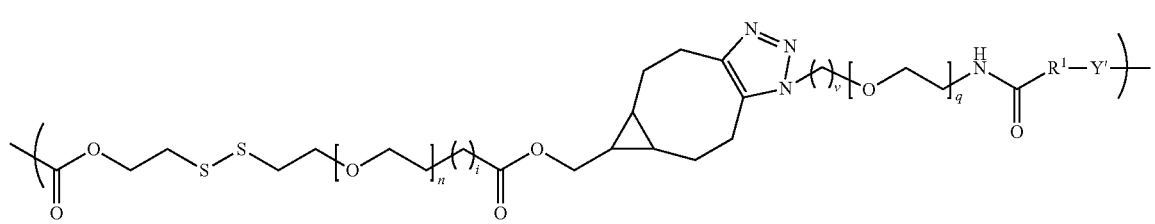
Ym'
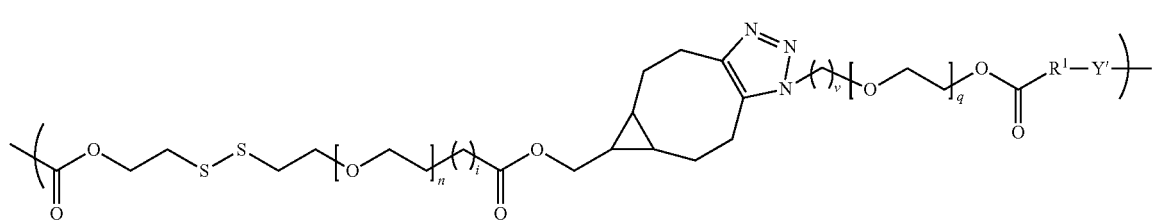

-continued

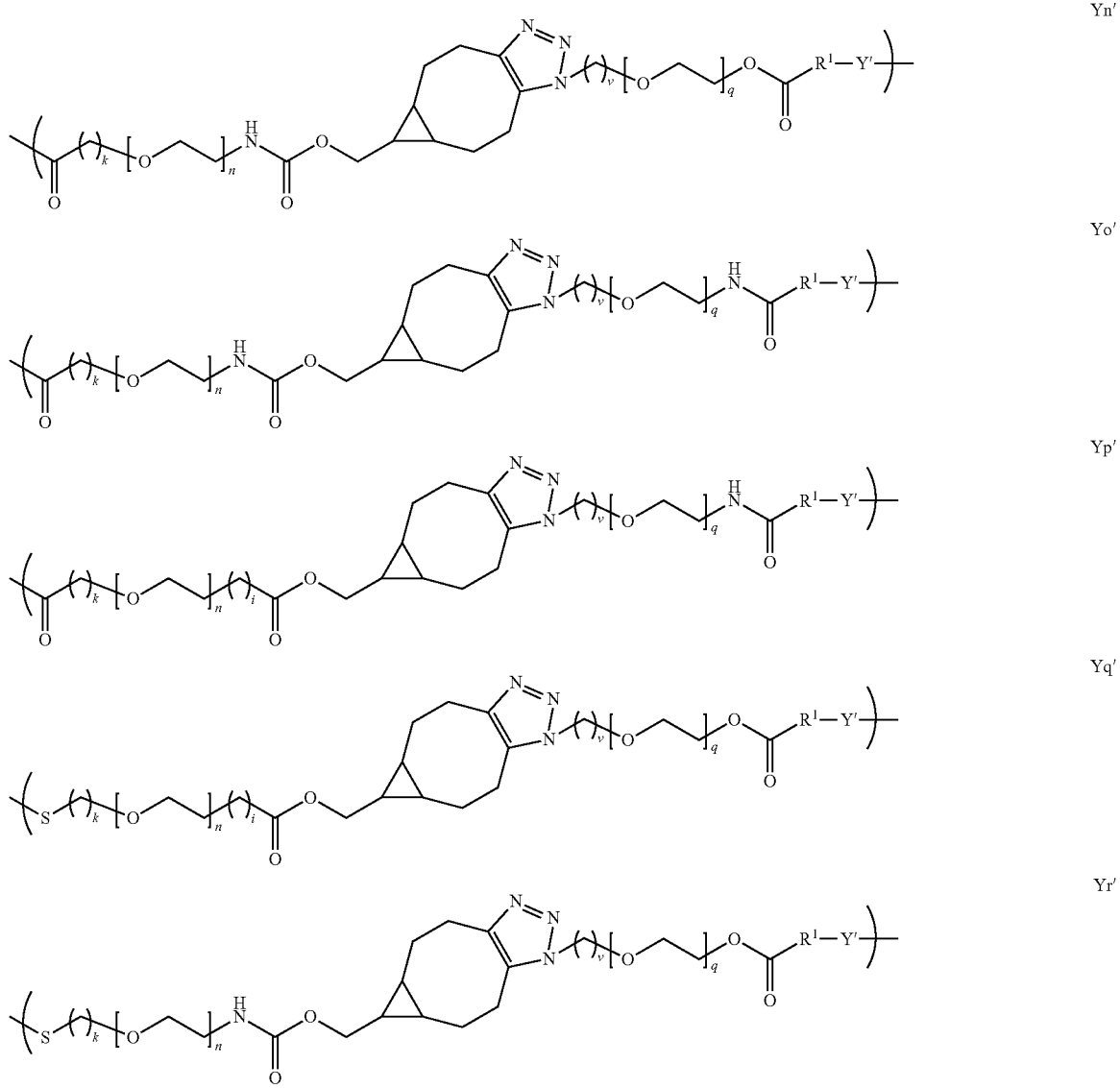

wherein the variables (e.g., i, k, n, q, v, $R^1$, Y', etc.) are as disclosed elsewhere herein. For example, in several embodiments, n is an integer greater than or equal to about: 1, 2, 3, 4, 5, 10, 15, 20, 30, 40, 50, or ranges including and/or spanning the aforementioned values. In several embodiments, q is an integer greater than or equal to about: 1, 2, 3, 4, 5, 10, 15, 20, 30, 40, 50, 75, 100, 150, or ranges including and/or spanning the aforementioned values. In several embodiments, k is an integer greater than or equal to about: 1, 2, 3, 4, 5, 10, 15, 20, or ranges including and/or spanning the aforementioned values. In several embodiments, v is an integer greater than or equal to about: 1, 2, 3, 4, 5, 10, 15, 20, or ranges including and/or spanning the aforementioned values. In several embodiments, k is 2. In several embodiments, v is 2. In several embodiments, n is 4. In several embodiments, n is 43 or 44. In several embodiments, q is 3. In several embodiments, $R_1$ is —$CH_2$—, —$(CH_2)_2$—$C(CH_3)(CN)$—, —$(CH_2)_2$—$C(CH_3)(CH_3)$—, —$(CH_2)_2$—$CH(CH_3)$— or —CH ($CH_3$)—. In some embodiments, Y' is a random copolymer or block copolymer of $W^1$ and $W^2$ having p repeat units of $W^1$ and r repeat units of $W^2$.

In several embodiments, as shown elsewhere herein, the targeting portion comprises one or more pendant liver targeting moieties decorating a portion of the linker. In several embodiments, the portion of the linker is a polymeric chain with pendant targeting agents attached randomly or in blocks along the chain. In some embodiments, the polymeric chain comprises an acrylate portion (e.g., acrylate polymers and/or acrylate copolymers). In several embodiments, the acrylate portion comprises an acrylate unit comprising a pendant liver targeting agent. In several embodiments, the acrylate portion further comprises an acrylate unit not comprising a pendant liver targeting agent.

In some embodiments, Y is a linker resulting from one or more reactions involving at least one of the following: N-hydroxysuccinamidyl (NHS) linker, NHS ester linker, PEG linker, maleimide linker, vinylsulfone linker, pyridyl di-thiol-poly(ethylene glycol) linker, pyridyl di-thiol linker, n-nitrophenyl carbonate linker, or a nitrophenoxy poly(ethylene glycol)ester linker. The linker may have one or more mannose and/or a mannose receptor-targeting moieties (including, but not limited to, one or more of mannosamine, N-acetylmannosamine, or N-acetylglucosamine) bound to it. In embodiments, Y comprises an antibody, an antibody fragment, a peptide, or a disulfanyl ethyl ester to which one or more mannose and/or mannose receptor-targeting moieties (including, but not limited to, one or more of mannosamine, N-acetylmannosamine, or N-acetylglucosamine) are bound.

In some embodiments, —[Y(—Z)$_p$]— comprises one of the following structures:

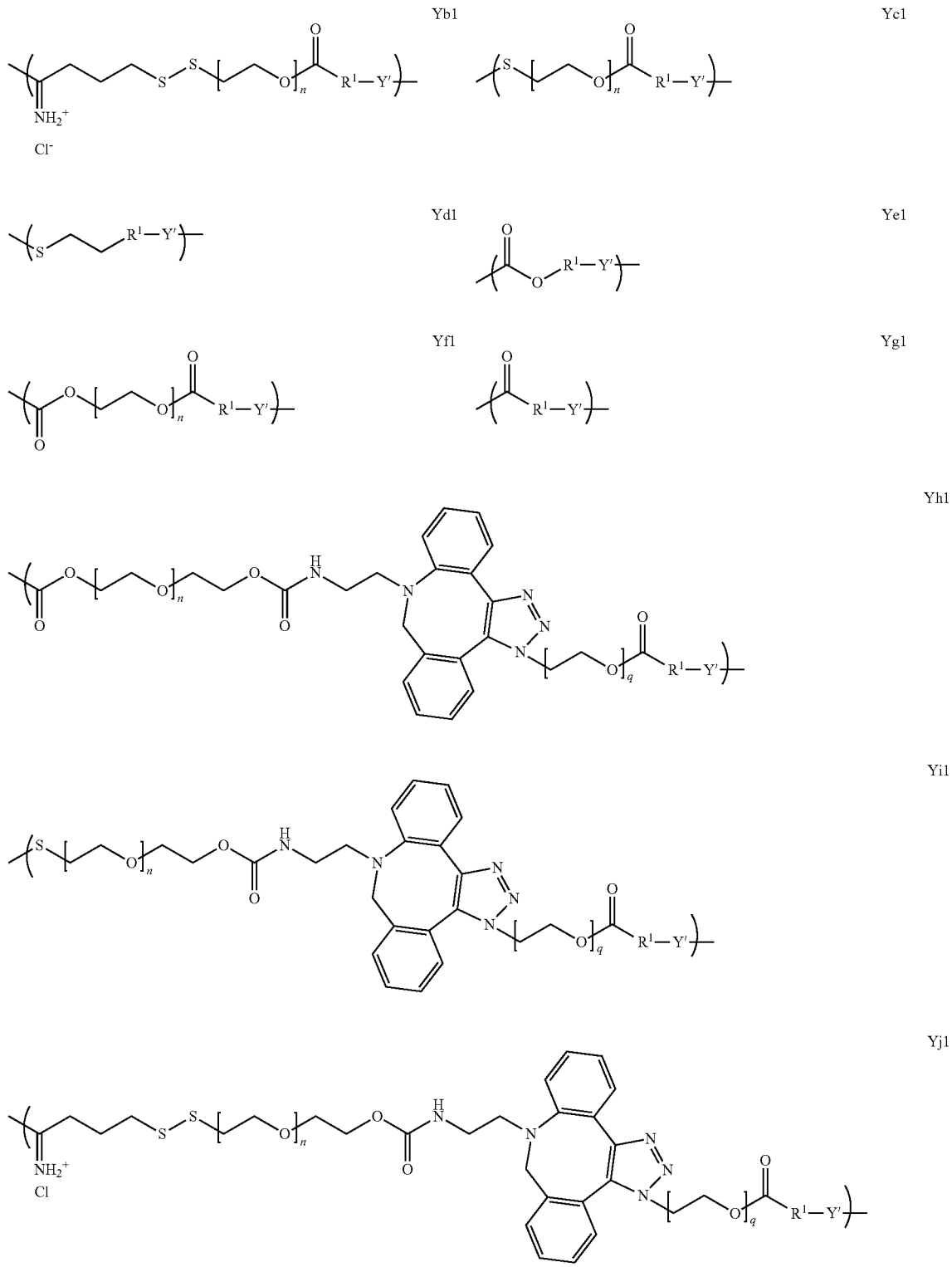

-continued

Yk1
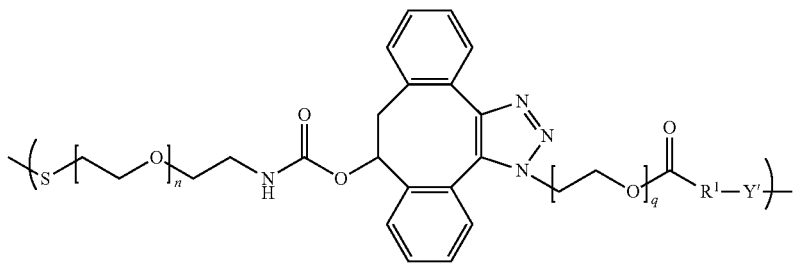

YL1
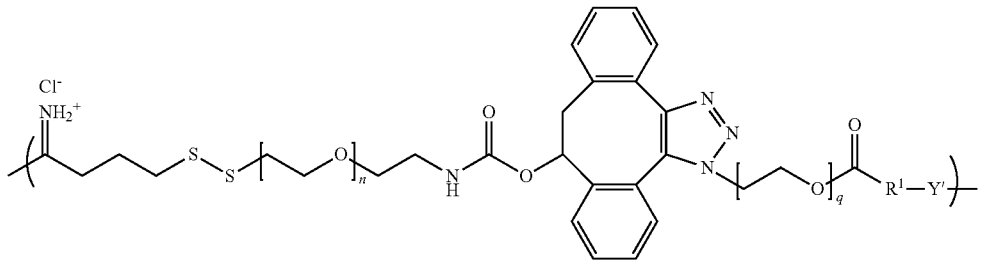

Ym1
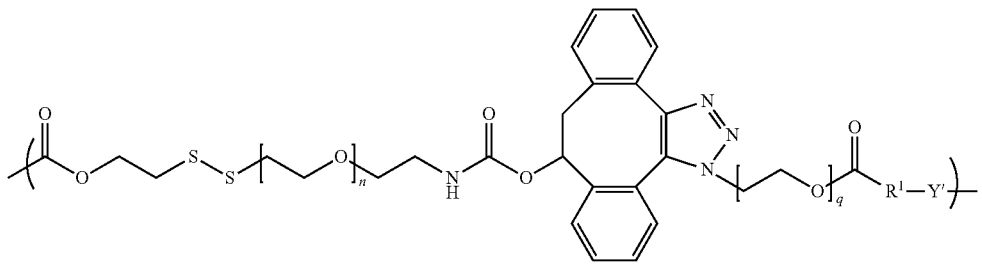

Yn1
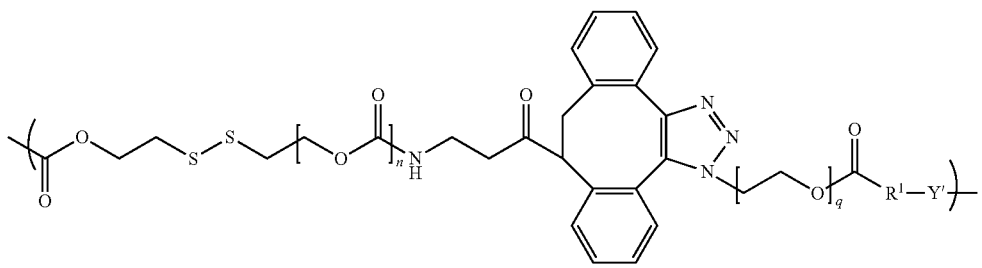

Yo1
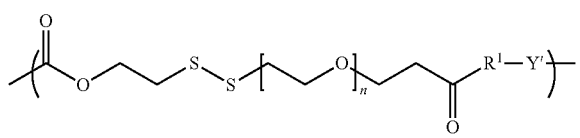

Yp1
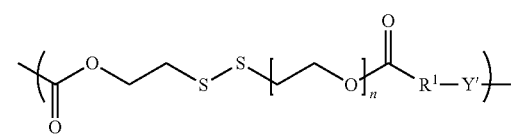

where the variables are as disclosed elsewhere herein.

In some embodiments, other linker structures can be found in U.S. Application Publication Nos. U.S. 2017/0007708A1 and 2016/0243248A1 and International Publication No. WO 2017/046652, each of which is incorporated by reference in its entirety.

In several embodiments, various ratios of $W^1$ to $W^2$ are used (e.g., $W^1$ and $W^2$ as provided in any of the Formulae disclosed elsewhere herein). In some embodiments, a majority of Y' repeat units comprise $W^1$. In some embodiments, the ratio of $W^1$ to $W^2$ is equal to or greater than about 50:1, about 25:1, about 10:1, about 5:1, about 4:1, about 2:1, about 1:1, about 1:2, about 1:4, about 1:5, about 1:10, about 1:25, about 1:50, and any ratio in between those listed, including endpoints. In some embodiments, the ratio of p to r is equal to or greater than about 50:1, about 25:1, about 10:1, about 5:1, about 4:1, about 2:1, about 1:1, about 1:2, about 1:4, about 1:5, about 1:10, about 1:25, about 1:50, and any ratio in between those listed, including endpoints. In some embodiments, a homopolymer of $W^1$ is provided without a $W^2$ portion.

X may be a foreign transplant antigen, or alloantigen, or autoimmune antigen. In some aspects, X represents an antigen against which a patient may develop or has developed an unwanted immune response. In some embodiments, X is an antigen against which a subject, such as a transplant recipient or autoimmune patient, develops an unwanted immune response. In several embodiments, X is a foreign extracellular vesicle, cell fragment, or cell containing alloantigens against which transplant recipients or autoimmune patients develop and unwanted immune response. In still further embodiments, X is a foreign food, animal, plant or environmental antigen against which patients develop an unwanted immune response. In certain aspects, X is a foreign therapeutic agent against which patients develop an unwanted immune response. In a further aspect, X is a synthetic self-antigen to which patients develop an unwanted immune response. In several embodiments, X is a tolerogenic portion of a larger antigen. In certain embodiments, X, or a portion of X, is, is at least, or is at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 amino acids in length (or any range derivable therein). In some embodiments, X is an asparaginase antigen or an ovalbumin antigen. In several embodiments, X is an immunogenic fragment of one or more of myelin basic protein, myelin oligodendrocyte glycoprotein, proteolipid protein, insulin, proinsulin, preproinsulin, high molecular weight glutenin, low molecular weight glutenin, alpha- or gamma-gliadin, hordein, secalin, or avenin.

In some embodiments, Z, the moiety that specifically targets a mannose receptor, is selected from the group consisting of α-linked mannose, β-linked mannose, substituted mannose, mannose-6-phosphate, N-acetyl mannosamine, and mannan having β(1-4), α(1-6), α(1-2), and/or α(1-3) linkages. In some aspects, the mannose receptor is the mannose-6-phosphate receptor.

Some aspects of the disclosure are directed towards the use of a composition as disclosed herein in any method disclosed herein. Some embodiment provide for the use of any composition disclosed herein for the induction of tolerance to the antigen or a tolerogenic portion thereof. It is specifically contemplated that any step or element of an embodiments may be implemented in the context of any other step(s) or element(s) of a different embodiment disclosed herein.

In some embodiments, a method of inducing immunological tolerance to an antigen target is provided. The method comprises administering a composition of Formula 1:

X—[Y(Z)$_p$]$_m$—R$^2$        Formula 1 where the variables are as disclosed elsewhere herein. In some embodiments, for example, X comprises an antigen or a tolerogenic portion thereof, Y comprises a linker moiety, Z comprises a moiety that specifically targets a mannose receptor, p is an integer from 2 to 250, m is an integer from 1 to 100, R$^2$ is any of functional groups I-III:

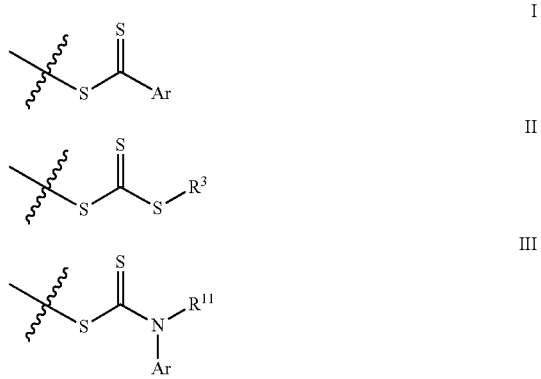

where Ar is a substituted or unsubstituted aromatic group, R$^3$ is any carbon-containing linear or heterocyclic moiety, and R$^{11}$ is hydrogen or an alkyl group. In some embodiments, R$^2$ is one of the functional groups:

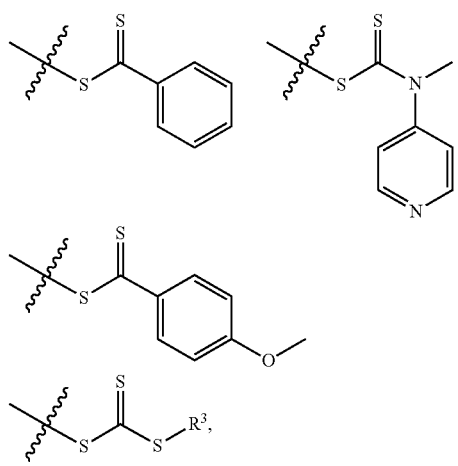

where R$^3$ is as defined above.

In some embodiments, Y is a linker as described elsewhere herein. In several embodiments, Y is a linker resulting from one or more reactions involving at least one of the following N-hydroxysuccinamidyl (NHS) linker, NHS ester linker, PEG linker, maleimide linker, vinylsulfone linker, pyridyl di-thiol-poly(ethylene glycol) linker, pyridyl di-thiol linker, n-nitrophenyl carbonate linker, or a nitrophenoxy poly(ethylene glycol)ester linker. The linker may have one or more mannose moieties or mannose receptor-targeting moieties bound to it. In embodiments, Y comprises an antibody, an antibody fragment, a peptide, or a disulfanyl ethyl ester to which one or more mannose moieties or mannose receptor-targeting moieties are bound. In several embodiments, —[Y(—Z)$_p$]— is as disclosed elsewhere herein. For example, in some aspects, —[Y(Z)$_p$]— is a group represented by one of sequence Formula Ya to Yr:

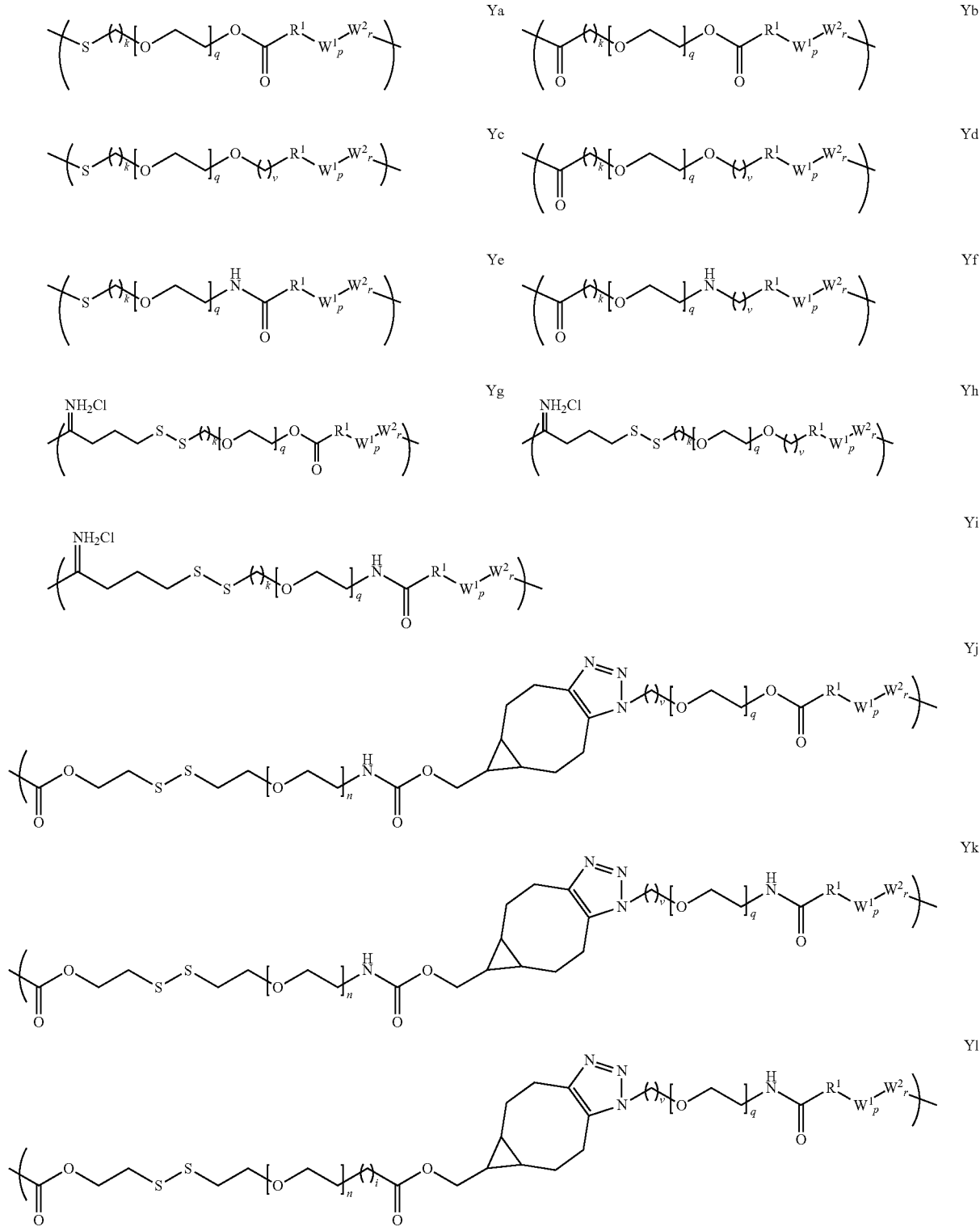

-continued
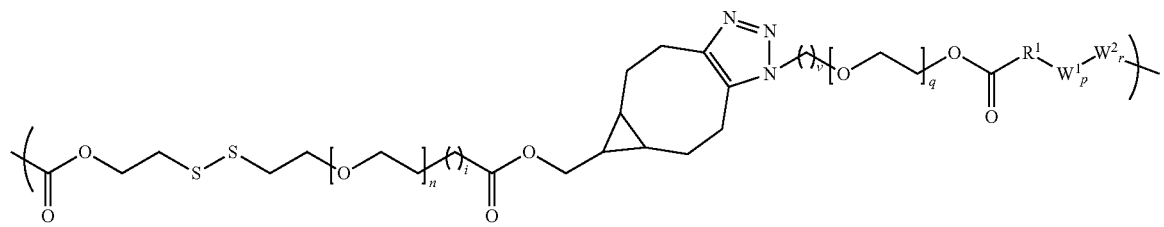
Ym
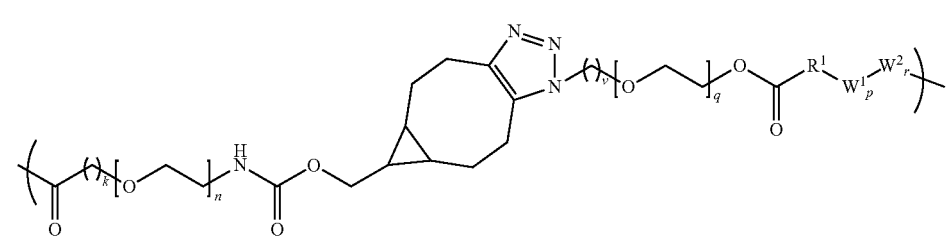
Yn
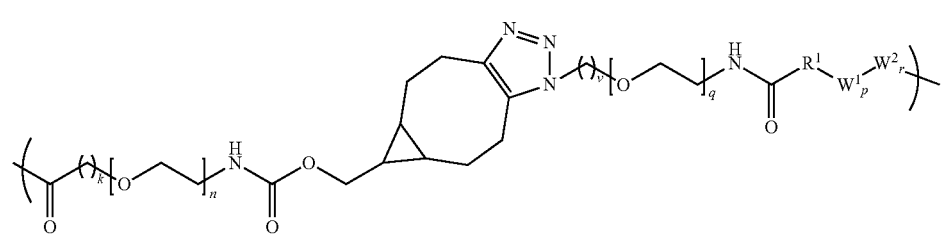
Yo
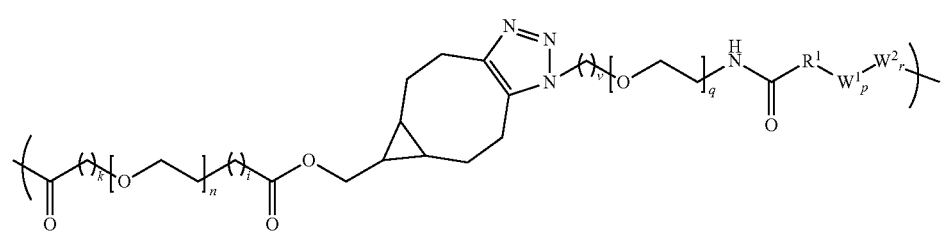
Yp
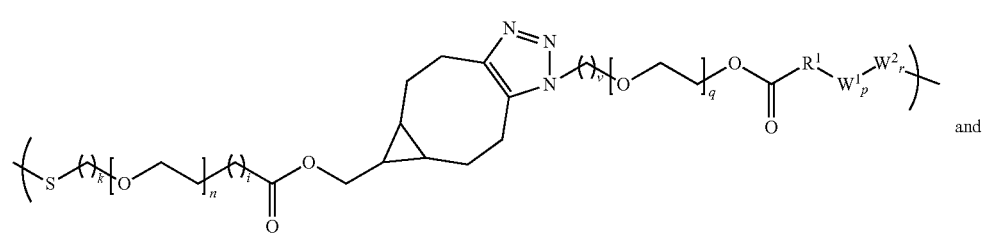
Yq
and
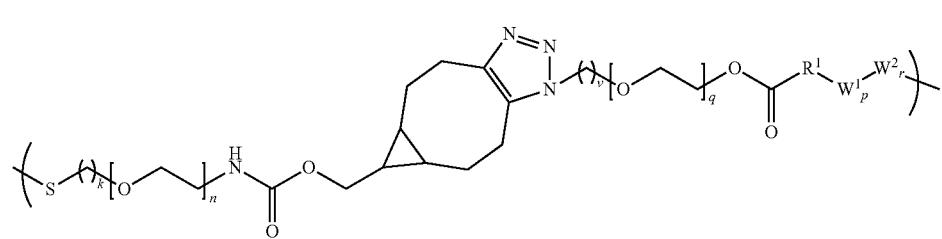
Yr where the left, opening parentheses "(" signifies the location of the bond between X and Y, the right, closing parentheses ")" signifies the location of the bond between Y and $R^2$, n is an integer from 1 to 100, q is an integer from 1 to 44, k is an integer from 1 to 12, i is an integer from 0 to 20, v is an integer from 1 to 4, $R_1$ is —$CH_2$—, —$(CH_2)_2$—$C(CH_3)(CN)$—, —$(CH_2)_2$—$C(CH_3)(CH_3)$—, —$(CH_2)_2$—$CH(CH_3)$— or —$CH(CH_3)$—, $W^1$ and $W^2$ are as depicted below:

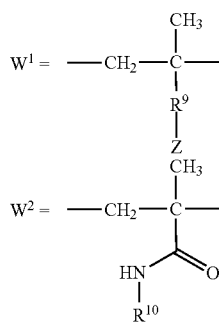

where Z is mannose or a mannose receptor-targeting moiety, $R^9$ is a direct bond, —$(CH_2)_2$—NH—C(O)— (an ethylaceetamido group or "EtAcN") or —$(CH_2)_2$—(O—$CH_2$—$CH_2)_t$—NH—C(O)— (a pegylated ethyl-acetamido group or "Et-PEG$_t$-AcN"), t is an integer from 1 to 5, 1 to 3, or 1 or 2, p is an integer from 2 to 250, $R^{10}$ is an aliphatic group, an alcohol, an aliphatic amine-containing group, or an aliphatic alcohol, and r is an integer from 0 to 250. In some embodiments, $R^{10}$ is a $C_f$alkyl or $C_f$alkylOH$_g$, where f represents the number of carbons in the alkyl group and is an integer between 0 and 10, and g represents the number of hydroxyl groups present on the alkyl group and is an integer between 0 and 10. In some embodiments, $R^{10}$ is 2-hydroxyethyl. In some aspects —$W^1{}_p$-$W^2{}_q$— represents a block copolymer or a random copolymer of $W^1$ and $W^2$ monomers.

X may be a foreign transplant antigen, or alloantigen, or autoimmune antigen. In some aspects, X represents an antigen against which a patient may develop or has developed an unwanted immune response. In some embodiments, X can be an antigen against which a subject, such as a transplant recipient or autoimmune patient, develops an unwanted immune response. In several embodiments, X can be a foreign extracellular vesicle, cell fragment, or cell containing alloantigens against which transplant recipients or autoimmune patients develop and unwanted immune response. In still further embodiments, X can be a foreign food, animal, plant or environmental antigen against which patients develop an unwanted immune response. In certain aspects X can be a foreign therapeutic agent against which patients develop an unwanted immune response. In a further aspect X can be a synthetic self-antigen to which patients develop an unwanted immune response. In several embodiments, X can be a tolerogenic portion of a larger antigen. In certain embodiments, X, or a portion of X, is at least, or is at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 amino acids in length (or any range derivable therein). In some embodiments, X is an asparaginase antigen or an ovalbumin antigen. In specific embodiments, X is an asparaginase antigen or an ovalbumin antigen, Z, the moiety that specifically targets a mannose receptor, may be selected from the group consisting of α-linked mannose, β-linked mannose, substituted mannose, mannose-6-phosphate, N-acetyl mannosamine, and mannan having β(1-4), α(1-6), α(1-2), and/or α(1-3) linkages.

In some aspects, a method of treating or preventing an unwanted immune response against an antigen is provided. The method comprises administering to a subject in need of suppression of an immune response to the antigen an effective amount of a composition comprising a compound of Formula 1. The composition can be administered for clearance of a circulating protein or peptide or antibody that specifically binds to antigen moiety X, which circulating protein or peptide or antibody is causatively involved in transplant rejection, immune response against a therapeutic agent, autoimmune disease, hypersensitivity and/or allergy. The composition can be administered in an amount effective to reduce a concentration of the antibodies that are causatively involved in transplant rejection, immune response against a therapeutic agent, autoimmune disease, hypersensitivity and/or allergy in blood of the patient by at least 50% w/w, as measured at a time between about 12 to about 48 hours after the administration. The composition can administered for tolerization of a patient with respect to antigen moiety X.

Other embodiments are discussed throughout this application. Any embodiment discussed with respect to one aspect applies to other aspects as well and vice versa. Each embodiment described herein is understood to be embodiments that are applicable to all aspects. It is contemplated that any embodiment discussed herein can be implemented with respect to any method or composition, and vice versa. Furthermore, compositions and kits can be used to achieve methods disclosed herein.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

The terms "effective amount" or "therapeutically effective amount" refer to that amount of a composition of the disclosure that is sufficient to effect treatment, as defined herein, when administered to a mammal in need of such treatment. This amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art.

The "numerical values" and "ranges" provided for the various substituents are intended to encompass all integers within the recited range. For example, when defining n as an integer representing a mixture including from 1 to 100, where the mixture typically encompasses the integer specified as n±10% (or for smaller integers from 1 to about 25, ±3), it should be understood that n can be an integer from 1 to 100 (e.g., 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, or any between those listed) The terms "±10%" or "±3" should be understood to disclose and provide specific support for equivalent ranges wherever used.

The term "optional" or "optionally" means that the subsequently described event or circumstance may or may not occur, and that the description includes instances where said event or circumstance occurs and instances in which it does not.

A peptide, protein, or fragment that specifically binds a particular target is referred to as a "ligand" for that target.

A "polypeptide" is a term that refers to a chain of amino acid residues, regardless of post-translational modification (e.g., phosphorylation or glycosylation) and/or complexation with additional polypeptides, and/or synthesis into multisubunit complexes with nucleic acids and/or carbohydrates, or other molecules. Proteoglycans therefore also are referred to herein as polypeptides. A long polypeptide (having over 50 amino acids) is referred to as a "protein." A short polypeptide (having 50 amino acids or fewer) is referred to as a "peptide." Depending upon size, amino acid composition and three dimensional structure, certain polypeptides can be referred to as an "antigen-binding molecule," "antibody," an "antibody fragment" or a "ligand." Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide.

As used herein, "pharmaceutically acceptable carrier" or "pharmaceutically acceptable excipient" includes any and all solvents, dispersion media, coatings, antibacterial and antifungal agents, isotonic and absorption delaying agents and the like. In several embodiments, these media and agents can be used in combination with pharmaceutically active substances. Except insofar as any conventional media or agent is incompatible with the active ingredient, its use in the therapeutic compositions is contemplated. Supplementary active ingredients can also be incorporated into the compositions.

The term "purified" as used herein with reference to a polypeptide refers to a polypeptide that has been chemically or biologically synthesized and is thus substantially uncontaminated by other polypeptides, or has been separated or isolated from most other cellular components by which it is naturally accompanied (e.g., other cellular proteins, nucleic acids, or cellular components such as lipid membrane). An example of a purified polypeptide is one that is at least 70%, by dry weight, free from the proteins and naturally occurring organic molecules with which it naturally associates. A preparation of a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, a FLAG® tag, a SNAP® tag, or other affinity tag) that facilitates purification or marking (e.g., capture onto an affinity matrix, visualization under a microscope). Thus a purified composition that comprises a polypeptide refers to a purified polypeptide unless otherwise indicated. The term "isolated" indicates that the polypeptides or nucleic acids of the disclosure are not in their natural environment. Isolated products of the disclosure can thus be contained in a culture supernatant, partially enriched, produced from heterologous sources, cloned in a vector or formulated with a vehicle, etc.

The term "sequence identity" is used with regard to polypeptide or polynucleotide sequence comparisons. This expression in particular refers to a percentage of sequence identity, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Particularly, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide. In several embodiments, despite differing sequences from a reference nucleotide (or corresponding polypeptide) a polynucleotide exhibits at least some degree of functional equivalence to the reference sequence, and in some embodiments, enhanced function.

The term "treatment" or "treating" means any treatment of a disease or disorder in a mammal, including: preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms.

The term "unwanted immune response" refers to a reaction by the immune system of a subject, which in the given situation is not desirable. The reaction of the immune system is unwanted if such reaction does not lead to the prevention, reduction, or healing of a disease or disorder but instead causes, enhances or worsens a disorder or disease. Typically, a reaction of the immune system causes, enhances or worsens a disease if it is directed against an inappropriate target. Exemplified, an unwanted immune response includes but is not limited to transplant rejection, immune response against a therapeutic agent, autoimmune disease, and allergy or hypersensitivity.

The term "operatively linked" refers to a situation where two components are combined to form the active complex prior to binding at the target site. For example, a molecule conjugated to one-half of a biotin-streptavidin complex and an antigen complexed to the other one-half of the biotin-streptavidin complex are operatively linked through complexation of the biotin and streptavidin molecules. The term operatively linked is also intended to refer to covalent or chemical linkages that conjugate two molecules together.

Throughout this application, the term "about" is used according to its plain and ordinary meaning in the area of protein chemistry to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Methods may involve multiple administrations of one or more compounds, compositions, and/or agents. In certain embodiments, cells or a subject are provided with a tolerance inducing agent prior to administering the composition for which a tolerance is being induced. It is contemplated that compounds, compositions, and/or agents may be formulated in a pharmaceutically acceptable formulation in certain embodiments of the invention.

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include conditions for which cosmetic therapy is sought, such as skin wrinkling, skin blemishes, and the like. The disease can be any disease, and non-limiting examples include hyperproliferative diseases such as cancer and pre-malignant lesions, wounds, and infections.

A subject may be "predicted to have" a disease if the subject exhibits a characteristic, condition, or behavior that increases the likelihood of getting a disease. The characteristic, condition, or behavior that increases the likelihood of getting a disease is known as a risk factor, and may be behavioral, physiological, demographic, environmental, or genetic in nature. Behavioral risk factors usually relate to actions that a subject has chosen to take. Demographic risk factors are those that relate to the overall population, such as age or gender. Environmental risk factors include those that are related to exposure to objects in an environment, such as air pollution and access to clean water. Genetic risk factors are based on an individual's genetic makeup, and may reflect interaction between the genes of the individual and environmental factors. A subject having a high number of manifestations of risk factors associated with a disease may be at increased risk of developing the disease, and may be "predicted to have" the disease.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

As used herein, an "antigen" is any substance that serves as a target for the receptors of an adaptive immune response, such as the T cell receptor, major histocompatibility complex class I and II, B cell receptor or an antibody. In some embodiments, an antigen may originate from within the body (e.g., "self," "auto" or "endogenous"). In additional embodiments, an antigen may originate from outside the body ("non-self," "foreign" or "exogenous"), having entered, for example, by inhalation, ingestion, injection, or transplantation, transdermal, etc. In some embodiments, an exogenous antigen may be biochemically modified in the body. Foreign antigens include, but are not limited to, food antigens, animal antigens, plant antigens, environmental antigens, therapeutic agents, as well as antigens present in an allograft transplant. Non-limiting examples of antigens are provided herein.

An "antigen-binding molecule" as used herein relates to molecules, in particular to proteins such as immunoglobulin molecules, which contain antibody variable regions providing a binding (specific binding in some embodiments) to an epitope. The antibody variable region can be present in, for example, a complete antibody, an antibody fragment, and a recombinant derivative of an antibody or antibody fragment. The term "antigen-binding fragment" of an antibody (or "binding portion"), as used herein, refers to one or more fragments of an antibody that retain the ability to specifically bind a target sequence. Antigen-binding fragments containing antibody variable regions include (without limitation) "Fv", "Fab", and "F(ab')$_2$" regions, "single domain antibodies (sdAb)", "nanobodies", "single chain Fv (scFv)" fragments, "tandem scFvs" ($V_H$A-$V_L$A-$V_H$B-$V_L$B), "diabodies", "triabodies" or "tribodies", "single-chain diabodies (scDb)", and "bi-specific T-cell engagers (BiTEs)".

An "epitope", also known as antigenic determinant, is the segment of a macromolecule, e.g. a protein, which is recognized by the adaptive immune system, such as by antibodies, B cells, major histocompatibility complex molecules, or T cells. An epitope is that part or segment of a macromolecule capable of binding to an antibody or antigen-binding fragment thereof. In this context, the term "binding" in particular relates to a specific binding. In the context of several embodiments of the present invention it is preferred that the term "epitope" refers to the segment of protein or polyprotein that is recognized by the immune system.

The term mannose or mannosylating moiety refers to a monosaccharide sugar that exists both in open-chain form and in cyclic form, having D- and L-isomers. In the cyclic form, there are two anomers, namely alpha and beta. In the alpha form, the C1 alcohol group is in the axial position, whereas in the beta form, the C1 alcohol group is in the equatorial position. In particular, "mannose" refers to the cyclic six-membered pyranose, more in particular the D-isomer and even more particularly the alpha-D-form (α-D-mannose). The structure and numbering of mannose on non-limiting examples of stereochemical illustration. In the current formulation, the mannose residue is a single sugar that is connected to the backbone of the polymer via a single site such as the primary alcohols that attach to C1-C4 and C6. Thus, one of the alcohols is used to connect the mannose to the polymer while the other alcohols remain OH groups at neutral pH. In several embodiments, the advantageous polyfunctionality of the approaches disclosed herein comes, at least in part, from the multiple monomers that are used to decorate the side of the polymer.

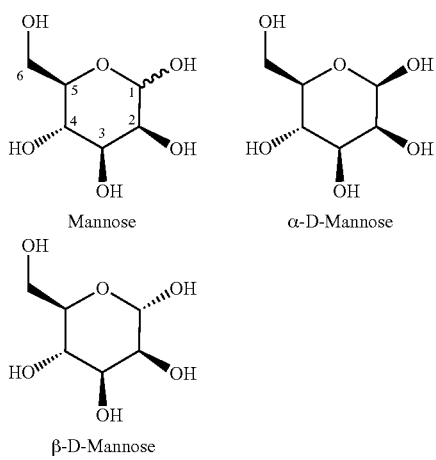

Mannose
α-D-Mannose
β-D-Mannose

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from $C_{1-6}$ alkyl, $C_{1-6}$ alkenyl, $C_{1-6}$ alkynyl, $C_{1-6}$ cycloalkyl, $C_{1-6}$ aryl, $C_{1-6}$ heteroaryl, $C_{1-6}$ heterocyclyl, $C_{1-6}$ alkoxy, $C_{1-6}$ acyl, cyano, hydroxyl, an amino, halogen substituted $C_{1-6}$alkyl, halogen substituted $C_{1-6}$alkoxy, and halogen.

As used herein, a "chemical modification" refers to a change in the naturally-occurring chemical structure of one or more amino acids of a polypeptide. Such modifications can be made to a side chain or a terminus, e.g., changing the amino-terminus or carboxyl terminus. In some embodiments, the modifications are useful for creating chemical groups that can conveniently be used to link the polypeptides to other materials, or to attach a therapeutic agent.

"Conservative changes" can generally be made to an amino acid sequence without altering activity. These changes are termed "conservative substitutions" or mutations; that is, an amino acid belonging to a grouping of amino acids having a particular size or characteristic can be substituted for another amino acid. Substitutes for an amino acid sequence can be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such substitutions are not expected to substantially affect apparent molecular weight as determined by polyacrylamide gel electrophoresis or isoelectric point. Conservative substitutions also include substituting optical isomers of the sequences for other optical isomers, specifically d amino acids for l amino acids for one or more residues of a sequence. Moreover, all of the amino acids in a sequence can undergo a d to l isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free —$NH_2$. Yet another type of conservative substitution constutes the case where amino acids with desired chemical relativities are introduced to impart reactive sites for chemical conjugation reactions, if the need for chemical derivatization arises. Such amino acids include but are not limited to Cys (to insert a sulfhydryl group), Lys (to insert a primary amine), Asp and Glu (to insert a carboxylic acid group), or specialized noncanonical amino acids containing ketone, azide, alkyne, alkene, and tetrazine side-chains. Conservative substitutions or additions of free —$NH_2$ or —SH bearing amino acids can be particularly advantageous for chemical conjugation with the linkers and mannosylating moieties of Formula 1. Moreover, point mutations, deletions, and insertions of the polypeptide sequences or corresponding nucleic acid sequences can in some cases be made without a loss of function of the polypeptide or nucleic acid fragment. Substitutions can include, e.g., 1, 2, 3, 4, 5, 6, 7, 8, 9, 10, 15, 20, 25, 30, 35, 40, 45, 50 or more residues (including any number of substitutions between those listed). A variant usable in embodiments herein may exhibit a total number of up to 200 (e.g., up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200, including any number in between those listed) changes in the amino acid sequence (e.g., exchanges, insertions, deletions, N-terminal truncations, and/or C-terminal truncations). In several embodiments, the number of changes is greater than 200. Additionally, in several embodiments, the variants include polypeptide sequences or corresponding nucleic acid sequences that exhibit a degree of functional equivalence with a reference (e.g., unmodified or native sequence). In several embodiments, the variants exhibit about 80%, about 85%, about 90%, about 95%, about 97%, about 98%, about 99% functional equivalence to an unmodified or native reference sequence (and any degree of functional equivalence between those listed). The amino acid residues described herein employ either the single letter amino acid designator or the three-letter abbreviation in keeping with the standard polypeptide nomenclature, *J. Biol. Chem.*, (1969), 243, 3552-3559. All amino acid residue sequences are represented herein by formulae with left and right orientation in the conventional direction of amino-terminus to carboxy-terminus.

The term "liver-targeting moiety" refers to mannose moieties having the ability to direct, e.g., a polypeptide, to the cells of a liver expressing mannose receptors. The liver comprises different cell types, including but not limited to hepatocytes, sinusoidal epithelial cells, Kupffer cells, stellate cells, and/or dendritic cells. Typically, a liver-targeting moiety directs a polypeptide to one or more of these cells. On the surface of the respective liver cells, receptors are present which recognize and specifically bind the liver-targeting moiety. Liver-targeting can be achieved by chemical conjugation of an antigen or ligand to a mannosylating or mannansylating moiety. Naturally occurring desilylated proteins are not encompassed within the scope of certain embodiments of the present disclosure.

The term "random copolymer" refers to the product of simultaneous polymerization of two or more monomers in admixture, where the probability of finding a given monomeric unit at any given site in a polymer chain is independent of the nature of the neighboring units at that position (Bernoullian distribution). Thus, when the variable group identified as Wp represents a random copolymer, the chain can comprise any sequence from 2 up to about 150 W1 and W2 groups, such as: —W1-W2-W1-W2-; —W2-W1-W2-W1-; —W1-W1-W1-W2-; —W1-W1-W2-W2-; —W1-W2-W2-W1-; —W1-W2-W1-W2-W2-W1-W2-W1-; —W1-W1-W2-W2-W1-W2-W2-W1-; and W2-W2-W1-W2-W1-W1-W1-W2-W2-W1-W2-W2-W1; ad infinitum, where Z attached to the various W1 groups and the W1 and W2 groups themselves can be the same or different.

The term "sequence identity" is used with regard to polypeptide (or nucleic acid) sequence comparisons. This expression in particular refers to a percentage of sequence identity, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Particularly, the polypeptide in question and the reference polypeptide exhibit the indicated sequence identity over a continuous stretch of 20, 30, 40, 45, 50, 60, 70, 80, 90, 100 or more amino acids (or any range derivable therein) or over the entire length of the reference polypeptide.

"Specific binding," as that term is commonly used in the biological arts, refers to a molecule that binds to a target with a relatively high affinity as compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and certain protein-receptor interactions; while such molecules might bind tissues besides their specific targets from time to time, to the extent that such non-target binding is inconsequential, the high-affinity binding pair can still fall within the definition of specific binding.

The term "unwanted immune response" refers to a reaction by the immune system of a subject, which in the given situation is not desirable. The reaction of the immune system is unwanted if such reaction does not lead to the prevention, reduction, or healing of a disease or disorder but instead causes, enhances or worsens, or is otherwise associated with induction or worsening of a disorder or disease. Typically, a reaction of the immune system causes, enhances or worsens a disease if it is directed against an inappropriate target. Exemplified, an unwanted immune response includes but is not limited to transplant rejection, immune response against a therapeutic agent, autoimmune disease, and allergy or hypersensitivity.

The term "variant" is to be understood as a protein (or nucleic acid) which differs in comparison to the protein from which it is derived by one or more changes in its length, sequence, or structure. The polypeptide from which a protein variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence or structure in comparison to the parent molecule. Also encompassed are modified molecules such as but not limited to post-translationally modified proteins (e.g. glycosylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Naturally occurring and artificially constructed variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, e.g., is functionally active. A variant can be characterized by a certain degree of sequence identity to the parent polypeptide from which it is derived. More precisely, a protein variant in the context of the present disclosure may exhibit at least 80% sequence identity to its parent polypeptide. Preferably, the sequence identity of protein variants is over a continuous stretch of 20, 30, 40, 45, 50, 60, 70, 80, 90, 100 or more amino acids. As discussed above, in several embodiments variants exhibit about 80%, about 85%, about 90%, about 95%, about 97%, about 98%, about 99% functional equivalence to an unmodified or native reference sequence (and any degree of functional equivalence between those listed).

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIGS. 1A-1G. OVA-p(Man) induces T cell deletion. BLK6 mice were treated with saline, or 10 µg of OVA in the form of free OVA or OVA conjugated to p(Man) (OVA-p(Man)) one day and 7 days after an adoptive transfer of 7.0×105 OTI and OTII T cells. The mice were challenged with an intradermal injection of LSP and OVA on 14 days after the initial OTI and OTII T cell transfer, then the immune response in the draining lymph nodes (dLNs) was assessed on day 19 via flow cytometry. FIG. 1A Fraction of OTII T cells in the dLNs on day 19. FIG. 1B Fraction of OTI T cells in the dLNs on day 19. FIG. 1C Fraction of OTII T cells in the liver on day 19. FIG. 1D Fraction of OTI T cells in the liver on day 19. FIG. 1E Fraction of Tregs in the dLN on day 19. FIG. 1F Fraction of Tregs in the liver on day 19.

FIG. 1G Fraction of T follicular helper cells (Tfh) as a fraction of total CD4 T cells in the dLNs on day 19.

FIGS. 2A-2B: OVA-p(Man) induces T cells Anergy in DLs. BLK6 mice were treated with saline, or 10 μg of OVA in the form of free OVA or OVA conjugated to p(Man) (OVA-p(Man)) one day and 7 days after an adoptive transfer of 7.0×105 OTI and OTII T cells. The mice were challenged with an intradermal injection of LPS and OVA on 14 days after the initial OTI and OTII T cell transfer, and immune response in the draining lymph nodes (dLNs) was assessed on day 19. Cells from the dLN were restimulated with OVA (A) or SIINFEKL (peptide) for 6 hours, then the percentage of IFN-γ producing cells was determined by flow cytometry. FIG. 2A Percentage of IFN-γ producing CD4+ T cells in the dLNs. FIG. 2B Percentage of IFN-γ producing CD8+ T cells in the dLNs.

FIGS. 3A-3D. Tolerance induction to protein therapeutics. Five BALB/c mice per group were injected with 2.5 μg of asparaginase formulated as free asparaginase (ASNase) or conjugated to p(Man) (ASNase-p(Man)) once a week for 3 weeks and then were switched to 15 μg of ASNase i.v. one a week for 8 weeks. During the initial 3 weeks ASNase-p(Man) was administered via either i.v. or subcutaneous injection. Sera was taken from the mice and monitored weekly for the presence of αASNase. FIG. 3A Pan IgG αASNase titers of mice treated with ASNase and ASNase-p(Man) via i.v. and subcutaneous injection. FIG. 3B αASNase IgG1 titers of treatment groups on day 38. FIG. 3C αASNase IgG2a titers of treatment groups on day 38. FIG. 3D αASNase IgG2b titers of treatment groups on day 38. FIG. 3E. αASNase IgG3 titers of treatment groups on day 38.

FIGS. 4A-4B. Response to p(Man) conjugates. FIG. 4A Bone marrow of animals treated with ASNase-p(Man) had fewer αASNase plasma cells than animals that were treated with ASNase. FIG. 4B Spleens of animals treated with ASNase-p(Man) had a greater percentage of IL-10 producing B regulatory cells.

FIG. 5. Tolerance induction to protein therapeutics. FIG. 5 is a graph depicting tolerance induction to the protein therapeutic asparaginase conjugated to p(Man) linker and mannose. Five BALB/c mice per group were injected with 2.5 μg of asparaginase formulated as free asparaginase (ASNase) or conjugated to p(Man) (ASNase-p(Man)) once a week for 3 weeks and then were switched to 15 μg of ASNase i.v. one a week for 7 weeks. Sera was taken from the mice and monitored weekly for the presence of anti-ASNase. Over the entire time of analysis none of the animals treated with ASNase-p(Man) developed measureable levels of antibodies against ASNase.

FIG. 6 p(Man)-ASNase administration regimen for assessment of p(Man)-protein conjugates on anti-asparaginase (anti-ASNase) humoral immune response.

FIGS. 7A-7B. Assessment of p(Man)-protein conjugates on anti-asparaginase (anti-ASNase) humoral immune response. FIG. 7A is a graph depicting serum asparagine concentration for days 71, 73, and 76. Mice treated with only saline or p(Man)-ASNase have a significantly lower serum asparagine concentration as compared to animals that had been treated with saline and then administered wt ASNase. FIG. 7B is a graph depicting serum asparagine concentration vs the anti-ASNase titer for each animal in the study. A strong correlation (r=0.8) between serum asparagine concentration and anti-ASNase titer is evident.

DETAILED DESCRIPTION

Several embodiments disclosed herein overcome the deficiencies of the prior art by providing compositions comprising mannose-fused antigens. The compositions may be used to prevent immunity or reduce an immune response protein-based drugs that would otherwise elicit an immune response.

Multiple mannose binding receptors are expressed by antigen presenting cells (APCs) and serve as gateways for antigen uptake and antigen cross presentation by these cells to T cells. Antigens taken up by APCs and presented to T cells in the absence of co-stimulation leads to T cell deletion, inactivity, and the formation of T regulator cells, that control antigen specific immune responses.

The present disclosure provides, in several embodiments, certain therapeutic compositions that are targeted for delivery to (and for uptake by) antigen presenting cells, particularly hepatocytes, LSECs, Kupffer cells and/or stellate cells, more particularly hepatocytes and/or LSECs, and even more particularly to specifically bind mannose-binding receptors.

Liver targeting facilitates two mechanisms of treatment: tolerization and clearance. Tolerization takes advantage of the liver's role in clearing apoptotic cells and processing their proteins to be recognized by the immune system as "self," as well as the liver's role in sampling peripheral proteins for immune tolerance. Clearance takes advantage of the liver's role in blood purification by rapidly removing and breaking down toxins, polypeptides and the like. Targeting of these compositions to the liver is accomplished by a mannosating moiety. The mannosylating moiety is chemically conjugated. The antigen can be endogenous (a self-antigen) or exogenous (a foreign antigen), including but not limited to: a foreign transplant antigen against which transplant recipients develop an unwanted immune response (e.g., transplant rejection), a foreign food, animal, plant or environmental antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease), or a tolerogenic portion (e.g., a fragment or an epitope) thereof; these compositions are useful for inducing tolerization to the antigen. Accordingly, the compositions of the present disclosure can be used for treating an unwanted immune response, e.g., transplant rejection, an immune response against a therapeutic agent, an autoimmune disease, and/or an allergy, depending on the embodiment. Also provided are pharmaceutical compositions containing a therapeutically effective amount of a composition of the disclosure admixed with at least one pharmaceutically acceptable excipient. In another aspect, the disclosure provides methods for the treatment of an unwanted immune response, such as transplant rejection, response against a therapeutic agent, autoimmune disease or allergy.

B. CHEMICAL DEFINITIONS

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

As used herein, the term "amino" means —NH2; the term "nitro" means —NO2; the term "halo" or "halogen" designates —F, —Cl, —Br or —I; the term "mercapto" means —SH; the term "cyano" means —CN; the term "azido" means —N3; the term "silyl" means —SiH3, and the term "hydroxy" means —OH. In certain embodiments, a halogen may be —Br or —I.

As used herein, a "monovalent anion" refers to anions of a −1 charge. Such anions are well-known to those of skill in the art. Non-limiting examples of monovalent anions include halides (e.g., F—, Cl—, Br— and I—), NO2-, NO3-, hydroxide (OH—) and azide (N3-).

As used herein, the structure indicates that the bond may be a single bond or a double bond. Those of skill in the chemical arts understand that in certain circumstances, a double bond between two particular atoms is chemically feasible and in certain circumstances, a double bond is not. The present invention therefore contemplates that a double bond may be formed only when chemically feasible.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted Cn-alkyl, and heteroatom-substituted Cn-alkyl. In certain embodiments, lower alkyls are contemplated. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The term "lower alkyl" refers to alkyls of 1-6 carbon atoms (that is, 1, 2, 3, 4, 5 or 6 carbon atoms). The term "heteroatom-unsubstituted Cn-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted C1-C10-alkyl has 1 to 10 carbon atoms. The groups, —CH3 (Me), —CH2CH3 (Et), —CH2CH2CH3 (n-Pr), —CH(CH3)2 (iso-Pr), —CH(CH2)2 (cyclopropyl), —CH2CH2CH2CH3 (n-Bu), —CH(CH3)CH2CH3 (sec-butyl), —CH2CH(CH3)2 (iso-butyl), —C(CH3)3 (tert-butyl), —CH2C(CH3)3 (neo-pentyl), cyclobutyl, cyclopentyl, and cyclohexyl, are all non-limiting examples of heteroatom-unsubstituted alkyl groups. The term "heteroatom-substituted Cn-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C1-C10-alkyl has 1 to 10 carbon atoms. The following groups are all non-limiting examples of heteroatom-substituted alkyl groups: trifluoromethyl, —CH2F, —CH2Cl, —CH2Br, —CH2OH, —CH2OCH3, —CH2OCH2CF3, —CH2OC(O)CH3, —CH2NH2, —CH2NHCH3, —CH2N(CH3)2, —CH2CH2Cl, —CH2CH2OH, CH2CH2OC(O)CH3, —CH2CH2NHCO2C(CH3)3, and —CH2Si(CH3)3.

As used herein, the term "alkylene" refers to a bivalent fully saturated straight chain aliphatic hydrocarbon group. Examples of alkylene groups include, but are not limited to, methylene, ethylene, propylene, butylene, pentylene hexylene, heptylene and octylene. An alkylene group may be represented by ⌇⌇⌇ , followed by the number of carbon atoms, followed by a "*". For example,

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 4 carbon atoms. An alkylene group may be substituted or unsubstituted. For example, a lower alkylene group can be substituted by replacing one or more hydrogen of the lower alkylene group and/or by substituting both hydrogens on the same carbon with a C3-6 monocyclic cycloalkyl group (e.g.,

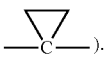).

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted Cn-alkenyl, and heteroatom-substituted Cn-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted Cn-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted C2-C10-alkenyl has 2 to 10 carbon atoms. Heteroatom-unsubstituted alkenyl groups include: —CH═CH2 (vinyl), —CH═CHCH3, —CH═CHCH2CH3, —CH2CH═CH2 (allyl), —CH2CH═CHCH3, and —CH═CH—C6H5. The term "heteroatom-substituted Cn-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C2-C10-alkenyl has 2 to 10 carbon atoms. The groups, —CH=CHF, —CH=CHCl and —CH=CHBr, are non-limiting examples of heteroatom-substituted alkenyl groups.

The term "aryl" includes heteroatom-unsubstituted aryl, heteroatom-substituted aryl, heteroatom-unsubstituted Cn-aryl, heteroatom-substituted Cn-aryl, heteroaryl, heterocyclic aryl groups, carbocyclic aryl groups, biaryl groups, and single-valent radicals derived from polycyclic fused hydrocarbons (PAHs). The term "heteroatom-unsubstituted Cn-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C6-C10-aryl has 6 to 10 carbon atoms. Non-limiting examples of heteroatom-unsubstituted aryl groups include phenyl (Ph), methylphenyl, (dimethyl)phenyl, —C6H4CH2CH3, —C6H4CH2CH2CH3, —C6H4CH(CH3)2, —C6H4CH(CH2)2, —C6H3(CH3)CH2CH3, —C6H4CH=CH2, —C6H4CH=CHCH3, —C6H4C≡CH, —C6H4C≡CCH3, naphthyl, and the radical derived from biphenyl. The term "heteroatom-substituted Cn-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C1-C10-heteroaryl has 1 to 10 carbon atoms. Non-limiting examples of heteroatom-substituted aryl groups include the groups: —C6H4F, —C6H4Cl, —C6H4Br, —C6H4I, —C6H4OH, —C6H4OCH3, —C6H4OCH2CH3, —C6H4OC(O)CH3, —C6H4NH2, —C6H4NHCH3, —C6H4N(CH3)2, —C6H4CH2OH, —C6H4CH2OC(O)CH3, —C6H4CH2NH2, —C6H4CF3, —C6H4CN, —C6H4CHO, —C6H4CHO, —C6H4C(O)CH3, —C6H4C(O)C6H5, —C6H4CO2H, —C6H4CO2CH3, —C6H4CONH2, —C6H4CONHCH3, —C6H4CON(CH3)2, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- or penta-substituted with one or more heteroatom-containing substitutents.

The term "aralkyl" includes heteroatom-unsubstituted aralkyl, heteroatom-substituted aralkyl, heteroatom-unsubstituted Cn-aralkyl, heteroatom-substituted Cn-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The term "heteroatom-unsubstituted Cn-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted C7-C10-aralkyl has 7 to 10 carbon atoms. Non-limiting examples of heteroatom-unsubstituted aralkyls are: phenylmethyl (benzyl, Bn) and phenylethyl. The term "heteroatom-substituted Cn-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted C2-C10-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted Cn-acyl, heteroatom-substituted Cn-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted Cn-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted C1-C10-acyl has 1 to 10 carbon atoms. The groups, —CHO, —C(O)CH3, —C(O)CH2CH3, —C(O)CH2CH2CH3, —C(O)CH(CH3)2, —C(O)CH(CH2)2, —C(O)C6H5, —C(O)C6H4CH3, —C(O)C6H4CH2CH3, and —COC6H3(CH3)2, are non-limiting examples of heteroatom-unsubstituted acyl groups. The term "heteroatom-substituted Cn-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted C1-C10-acyl has 1 to 10 carbon atoms. The groups, —C(O)CH2CF3, —CO2H, —CO2-, —CO2CH3, —CO2CH2CH3, —CO2CH2CH2CH3, —CO2CH(CH3)2, —CO2CH(CH2)2, —C(O)NH2 (carbamoyl), —C(O)NHCH3, —C(O)NHCH2CH3, —CONHCH(CH3)2, —CONHCH(CH2)2, —CON(CH3)2, and —CONHCH2CF3, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted Cn-alkoxy, and heteroatom-substituted Cn-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted Cn-alkoxy" refers to a group, having the structure —OR, in which R is a heteroatom-unsubstituted Cn-alkyl, as that term is defined above. Heteroatom-unsubstituted alkoxy groups include: —OCH3, —OCH2CH3, —OCH2CH2CH3, —OCH(CH3)2, and —OCH(CH2)2. The term "heteroatom-substituted Cn-alkoxy" refers to a group, having the structure —OR, in which R is a heteroatom-substituted Cn-alkyl, as that term is defined above. For example, —OCH2CF3 is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted Cn-alkenyloxy, and heteroatom-substituted Cn-alkenyloxy. The term "heteroatom-unsubstituted Cn-alkenyloxy" refers to a group, having the structure —OR, in which R is a heteroatom-unsubstituted Cn-alkenyl, as that term is defined above. The term "heteroatom-substituted Cn-alkenyloxy" refers to a group, having the structure —OR, in which R is a heteroatom-substituted Cn-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted Cn-alkynyloxy, and heteroatom-substituted Cn-alkynyloxy. The term "heteroatom-unsubstituted Cn-alkynyloxy" refers to a group, having the structure —OR, in which R is a heteroatom-unsubstituted Cn-alkynyl, as that term is defined above. The term "heteroatom-substituted Cn-alkynyloxy" refers to a group, having the structure —OR, in which R is a heteroatom-substituted Cn-alkynyl, as that term is defined above.

The term "aryloxy" includes heteroatom-unsubstituted aryloxy, heteroatom-substituted aryloxy, heteroatom-unsubstituted Cn-aryloxy, heteroatom-substituted Cn-aryloxy, heteroaryloxy, and heterocyclic aryloxy groups. The term "heteroatom-unsubstituted Cn-aryloxy" refers to a group, having the structure —OAr, in which Ar is a heteroatom-unsubstituted Cn-aryl, as that term is defined above. A non-limiting example of a heteroatom-unsubstituted aryloxy group is —OC6H5. The term "heteroatom-substituted Cn-aryloxy" refers to a group, having the structure —OAr, in which Ar is a heteroatom-substituted Cn-aryl, as that term is defined above.

The term "aralkyloxy" includes heteroatom-unsubstituted aralkyloxy, heteroatom-substituted aralkyloxy, heteroatom-unsubstituted Cn-aralkyloxy, heteroatom-substituted Cn-aralkyloxy, heteroaralkyloxy, and heterocyclic aralkyloxy groups. The term "heteroatom-unsubstituted Cn-aralkyloxy" refers to a group, having the structure —OAr, in which Ar is a heteroatom-unsubstituted Cn-aralkyl, as that term is defined above. The term "heteroatom-substituted Cn-aralkyloxy" refers to a group, having the structure —OAr, in which Ar is a heteroatom-substituted Cn-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted Cn-acyloxy, heteroatom-substituted Cn-acyloxy, alkylcarbonyloxy, arylcarbonyloxy, alkoxycarbonyloxy, aryloxycarbonyloxy, and carboxylate groups. The term "heteroatom-unsubstituted Cn-acyloxy" refers to a group, having the structure —OAc, in which Ac is a heteroatom-unsubstituted Cn-acyl, as that term is defined above. For example, —OC(O)CH3 is a non-limiting example of a heteroatom-unsubstituted acyloxy group. The term "heteroatom-substituted Cn-acyloxy" refers to a group, having the structure —OAc, in which Ac is a heteroatom-substituted Cn-acyl, as that term is defined above. For example, —OC(O)OCH3 and —OC(O)NHCH3 are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted Cn-alkylamino, and heteroatom-substituted Cn-alkylamino. The term "heteroatom-unsubstituted Cn-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted C1-C10-alkylamino has 1 to 10 carbon atoms. The term "heteroatom-unsubstituted Cn-alkylamino" includes groups, having the structure —NHR, in which R is a heteroatom-unsubstituted Cn-alkyl, as that term is defined above. A heteroatom-unsubstituted alkylamino group would include —NHCH3, —NHCH2CH3, —NHCH2CH2CH3, —NHCH(CH3)2, —NHCH(CH2)2, —NHCH2CH2CH2CH3, —NHCH(CH3)CH2CH3, —NHCH2CH(CH3)2, —NHC(CH3)3, —N(CH3)2, —N(CH3)CH2CH3, —N(CH2CH3)2, N-pyrrolidinyl, and N-piperidinyl. The term "heteroatom-substituted Cn-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted Cn-alkylamino" includes groups, having the structure —NHR, in which R is a heteroatom-substituted Cn-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted Cn-alkenylamino, heteroatom-substituted Cn-alkenylamino, dialkenylamino, and alkyl(alkenyl)amino groups. The term "heteroatom-unsubstituted Cn-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted C2-C10-alkenylamino has 2 to 10 carbon atoms. The term "heteroatom-unsubstituted Cn-alkenylamino" includes groups, having the structure —NHR, in which R is a heteroatom-unsubstituted Cn-alkenyl, as that term is defined above. The term "heteroatom-substituted Cn-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted Cn-alkenylamino" includes groups, having the structure —NHR, in which R is a heteroatom-substituted Cn-alkenyl, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted Cn-alkynylamino, heteroatom-substituted Cn-alkynylamino, dialkynylamino, alkyl(alkynyl) amino, and alkenyl(alkynyl)amino groups. The term "heteroatom-unsubstituted Cn-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted C2-C10-alkynylamino has 2 to 10 carbon atoms. The term "heteroatom-unsubstituted Cn-alkynylamino" includes groups, having the structure —NHR, in which R is a heteroatom-unsubstituted Cn-alkynyl, as that term is defined above. The term "heteroatom-substituted Cn-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted Cn-alkynylamino" includes groups, having the structure —NHR, in which R is a heteroatom-substituted Cn-alkynyl, as that term is defined above.

The term "arylamino" includes heteroatom-unsubstituted arylamino, heteroatom-substituted arylamino, heteroatom-unsubstituted Cn-arylamino, heteroatom-substituted Cn-arylamino, heteroarylamino, heterocyclic arylamino, and alkyl(aryl)amino groups. The term "heteroatom-unsubstituted Cn-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted Cn-arylamino" includes groups, having the structure —NHR, in which R is a heteroatom-unsubstituted Cn-aryl, as that term is defined above. The term "heteroatom-substituted Cn-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted Cn-arylamino" includes groups, having the structure —NHR, in which R is a heteroatom-substituted Cn-aryl, as that term is defined above.

The term "aralkylamino" includes heteroatom-unsubstituted aralkylamino, heteroatom-substituted aralkylamino, heteroatom-unsubstituted Cn-aralkylamino, heteroatom-substituted Cn-aralkylamino, heteroaralkylamino, heterocyclic aralkylamino groups, and diaralkylamino groups. The term "heteroatom-unsubstituted Cn-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted Cn-aralkylamino" includes groups, having the structure —NHR, in which R is a heteroatom-unsubstituted Cn-aralkyl, as that term is defined above. The term "heteroatom-substituted Cn-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted Cn-aralkylamino" includes groups, having the structure —NHR, in which R is a heteroatom-substituted Cn-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted Cn-amido, heteroatom-substituted Cn-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted Cn-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted Cn-amido" includes groups, having the structure —NHR, in which R is a heteroatom-unsubstituted Cn-acyl, as that term is defined above. The group, —NHC(O)CH$_3$, is a non-limiting example of a heteroatom-unsubstituted amido group. The term "heteroatom-substituted Cn-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted Cn-amido" includes groups, having the structure —NHR, in which R is a heteroatom-unsubstituted Cn-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted Cn-alkylthio, and heteroatom-substituted Cn-alkylthio. The term "heteroatom-unsubstituted Cn-alkylthio" refers to a group, having the structure —SR, in which R is a heteroatom-unsubstituted Cn-alkyl, as that term is defined above. The group, —SCH3, is an example of a heteroatom-unsubstituted alkylthio group. The term "heteroatom-substituted Cn-alkylthio" refers to a group, having the structure —SR, in which R is a heteroatom-substituted Cn-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted Cn-alkenylthio, and heteroatom-substituted Cn-alkenylthio. The term "heteroatom-unsubstituted Cn-alkenylthio" refers to a group, having the structure —SR, in which R is a heteroatom-unsubstituted Cn-alkenyl, as that term is defined above. The term "heteroatom-substituted Cn-alkenylthio" refers to a group, having the structure —SR, in which R is a heteroatom-substituted Cn-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted Cn-alkynylthio, and heteroatom-substituted Cn-alkynylthio. The term "heteroatom-unsubstituted Cn-alkynylthio" refers to a group, having the structure —SR, in which R is a heteroatom-unsubstituted Cn-alkynyl, as that term is defined above. The term "heteroatom-substituted Cn-alkynylthio" refers to a group, having the structure —SR, in which R is a heteroatom-substituted Cn-alkynyl, as that term is defined above.

The term "arylthio" includes heteroatom-unsubstituted arylthio, heteroatom-substituted arylthio, heteroatom-unsubstituted Cn-arylthio, heteroatom-substituted Cn-arylthio, heteroarylthio, and heterocyclic arylthio groups. The term "heteroatom-unsubstituted Cn-arylthio" refers to a group, having the structure —SAr, in which Ar is a heteroatom-unsubstituted Cn-aryl, as that term is defined above. The group, —$SC_6H_5$, is an example of a heteroatom-unsubstituted arylthio group. The term "heteroatom-substituted Cn-arylthio" refers to a group, having the structure —SAr, in which Ar is a heteroatom-substituted Cn-aryl, as that term is defined above.

The term "aralkylthio" includes heteroatom-unsubstituted aralkylthio, heteroatom-substituted aralkylthio, heteroatom-unsubstituted Cn-aralkylthio, heteroatom-substituted Cn-aralkylthio, heteroaralkylthio, and heterocyclic aralkylthio groups. The term "heteroatom-unsubstituted Cn-aralkylthio" refers to a group, having the structure —SAr, in which Ar is a heteroatom-unsubstituted Cn-aralkyl, as that term is defined above. The group, —$SCH_2C_6H_5$, is an example of a heteroatom-unsubstituted aralkyl group. The term "heteroatom-substituted Cn-aralkylthio" refers to a group, having the structure —SAr, in which Ar is a heteroatom-substituted Cn-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted Cn-acylthio, heteroatom-substituted Cn-acylthio, alkylcarbonyloxy, arylcarbonyloxy, alkoxycarbonyloxy, aryloxycarbonyloxy, and carboxylate groups. The term "heteroatom-unsubstituted Cn-acylthio" refers to a group, having the structure —SAc, in which Ac is a heteroatom-unsubstituted Cn-acyl, as that term is defined above. The group, —$SCOCH_3$, is an example of a heteroatom-unsubstituted acylthio group. The term "heteroatom-substituted Cn-acylthio" refers to a group, having the structure —SAc, in which Ac is a heteroatom-substituted Cn-acyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted Cn-alkylsilyl, and heteroatom-substituted Cn-alkylsilyl. The term "heteroatom-unsubstituted Cn-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted C1-C10-alkylsilyl has 1 to 10 carbon atoms. An alkylsilyl group includes dialkylamino groups. The groups, —$Si(CH_3)_3$ and —$Si(CH_3)_2C(CH_3)_3$, are non-limiting examples of heteroatom-unsubstituted alkylsilyl groups. The term "heteroatom-substituted Cn-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "phosphonate" includes straight-chain phosphonate, branched-chain phosphonate, cyclophosphonate, cyclic phosphonate, heteroatom-unsubstituted phosphonate, heteroatom-substituted phosphonate, heteroatom-unsubstituted Cn-phosphonate, and heteroatom-substituted Cn-phosphonate. The term "heteroatom-unsubstituted Cn-phosphonate" refers to a radical, having a single phosphorous atom as the point of attachment, further having a linear or branched, cyclic or acyclic structure, further having a total of n carbon atoms, 2 or more hydrogen atoms, a total of three oxygen atom, and no additional heteroatoms. The three oxygen atoms are directly attached to the phosphorous atom, with one of these oxygen atoms doubly bonded to the phosphorous atom. For example, a heteroatom-unsubstituted $C_0$-$C_{10}$-phosphonate has 0 to 10 carbon atoms. The groups, —P(O)(OH)2, —$P(O)(OH)OCH_3$, —$P(O)(OH)OCH_2CH_3$, —$P(O)(OCH_3)_2$, and —$P(O)(OH)(OC_6H_5)$ are non-limiting examples of heteroatom-unsubstituted phosphonate groups. The term "heteroatom-substituted Cn-phosphonate" refers to a radical, having a single phosphorous atom as the point of attachment, further having a linear or branched, cyclic or acyclic structure, further having a total of n carbon atoms, 2 or more hydrogen atoms, three or more oxygen atoms, three of which are directly attached to the phosphorous atom, with one of these three oxygen atoms doubly bonded to the phosphorous atom, and further having at least one additional heteroatom in addition to the three oxygen atoms, wherein each additional heteroatom is independently selected from the group consisting of N, O, F, Cl, Br, I, Si, P, and S. For example, a heteroatom-unsubstituted $C_0$-$C_{10}$-phosphonate has 0 to 10 carbon atoms.

The term "phosphinate" includes straight-chain phosphinate, branched-chain phosphinate, cyclophosphinate, cyclic phosphinate, heteroatom-unsubstituted phosphinate, heteroatom-substituted phosphinate, heteroatom-unsubstituted Cn-phosphinate, and heteroatom-substituted Cn-phosphinate. The term "heteroatom-unsubstituted Cn-phosphinate" refers to a radical, having a single phosphorous atom as the point of attachment, further having a linear or branched, cyclic or acyclic structure, further having a total of n carbon atoms, 2 or more hydrogen atoms, a total of two oxygen atom, and no additional heteroatoms. The two oxygen atoms are directly attached to the phosphorous atom, with one of these oxygen atoms doubly bonded to the phosphorous atom. For example, a heteroatom-unsubstituted C0-C10-phosphinate has 0 to 10 carbon atoms. The groups, —P(O)(OH)H, —P(O)(OH)CH3, —P(O)(OH)CH2CH3, —P(O)(OCH3)CH3, and —P(O)(OC6H5)H are non-limiting examples of heteroatom-unsubstituted phosphinate groups. The term "heteroatom-substituted Cn-phosphinate" refers to a radical, having a single phosphorous atom as the point of attachment, further having a linear or branched, cyclic or acyclic structure, further having a total of n carbon atoms, 2 or more hydrogen atoms, two or more oxygen atoms, two of which are directly attached to the phosphorous atom, with one of these two oxygen atoms doubly bonded to the phosphorous atom, and further having at least one additional heteroatom in addition to the two oxygen atoms, wherein each additional heteroatom is independently selected from the group consisting of N, O, F, Cl, Br, I, Si, P, and S. For example, a heteroatom-unsubstituted C0-C10-phosphinate has 0 to 10 carbon atoms.

Any apparently unfulfilled valency is to be understood to be properly filled by hydrogen atom(s). For example, a compound with a substituent of —O or —N is to be understood to be —OH or —NH2, respectively.

Any genus, subgenus, or specific compound discussed herein is specifically contemplated as being excluded from any embodiment described herein.

Compounds described herein may be prepared synthetically using conventional organic chemistry methods known to those of skill in the art and/or are commercially available (e.g., ChemBridge Co., San Diego, Calif.).

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like. A salt may be a pharmaceutically acceptable salt, for example. Thus, pharmaceutically acceptable salts of compounds of the present invention are contemplated.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogen phosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Compounds employed in methods may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S- or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In addition, atoms making up the compounds described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include 13C and 14C.

As noted above, compounds described herein may exist in prodrug form. As used herein, "prodrug" is intended to include any covalently bonded carriers which release the active parent drug or compounds that are metabolized in vivo to an active drug or other compounds employed in the methods described herein in vivo when such prodrug is administered to a subject. Since prodrugs are known to enhance numerous desirable qualities of pharmaceuticals (e.g., solubility, bioavailability, manufacturing, etc.), the compounds employed in some methods described herein may, if desired, be delivered in prodrug form. Thus, the invention contemplates prodrugs of compounds described herein as well as methods of delivering prodrugs. Prodrugs of the compounds employed in embodiments may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

It should be recognized that the particular anion or cation forming a part of any salt in any embodiment is not critical, so long as the salt, as a whole, is pharmacologically acceptable. Additional examples of pharmaceutically acceptable salts and their methods of preparation and use are presented in Handbook of Pharmaceutical Salts: Properties, Selection and Use (2002), which is incorporated herein by reference.

C. PHARMACEUTICAL FORMULATIONS AND ADMINISTRATION THEREOF

1. Pharmaceutical Formulations and Routes of Administration

Pharmaceutical compositions disclosed herein comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds administered according to embodiments disclosed herein may comprise different types of carriers depending on whether it is to be administered in solid, liquid or aerosol form, and whether it need to be sterile for such routes of administration as injection. Embodiments can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, systemically, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition of embodiments disclosed herein that are administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound of the present disclosure. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In some embodiments, it is contemplated that the tolerance-inducing compositions disclosed herein may be used in conjunction with the compositions for which a tolerance is being induced as part of a treatment regimen. This process may involve contacting the cell(s) with the agents at the same time or within a period of time wherein separate administration of the agents produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

Compounds discussed herein may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more tolerance-inducing compositions may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to administering the compositions for which a tolerance is being induced. In some embodiments, more than one course of therapy may be employed. It is contemplated that multiple courses may be implemented.

D. ORGANISMS AND CELL SOURCE

Cells that may be used in some methods can be from a variety of sources. Embodiments include the use of mammalian cells, such as cells from monkeys, chimpanzees, rabbits, mice, rats, ferrets, dogs, pigs, humans, and cows. Alternatively, the cells may be from fruit flies, yeast, or *E. coli*, which are all model systems for evaluating homologous recombination.

Methods can involve cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, methods can be employed in cells of the following type: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

Moreover, methods can be implemented with or in plants or parts of plants, including fruit, flowers, leaves, stems, seeds, cuttings. Plants can be agricultural, medicinal, or decorative.

E. ANTIGENS

The antigen employed as X in the compositions of Formula 1, or in any of the compositions or methods of the current disclosure, can be a protein or a peptide, e.g. the antigen may be a complete or partial therapeutic agent, a full-length transplant protein or peptide thereof, a full-length autoantigen or peptide thereof, a full-length allergen or peptide thereof, and/or a nucleic acid, or a mimetic of an aforementioned antigen. Combinations of multiple fragments may also be used, depending on the embodiment. For example, if a longer peptide identified as P has antigenic regions A, B, C, and D, compositions disclosed herein for induction of tolerance to P can comprise any combination of A, B, C, and D, and repeats of any of A, B, C, and D. A listing of any particular antigen in a category or association with any particular disease or reaction does not preclude that antigen from being considered part of another category or associated with another disease or reaction.

In several embodiments, the antigen comprises one or more therapeutic agents that are proteins, peptides, antibodies and antibody-like molecules (including antibody fragments and fusion proteins with antibodies and antibody fragments), and gene therapy vectors. These include human, non-human (such as mouse) and non-natural (e.g., engineered) proteins, antibodies, chimeric antibodies, humanized antibodies, viruses and virus-like particles, and non-antibody binding scaffolds, such as fibronectins, DARPins, knottins, and the like. In several embodiments, human allograft transplantation antigens against which transplant recipients develop an unwanted immune response are used. In several embodiments, the antigen comprises one or more self-antigens that cause an unwanted, autoimmune response. While self-antigens are of an endogenous origin in an autoimmune disease patient, according to several embodiments, the polypeptides employed in the disclosed compositions are, depending on the embodiment, synthesized exogenously (as opposed to being purified and concentrated from a source of origin).

In several embodiments, the antigen to which tolerance is desired comprises one or more foreign antigens, such as food, animal, plant and environmental antigens, against which a patient experiences an unwanted immune response. While a therapeutic protein can also be considered a foreign antigen due to its exogenous origin, for purposes of clarity in the description of the present disclosure such therapeutics are described as a separate group. Similarly, a plant or an animal antigen can be eaten and considered a food antigen, and an environmental antigen may originate from a plant. They are, however, considered foreign antigens. In the interest of simplicity no attempt will be made to describe distinguish and define all of such potentially overlapping groups, as those skilled in the art can appreciate the antigens that can be employed in the compositions of the disclosure, particularly in light of the detailed description and examples.

In several embodiments, X is selected from the group consisting of insulin, proinsulin, preproinsulin, gluten, gliadin, myelin basic protein, myelin oligodendrocyte glycoprotein and proteolipid protein, Factor VIII, Factor IX, asparaginase, uricase and fragments of any of the preceding. In several embodiments, the antigen X is not a full length protein. For example, in some embodiments, the antigen is not full length gliadin, insulin, or proinsulin. In several embodiments, the antigen is not full length myelin basic protein, not full length myelin oligodendrocyte protein, or not full length proteolipid protein. In several embodiments, the antigen X is not a fragment of a protein. As discussed in more detail below, there exist a variety of antigens to which tolerance may be desired. These may include, but are not limited to, exogenous antigens that result in an adverse immune response when a subject is exposed to the antigen.

In several embodiments, the adverse immune response could be a result of ingestion of the antigen, e.g., orally or nasally, or via some other mucosal route. These routes could be the case, for example, with food antigens. In some embodiments, the antigen may be purposefully administered to a subject, for example, with the administration of a therapeutic composition to treat a disease or condition that the subject is affected by. In still additional embodiments, the antigen may be produced by the subject, e.g., an autoimmune antigen. For example, in several embodiments, X comprises a foreign transplant antigen against which transplant recipients develop an unwanted immune response or a tolerogenic portion thereof. In several embodiments, X comprises a foreign food, animal, plant or environmental antigen against which patients develop an unwanted immune response or a tolerogenic portion thereof. In several embodiments, X comprises a foreign therapeutic agent against which patients develop an unwanted immune response or a tolerogenic portion thereof. In several embodiments, X comprises a synthetic self-antigen against the endogenous version of which patients develop an unwanted immune response or a tolerogenic portion thereof.

In further detail to the above, there are provided in several embodiments, compounds where X is a food antigen. In some such embodiments, X is one or more of conarachin (Ara h 1), allergen II (Ara h 2), arachis agglutinin, conglutin (Ara h 6), α-lactalbumin (ALA), lactotransferrin, Pen a 1 allergen (Pen a 1), allergen Pen m 2 (Pen m 2), tropomyosin fast isoform, high molecular weight glutenin, low molecular weight glutenin, alpha-gliadin, gamma-gliadin, omega-gliadin, hordein, seclain, and avenin. Fragment of any of these antigens and/or mimotopes of any of these antigens are also used, in several embodiments. In several embodiments, X is selected from the group consisting of gluten, high molecular weight glutenin, low molecular weight glutenin, alpha-gliadin, gamma-gliadin, omega-gliadin, hordein, seclain, and avenin and fragments thereof. In several embodiments, X is selected from the group consisting of gluten, high molecular weight glutenin, low molecular weight glutenin, alpha-gliadin, gamma-gliadin, and omega-gliadin and fragments thereof. In several embodiments, X is gluten or fragment thereof. In several embodiments, X is gliadin or fragment thereof.

In several embodiments, there are provided compounds where X is a therapeutic agent. In several embodiments, X is selected from the group consisting of Factor VII, Factor IX, asparaginase, and uricase and fragments thereof. In several embodiments, X is a therapeutic agent selected from the group consisting of Factor VII and Factor IX and fragments thereof. In several embodiments, X is a therapeutic agent selected from the group consisting of Factor VIII or fragment thereof. In several embodiments, when X is a therapeutic agent, the compound can be used in the treatment, prevention, reduction, or otherwise amelioration of an immune response developed against a therapeutic agent for hemophilia. As discussed herein, mimotopes of any antigenic portion of the antigens above can be used in several embodiments.

In several embodiments, X comprises asparaginase or a fragment thereof. In several embodiments, X comprises uricase or a fragment thereof. In several such embodiments, the compound can be used in the treatment, prevention, reduction, or otherwise amelioration of an immune response developed against an anti-neoplastic agent. As discussed herein, mimotopes of any antigenic portion of the antigens above can be used in several embodiments.

In several embodiments, X is associated with an autoimmune disease. For example, in several embodiments, the associated autoimmune disease is one or more of Type I diabetes, multiple sclerosis, rheumatoid arthritis, vitiligo, uveitis, pemphis vulgaris and neuromyelitis optica.

In several embodiments, the autoimmune disease is Type I diabetes and X comprises insulin or a fragment thereof. In several embodiments, the autoimmune disease is Type I diabetes and X comprises proinsulin or a fragment thereof. In several embodiments, the autoimmune disease is Type I diabetes and X comprises preproinsulin or a fragment thereof. As discussed herein, mimotopes of any antigenic portion of the antigens above can be used in several embodiments. In several embodiments, combinations of these antigens can be incorporated into the tolerogenic compound which may aid in reducing immune responses to self-antigens at multiple points along the insulin pathway.

In several embodiments, the autoimmune disease is multiple sclerosis and X comprises myelin basic protein or a fragment thereof. In several embodiments, the autoimmune disease is multiple sclerosis and X comprises myelin oligodendrocyte glycoprotein or a fragment thereof. In several embodiments, the autoimmune disease is multiple sclerosis and X comprises proteolipid protein or a fragment thereof. As discussed herein, mimotopes of any antigenic portion of the antigens above can be used in several embodiments. In several embodiments, combinations of these antigens can be incorporated into the tolerogenic compound (e.g., a mixture of antigens or fragments of MOG, MBP and/or PLP) which may aid in reducing immune responses to self-antigens at multiple points along the enzymatic pathways that control myelination or myelin repair.

As discussed herein, mimotopes of any antigenic portion of the self-antigens above (or otherwise disclosed herein) can be used in several embodiments.

In several embodiments, the pharmaceutically acceptable composition consists of, or consists essentially of a compound wherein X is a food antigen, therapeutic agent, a self antigen, or fragment thereof, a linker Y, and a liver targeting moiety Z selected from mannose and/or a mannose receptor-targeting moiety (including, but not limited to, one or more of mannosamine, N-acetylmannosamine, or N-acetylglucosamine).

The tolerogenic antigen can be a complete protein, a portion of a complete protein, a peptide, or the like, and can be derivatized (as discussed above) for attachment to a linker and/or antigen-binding moiety, can be a variant and/or can contain conservative substitutions, particularly maintaining sequence identity, and/or can be desialylated.

In the embodiments where the antigen is a therapeutic protein, peptide, antibody or antibody-like molecule, specific antigens can be selected from: Abatacept, Abciximab, Adalimumab, Adenosine deaminase, Ado-trastuzumab emtansine, Agalsidase alfa, Agalsidase beta, Aldeslukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin [including recombinant human insulin ("rHu insulin") and bovine insulin], Interferon-α2a, Interferon-α2b, Interferon-β1a, Interferon-β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Natalizumab, Octreotide, Ofatumumab, Oprelvekin, Pancreatic amylase, Pancreatic lipase, Papain, Peg-asparaginase, Peg-doxorubicin HCl, PEG-epoetin-β, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, vW factor. The therapeutic protein can be obtained from natural sources (e.g., concentrated and purified) or synthesized, e.g., recombinantly, and includes antibody therapeutics that are typically IgG monoclonal or fragments or fusions.

Particular therapeutic protein, peptide, antibody or antibody-like molecules include, but are not limited to, Abciximab, Adalimumab, Agalsidase alfa, Agalsidase beta, Aldeslukin, Alglucosidase alfa, Factor VIII, Factor IX, Infliximab, Insulin (including rHu Insulin), L-asparaginase, Laronidase, Natalizumab, Octreotide, Phenylalanine ammonia-lyase (PAL), or Rasburicase (uricase) and generally IgG monoclonal antibodies in their varying formats.

Some embodiments employ hemostatic agents (e.g., Factor VIII and IX), Insulin (including rHu Insulin), and the non-human therapeutics uricase, PAL and asparaginase.

In several embodiments, therapeutic agents are delivered through the use of, e.g., a gene therapy vector. In some such embodiments, an immune response may be developed against a portion of such vectors and/or their cargo (e.g., the therapeutic agent). Thus, in several embodiments, the antigen to which tolerance is desired comprises a gene therapy vector, including, but not limited to: adenoviruses and adeno-associated virus (and corresponding variants-1, -2, -5, -6, -8, -9, and/or other parvoviruses), lentiviruses, and retroviruses.

Unwanted immune response in hematology and transplant includes autoimmune aplastic anemia, transplant rejection (generally), and Graft vs. Host Disease (bone marrow transplant rejection). In the embodiments where the tolerogenic antigen is a human allograft transplantation antigen, specific sequences can be selected from: subunits of the various MHC class I and MHC class II haplotype proteins (for example, donor/recipient differences identified in tissue cross-matching), and single-amino-acid polymorphisms on minor blood group antigens including RhCE, Kell, Kidd, Duffy and Ss. Such compositions can be prepared individually for a given donor/recipient pair.

In type 1 diabetes mellitus, antigens include, but are not limited to: insulin, proinsulin, preproinsulin, glutamic acid decarboxylase-65 (GAD-65 or glutamate decarboxylase 2), GAD-67, glucose-6 phosphatase 2 (IGRP or islet-specific glucose 6 phosphatase catalytic subunit related protein), insulinoma-associated protein 2 (IA-2), and insulinoma-associated protein 2β (IA-2β); other antigens include ICA69, ICA12 (SOX-13), carboxypeptidase H, Imogen 38, GLIMA 38, chromogranin-A, HSP-60, carboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5, or immunogenic fragments or portions of any of such antigens. It should be noted that insulin is an example of an antigen that can be characterized both as a self-antigen and a therapeutic protein antigen. For example, rHu Insulin and bovine insulin are therapeutic protein antigens (that are the subject of unwanted immune attack), whereas endogenous human insulin is a self-antigen (that is the subject of an unwanted immune attack). Because endogenous human insulin is not available to be employed in a pharmaceutical composition, a recombinant form is employed in certain embodiments of the compositions of the disclosure.

Human insulin, including an exogenously obtained form useful in the compositions of the disclosure, has the following sequence (UNIPROT P01308):

(SEQ ID NO: 1)
MALWMRLLPLLALLALWGPDPAAAFVNQHLCGSHLVEALYLVCGERGFF

YTPKTRREAEDLQVGQVELGGGPGAGSLQPLALEGSLQKRGIVEQCCTS

ICSLYQLENYCN

GAD-65, including an exogenously obtained form useful in the compositions of the disclosure, has the following sequence (UNIPROT Q05329):

(SEQ ID NO: 2)
MASPGSGFWSFGSEDGSGDSENPGTARAWCQVAQKFTGGIGNKLCALLY

GDAEKPAESGGSQPPRAAARKAACACDQKPCSCSKVDVNYAFLHATDLL

PACDGERPTLAFLQDVMNILLQYVVKSFDRSTKVIDFHYPNELLQEYNW

ELADQPQNLEEILMHCQTTLKYAIKTGHPRYFNQLSTGLDMVGLAADWL

TSTANTNMFTYEIAPVFVLLEYVTLKKMREIIGWPGGSGDGIFSPGGAI

SNMYAMMIARFKMFPEVKEKGMAALPRLIAFTSEHSHFSLKKGAAALGI

GTDSVILIKCDERGKMIPSDLERRILEAKQKGFVPFLVSATAGTTVYGA

FDPLLAVADICKKYKIWMHVDAAWGGGLLMSRKHKWKLSGVERANSVTW

NPHKMMGVPLQCSALLVREEGLMQNCNQMHASYLFQQDKHYDLSYDTGD

KALQCGRHVDVFKLWLMWRAKGTTGFEAHVDKCLELAEYLYNIIKNREG

YEMVFDGKPQHTNVCFWYIPPSLRTLEDNEERMSRLSKVAPVIKARMME

YGTTMVSYQPLGDKVNFFRMVISNPAATHQDIDFLIEEIERLGQDL

IGRP, including an exogenously obtained form useful in the compositions of the disclosure, has the following sequence (UNIPROT QN9QR9):

(SEQ ID NO: 3)
MDFLHRNGVLIIQHLQKDYRAYYTFLNFMSNVGDPRNIFFIYFPLCFQF

NQTVGTKMIWVAVIGDWLNLIFKWILFGHRPYWWVQETQIYPNHSSPCL

EQFPTTCETGPGSPSGHAMGASCVWYVMVTAALSHTVCGMDKFSITLHR

LTWSFLWSVFWLIQISVCISRVFIATHEPHQVILGVIGGMLVAEAFEHT

PGIQTASLGTYLKTNLFLFLFAVGFYLLLRVLNIDLLWSVPIAKKWCAN

PDWIHIDTTPFAGLVRNLGVLFGLGFAINSEMFLLSCRGGNNYTLSFRL

LCALTSLTILQLYHFLQIPTHEEHLFYVLSFCKSASIPLTVVAFIPYSV

HMLMKQSGKKSQ.

In several embodiments, human proinsulin, including an exogenously obtained form useful in the tolerogenic compositions of the disclosure, has the following sequence:

```
                                         (SEQ ID NO: 4)
FVNQHLCGSHLVEALYLVCGERGFFYTPKTRREAEDLQVGQVELGGGPG
AGSLQPLALEGSLQKRGIVEQCCTSICSLYQLENYCN.
```

Depending on the embodiment, peptides/epitopes useful in the tolerogenic compositions of the disclosure for treating type 1 diabetes include some or all of the following sequences, individually in a tolerogenic composition or together in a cocktail of tolerogenic compositions:

Human Proinsulin 1-70:

```
                                         (SEQ ID NO: 5)
FVNQHLCGSHLVEALYLVCGERGFFYTPKTRREAEDLQVGQVELGGGPG
AGSLQPLALEGSLQKRGIVEQ;
```

Human Proinsulin 9-70:

```
Human Proinsulin 1-70:
                                         (SEQ ID NO: 6)
SHLVEALYLVCGERGFFYTPKTRREAEDLQVGQVELGGGPGAGSLQPLA
LEGSLQKRGIVEQ;

Human Proinsulin 9-38:
                                         (SEQ ID NO: 7)
SHLVEALYLVCGERGFFYTPKTRREAEDLQ;

Human Proinsulin 1-38:
                                         (SEQ ID NO: 8)
FVNQHLCGSHLVEALYLVCGERGFFYTPKTRREAEDLQ;

Human Proinsulin 9-23:
                                         (SEQ ID NO: 9)
SHLVEALYLVCGERG;

Human Proinsulin 45-71 (C13-A6):
                                         (SEQ ID NO: 10)
GGGPGAGSLQPLALEGSLQKRGIVEQC;

Human Proinsulin C24-A1:
                                         (SEQ ID NO: 11)
LALEGSLQKRG;

Human Proinsulin C19-A3:
                                         (SEQ ID NO: 12)
GSLQPLALEGSLQKRGIV;

Human Proinsulin C13-32:
                                         (SEQ ID NO: 13)
GGGPGAGSLQPLALEGSLQK;

Human Proinsulin B9-C4:
                                         (SEQ ID NO: 14)
SHLVEALYLVCGERGFFYTPKTRREAED;

Human Proinsulin C22-A5:
                                         (SEQ ID NO: 15)
QPLALEGSLQKRGIVEQ;

Human IA-2 718-782:
                                         (SEQ ID NO: 16)
AYQAEPNTCATAQGEGNIKKNRHPDFLPYDHARIKLKVESSPSRSDYIN
ASPIIEHDPRMPAYIA;

Human IA-2 785-819:
                                         (SEQ ID NO: 17)
GPLSHTIADFWQMVWESGCTVIVMLTPLVEDGVKQ;

Human IA-2 828-883:
                                         (SEQ ID NO: 18)
GASLYHVYEVNLVSEHIWCEDFLVRSFYLKNVQTQETRTLTQFHFLSWP
AEGTPAS;

Human IA-2 943-979:
                                         (SEQ ID NO: 19)
EHVRDQRPGLVRSKDQFEFALTAVAEEVNAILKALPQCG.
```

In autoimmune diseases of the thyroid, including Hashimoto's thyroiditis and Graves' disease, main antigens include, but are not limited to, thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor.

In Addison's Disease, main antigens include, but are not limited to, 21-hydroxylase, 17α-hydroxylase, and P450 side chain cleavage enzyme (P450scc); other antigens include ACTH receptor, P450c21 and P450c17.

In premature ovarian failure, main antigens include, but are not limited to, FSH receptor and α-enolase.

In autoimmune hypophysitis, or pituitary autoimmune disease, main antigens include, but are not limited to, pituitary gland-specific protein factor (PGSF) 1a and 2; another antigen is type 2 iodothyronine deiodinase.

In multiple sclerosis, main antigens include, but are not limited to, myelin basic protein ("MBP"), myelin oligodendrocyte glycoprotein ("MOG") and myelin proteolipid protein ("PLP").

MBP, including an exogenously obtained form useful in the compositions of the disclosure, has the following sequence (UNIPROT P02686):

```
                                         (SEQ ID NO: 20)
MGNHAGKRELNAEKASTNSETNRGESEKKRNLGELSRTTSEDNEVFGEA

DANQNNGTSSQDTAVTDSKRTADPKNAWQDAHPADPGSRPHLIRLFSRD

APGREDNTFKDRPSESDELQTIQEDSAATSESLDVMASQKRPSQRHGSK

YLATASTMDHARHGFLPRHRDTGILDSIGRFFGGDRGAPKRGSGKDSHH

PARTAHYGSLPQKSHGRTQDENPVVHFFKNIVTPRTPPPSQGKGRGLSL

SRFSWGAEGQRPGFGYGGRASDYKSAHKGFKGVDAQGTLSKIFKLGGRD

SRSGSPMARR.
```

MOG, including an exogenously obtained form useful in the compositions of the disclosure, has the following sequence (UNIPROT Q16653):

```
                                         (SEQ ID NO: 21)
MASLSRPSLPSCLCSFLLLLLLQVSSSYAGQFRVIGPRHPIRALVGDEV

ELPCRISPGKNATGMEVGWYRPPFSRVVHLYRNGKDQDGDQAPEYRGRT

ELLKDAIGEGKVTLRIRNVRFSDEGGFTCFFRDHSYQEEAAMELKVEDP

FYWVSPGVLVLLAVLPVLLLQITVGLIFLCLQYRLRGKLRAEIENLHRT

FDPHFLRVPCWKITLFVIVPVLGPLVALIICYNWLHRRLAGQFLEELRN

PF.
```

PLP, including an exogenously obtained form useful in the compositions of the disclosure, has the following sequence (UNIPROT P60201):

```
                                         (SEQ ID NO: 22)
MGLLECCARCLVGAPFASLVATGLCFFGVALFCGCGHEALTGTEKLIET

YFSKNYQDYEYLINVIHAFQYVIYGTASFFFLYGALLLAEGFYTTGAVR

QIFGDYKTTICGKGLSATVTGGQKGRGSRGQHQAHSLERVCHCLGKWLG

HPDKFVGITYALTVVWLLVFACSAVPVYIYFNTWTTCQSIAFPSKTSAS

IGSLCADARMYGVLPWNAFPGKVCGSNLLSICKTAEFQMTFHLFIAAFV

GAAATLVSLLTFMIAATYNFAVLKLMGRGTKF.
```

Peptides/epitopes useful in the compositions of the disclosure for treating multiple sclerosis include some or all of the following sequences, individually in a tolerogenic composition as disclosed herein or together in a combination (e.g., a cocktail) of tolerogenic compositions:

MBP 13-32:
KYLATASTMDHARHGFLPRH; (SEQ ID NO: 23)

MBP 83-99:
ENPWHFFKNIVTPRTP; (SEQ ID NO: 24)

MBP 111-129:
LSRFSWGAEGQRPGFGYGG; (SEQ ID NO: 25)

MBP 146-170:
AQGTLSKIFKLGGRDSRSGSPMARR; (SEQ ID NO: 26)

MOG 1-20:
GQFRVIGPRHPIRALVGDEV; (SEQ ID NO: 27)

MOG 35-55:
MEVGWYRPPFSRWHLYRNGK; (SEQ ID NO: 28)

PLP 139-154:
HCLGKWLGHPDKFVGI; (SEQ ID NO: 29)

MOG 30-60:
KNATGMEVGWYRSPFSRVVHLYRNGKDQDAE; (SEQ ID NO: 30)

MBP 83-99:
ENPVVHFFKNIVTPRTP; (SEQ ID NO: 31)

MOG 35-55:
MEVGWYRPPFSRVVHLYRNGK; (SEQ ID NO: 32)

MBP 82-98:
DENPVVHFFKNIVTPRT; (SEQ ID NO: 33)

MBP 82-99:
DENPVVHFFKNIVTPRTP; (SEQ ID NO: 34)

MBP 82-106:
DENPVVHFFKNIVTPRTPPPSQGKG; (SEQ ID NO: 35)

MBP 87-106:
VHFFKNIVTPRTPPPSQGKG; (SEQ ID NO: 36)

MBP 131-155:
ASDYKSAHKGLKGVDAQGTLSKIFK; (SEQ ID NO: 37)

PLP 41-58:
GTEKLIETYFSKNYQDYE; (SEQ ID NO: 38)

PLP 89-106:
GFYTTGAVRQIFGDYKTT; (SEQ ID NO: 39)

PLP 95-116:
AVRQIFGDYKTTICGKGLSATV; (SEQ ID NO: 40)

PLP 178-197:
NTWTTCQSIAFPSKTSASIG; (SEQ ID NO: 41)

PLP 190-209:
SKTSASIGSLCADARMYGVL; (SEQ ID NO: 42)

MOG 11-30:
PIRALVGDEVELPCRISPGK; (SEQ ID NO: 43)

MOG 21-40:
ELPCRISPGKNATGMEVGWY; (SEQ ID NO: 44)

MOG 64-86:
EYRGRTELLKDAIGEGKVTLRIR; (SEQ ID NO: 45)

MOG 1-62:
GQFRVIGPRHPIRALVGDEVELPCRISPGKNATGMEVGWYRPPFSRVVH
LYRNGKDQDGDQA (SEQ ID NO. 46)

MBP 76-136:
SHGRTQDENPVVHFFKNIVTPRTPPPSQGKGRGLSLSRFSWGAEGQRPG
FGYGGRASDYKSCG (SEQ ID NO: 47)

In rheumatoid arthritis, main antigens include, but are not limited to, collagen II, immunoglobulin binding protein, the fragment crystallizable region of immunoglobulin G, double-stranded DNA, and the natural and cirtullinated forms of proteins implicated in rheumatoid arthritis pathology, including fibrin/fibrinogen, vimentin, collagen I and II, and alpha-enolase.

In autoimmune gastritis, a main antigen is H+, K+-ATPase.

In pernicious angemis, a main antigen is intrinsic factor.

In celiac disease, main antigens include, but are not limited to, tissue transglutaminase and the natural and deamidated forms of gluten or gluten-like proteins, such as alpha-, gamma-, and omega-gliadin, glutenin, hordein, secalin, and avenin. Those skilled in the art will appreciate, for example, that while the main antigen of celiac disease is alpha gliadin, alpha gliadin turns more immunogenic in the body through deamidation by tissue glutaminase converting alpha gliadin's glutamines to glutamic acid. Thus, while alpha gliadin is originally a foreign food antigen, once it has been modified in the body to become more immunogenic it can be characterized as a self-antigen, depending on the embodiment.

In vitiligo, a main antigen is tyrosinase, and tyrosinase related protein 1 and 2.

MART1, Melanoma antigen recognized by T cells 1, Melan-A, including an exogenously obtained form useful in the compositions of the disclosure, has the following sequence (UNIPROT Q16655):

MPREDAHFIYGYPKKGHGHSYTTAEEAAGIGILTVILGVLLLIGCWYCR
RRNGYRALMDKSLHVGTQCALTRRCPQEGFDHRDSKVSLQEKNCEPVVP
NAPPAYEKLSAEQSPPPYSP. (SEQ ID NO: 48)

Tyrosinase, including an exogenously obtained form useful in the compositions of the disclosure, has the following sequence (UNIPROT P14679):

(SEQ ID NO: 49)
MLLAVLYCLLWSFQTSAGHFPRACVSSKNLMEKECCPPWSGDRSPCGQL

SGRGSCQNILLSNAPLGPQFPFTGVDDRESWPSVFYNRTCQCSGNFMGF

NCGNCKFGFWGPNCTERRLLVRRNIFDLSAPEKDKFFAYLTLAKHTISS

DYVIPIGTYGQMKNGSTPMENDINIYDLFVWMHYYVSMDALLGGSEIWR

DIDFAHEAPAFLPWHRLFLLRWEQEIQKLTGDENFTIPYWDWRDAEKCD

ICTDEYMGGQHPTNPNLLSPASFFSSWQIVCSRLEEYNSHQSLCNGTPE

GPLRRNPGNHDKSRTPRLPSSADVEFCLSLTQYESGSMDKAANFSFRNT

LEGFASPLTGIADASQSSMHNALHIYMNGTMSQVQGSANDPIFLLHHAF

VDSIFEQWLRRHRPLQEVYPEANAPIGHNRESYMVPFIPLYRNGDFFIS

SKDLGYDYSYLQDSDPDSFQDYIKSYLEQASRIWSWLLGAAMVGAVLTA

LLAGLVSLLCRHKRKQLPEEKQPLLMEKEDYHSLYQSHL

Melanocyte protein PMEL, gp100, including an exogenously obtained form useful in the compositions of the disclosure, has the following sequence (UNIPROT P40967):

(SEQ ID NO: 50)
MDLVLKRCLLHLAVIGALLAVGATKVPRNQDWLGVSRQLRTKAWNRQLY

PEWTEAQRLDCWRGGQVSLKVSNDGPTLIGANASFSIALNFPGSQKVLP

DGQVIWVNNTIINGSQVWGGQPVYPQETDDACIFPDGGPCPSGSWSQKR

SFVYVWKTWGQYWQVLGGPVSGLSIGTGRAMLGTHTMEVTVYHRRGSRS

YVPLAHSSSAFTITDQVPFSVSVSQLRALDGGNKHFLRNQPLTFALQLH

DPSGYLAEADLSYTWDFGDSSGTLISRALVVTHTYLEPGPVTAQVVLQA

AIPLTSCGSSPVPGTTDGHRPTAEAPNTTAGQVPTTEVVGTTPGQAPTA

EPSGTTSVQVPTTEVISTAPVQMPTAESTGMTPEKVPVSEVMGTTLAEM

STPEATGMTPAEVSIVVLSGTTAAQVTTTEWVETTARELPIPEPEGPDA

SSIMSTESITGSLGPLLDGTATLRLVKRQVPLDCVLRYGSFSVTLDIV

QGIESAEILQAVPSGEGDAFELTVSCQGGLPKEACMEISSPGCQPPAQR

LCQPVLPSPACQLVLHQILKGGSGTYCLNVSLADTNSLAVVSTQLIMPG

QEAGLGQVPLIVGILLVLMAVVLASLIYRRRLMKQDFSVPQLPHSSSHW

LRLPRIFCSCPIGENSPLLSGQQV.

In myasthenia gravis, a main antigen is acetylcholine receptor.

In pemphigus vulgaris and variants, main antigens include, but are not limited to, desmoglein 3, 1 and 4; other antigens include pemphaxin, desmocollins, plakoglobin, perplakin, desmoplakins, and acetylcholine receptor.

In bullous pemphigoid, main antigens include BP180 and BP230; other antigens include plectin and laminin 5.

In dermatitis herpetiformis Duhring, main antigens include, but are not limited to, endomysium and tissue transglutaminase.

In epidermolysis bullosa acquisita, a main antigen is collagen VII.

In systemic sclerosis, main antigens include, but are not limited to, matrix metalloproteinase 1 and 3, the collagen-specific molecular chaperone heat-shock protein 47, fibrillin-1, and PDGF receptor; other antigens include Scl-70, U1 RNP, Th/To, Ku, Jo1, NAG-2, centromere proteins, topoisomerase I, nucleolar proteins, RNA polymerase I, II and III, PM-Slc, fibrillarin, and B23.

In mixed connective tissue disease, a main antigen is U1snRNP.

In Sjogren's syndrome, the main antigens include, but are not limited to, nuclear antigens SS-A and SS-B; other antigens include fodrin, poly(ADP-ribose) polymerase and topoisomerase, muscarinic receptors, and the Fc-gamma receptor IIIb.

In systemic lupus erythematosus, main antigens include nuclear proteins including the "Smith antigen," SS-A, high mobility group box 1 (HMGB1), nucleosomes, histone proteins and double-stranded DNA (against which autoantibodies are made in the disease process).

In Goodpasture's syndrome, main antigens include, but are not limited to, glomerular basement membrane proteins including collagen IV.

In rheumatic heart disease, a main antigen is cardiac myosin.

In autoimmune polyendocrine syndrome type 1 antigens include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega.

In neuromyelitis optica, a main antigen is AQP4.

Aquaporin-4, including an exogenously obtained form useful in the compositions of the disclosure, has the following sequence (UNIPROT P55087):

(SEQ ID NO: 51)
MSDRPTARRWGKCGPLCTRENIMVAFKGVWTQAFWKAVTAEFLAMLIFV

LLSLGSTINWGGTEKPLPVDMVLISLCFGLSIATMVQCFGHISGGHINP

AVTVAMVCTRKISIAKSVFYIAAQCLGAIIGAGILYLVTPPSVVGGLGV

TMVHGNLTAGHGLLVELIITFQLVFTIFASCDSKRTDVTGSIALAIGFS

VAIGHLFAINYTGASMNPARSFGPAVIMGNWENHWIYWVGPIIGAVLAG

GLYEYVFCPDVEFKRRFKEAFSKAAQQTKGSYMEVEDNRSQVETDDLIL

KPGVVHVIDVDRGEEKKGKDQSGEVLSSV.

In uveitis, main antigens include Retinal S-antigen or "S-arrestin" and interphotoreceptor retinoid binding protein (IRBP) or retinol-binding protein 3.

S-arrestin, including an exogenously obtained form useful in the compositions of the disclosure, has the following sequence (UNIPROT P10523):

(SEQ ID NO: 52)
MAASGKTSKSEPNHVIFKKISRDKSVTIYLGNRDYIDHVSQVQPVDGVV

LVDPDLVKGKKVYVTLTCAFRYGQEDIDVIGLTFRRDLYFSRVQVYPPV

GAASTPTKLQESLLKKLGSNTYPFLLTFPDYLPCSVMLQPAPQDSGKSC

GVDFEVKAFATDSTDAEEDKIPKKSSVRLLIRKVQHAPLEMGPQPRAEA

AWQFFMSDKPLHLAVSLNKEIYFHGEPIPVTVTVTNNTEKTVKKIKAFV

EQVANVVLYSSDYYVKPVAMEEAQEKVPPNSTLTKTLTLLPLLANNRER

RGIALDGKIKHEDTNLASSTIIKEGIDRTVLGILVSYQIKVKLTVSGFL

-continued

```
GELTSSEVATEVPFRLMHPQPEDPAKESYQDANLVFEEFARHNLKDAGE

AEEGKRDKNDVDE.
```

IRBP, including an exogenously obtained form useful in the compositions of the disclosure, has the following sequence (UNIPROT P10745):

```
                                        (SEQ ID NO: 53)
MMREWVLLMSVLLCGLAGPTHLFQPSLVLDMAKVLLDNYCFPENLLGMQ

EAIQQAIKSHEILSISDPQTLASVLTAGVQSSLNDPRLVISYEPSTPEP

PPQVPALTSLSEEELLAWLQRGLRHEVLEGNVGYLRVDSVPGQEVLSMM

GEFLVAHVWGNLMGTSALVLDLRHCTGGQVSGIPYIISYLHPGNTILHV

DTIYNRPSNTTTEIWTLPQVLGERYGADKDVVVLTSSQTRGVAEDIAHI

LKQMRRAIVVGERTGGGALDLRKLRIGESDFFFTVPVSRSLGPLGGGSQ

TWEGSGVLPCVGTPAEQALEKALAILTLRSALPGVVHCLQEVLKDYYTL

VDRVPTLLQHLASMDFSTVVSEEDLVTKLNAGLQAASEDPRLLVRAIGP

TETPSWPAPDAAAEDSPGVAPELPEDEAIRQALVDSVFQVSVLPGNVGY

LRFDSFADASVLGVLAPYVLRQVWEPLQDTEHLIMDLRHNPGGPSSAVP

LLLSYFQGPEAGPVHLFTTYDRRTNITQEHFSHMELPGPRYSTQRGVYL

LTSHRTATAAEEFAFLMQSLGWATLVGEITAGNLLHTRTVPLLDTPEGS

LALTVPVLTFIDNHGEAWLGGGVVPDAIVLAEEALDKAQEVLEFHQSLG

ALVEGTGHLLEAHYARPEVVGQTSALLRAKLAQGAYRTAVDLESLASQL

TADLQEVSGDHRLLVFHSPGELVVEEAPPPPPAVPSPEELTYLIEALFK

TEVLPGQLGYLRFDAMAELETVKAVGPQLVRLVWQQLVDTAALVIDLRY

NPGSYSTAIPLLCSYFFEAEPRQHLYSVFDRATSKVTEVWTLPQVAGQR

YGSHKDLYILMSHTSGSAAEAFAHTMQDLQRATVIGEPTAGGALSVGIY

QVGSSPLYASMPTQMAMSATTGKAWDLAGVEPDITVPMSEALSIAQDIV

ALRAKVPTVLQTAGKLVADNYASAELGAKMATKLSGLQSRYSRVTSEVA

LAEILGADLQMLSGDPHLKAAHIPENAKDRIPGIVPMQIPSPEVFEELI

KFSFHTNVLEDNIGYLRFDMFGDGELLTQVSRLLVEHIWKKIMHTDAMI

IDMRFNIGGPTSSIPILCSYFFDEGPPVLLDKIYSRPDDSVSELWTHAQ

VVGERYGSKKSMVILTSSVTAGTAEEFTYIMKRLGRALVIGEVTSGGCQ

PPQTYHVDDTNLYLTIPTARSVGASDGSSWEGVGVTPHVVVPAEEALAR

AKEMLQHNQLRVKRSPGLQDHL.
```

In the embodiments where the tolerogenic antigen is a foreign antigen against which an unwanted immune response can be developed, such as food antigens, specific antigens include, but are not limited to: from peanut: conarachin (Ara h 1), allergen II (Ara h 2), arachis agglutinin, conglutin (Ara h 6); conarachin, for example has the sequence identified as UNIPROT Q6PSU6; from apple: 31 kda major allergen/disease resistance protein homolog (Mal d 2), lipid transfer protein precursor (Mal d 3), major allergen Mal d 1.03D (Mal d 1); from milk: α-lactalbumin (ALA), lactotransferrin; from kiwi: actinidin (Act c 1, Act d 1), phytocystatin, thaumatin-like protein (Act d 2), kiwellin (Act d 5); from egg whites: ovomucoid, ovalbumin, ovotransferrin, and lysozyme; from egg yolks: livetin, apovitillin, and vosvetin; from mustard: 2S albumin (Sin a 1), 11S globulin (Sin a 2), lipid transfer protein (Sin a 3), profilin (Sin a 4); from celery: profilin (Api g 4), high molecular weight glycoprotein (Api g 5); from shrimp: Pen a 1 allergen (Pen a 1), allergen Pen m 2 (Pen m 2), tropomyosin fast isoform; from wheat and/or other cereals: high molecular weight glutenin, low molecular weight glutenin, alpha-, gamma- and omega-gliadin, hordein, secalin and/or avenin; peptides/epitopes useful in the compositions of the disclosure for treating Celiac Disease include some or all of the following sequences, individually in a composition of Formula 1 or together in a cocktail of compositions of Formula 1:

DQ-2 relevant, Alpha-gliadin "33-mer" native: LQLQPFPQPQLPYPQPQLPYPQPQLPYPQPQPF (SEQ ID NO: 54);

DQ-2 relevant, Alpha-gliadin "33-mer" deamidated: LQLQPFPQPELPYPQPELPYPQPELPYPQPQPF (SEQ ID NO: 55);

DQ-8 relevant, Alpha-gliadin: QQYPSGQGSFQPSQQNPQ (SEQ ID NO: 56);

DQ-8 relevant, Omega-gliadin (wheat, U5UA46): QPFPQPEQPFPW (SEQ ID NO: 57);

Alpha-gliadin "15-mer" fragment: ELQPFPQPEL PYPQP (SEQ ID NO: 58);

Gliadin linker: GCRGGGPQPQPFPSQQPY (SEQ ID NO: 59);

Gliadin extended: GCRGGGPQPQPFPSQQPYLQL QPFP QPQ LPYPQPQLPYPQPQLPYPQPQPF (SEQ ID NO: 60);

Gliadin deamidated extended: GCRGGGPQPQPFPSQQPYLQLQPFPQPELPYPQP ELPYPQP ELPYPQPQPF (SEQ ID NO: 61); from strawberry: major strawberry allergy Fra a 1-E (Fra a 1); and from banana: profilin (Mus xp 1).

In the embodiments where the antigen is a foreign antigen against which an unwanted immune response is developed, such as to animal, plant and environmental antigens, specific antigens can, for example, be: cat, mouse, dog, horse, bee, dust, tree and goldenrod, including the following proteins or peptides derived from: weeds, (including ragweed allergens amb a 1, 2, 3, 5, and 6, and Amb t 5; pigweed Che a 2 and 5; and other weed allergens Par j 1, 2, and 3, and Par o 1); grass (including major allergens Cyn d 1, 7, and 12; Dac g 1, 2, and 5; Hol l 1.01203; Lol p 1, 2, 3, 5, and 11; Mer a 1; Pha a 1; Poa p 1 and 5); pollen from ragweed and other weeds (including curly dock, lambs quarters, pigweed, plantain, sheep sorrel, and sagebrush), grass (including Bermuda, Johnson, Kentucky, Orchard, Sweet vernal, and Timothy grass), and trees (including *catalpa*, elm, hickory, olive, pecan, sycamore, and walnut); dust (including major allergens from species *Dermatophagoides pteronyssinus*, such as Der p 1, 2, 3, 4, 5, 6, 7, 8, 9, 10, 11, 14, 15, 18, 20, 21, and 23; from species *Dermatophagoides farina*, such as Der f 1, 2, 3, 6, 7, 10, 11, 13, 14, 15, 16, 18, 22, and 24; from species *Blomia tropicalis* such as Blo t 1, 2, 3, 4, 5, 6, 10, 11, 12, 13, 19, and 21; also allergens Eur m 2 from *Euroglyphus maynei*, Tyr p 13 from *Tyrophagus putrescentiae*, and allergens Bla g 1, 2, and 4; Per a 1, 3, and 7 from cockroach); pets (including cats, dogs, rodents, and farm animals; major cat allergens include Fel d 1 through 8, cat IgA, BLa g 2, and cat albumin; major dog allergens include Can f 1 through 6, and dog albumin); bee stings, including major allergens Api m 1 through 12; and fungus, including allergens derived from, species of *Aspergillus* and *Penicillium*, as well as the species *Alternaria alternata*, *Davidiella tassiana*, and *Trichophyton rubrum*.

In Parkinson's disease, the main antigen is alpha synuclein. Alpha synuclein, including an exogenously obtained form useful in the tolerogenic compositions of the disclosure, has the following sequence (UNIPROT P37840):

(SEQ ID NO: 62)
MDVFMKGLSKAKEGVVAAAEKTKQGVAEAAGKTKEGVLYVGSKTKEGVV

HGVATVAEKTKEQVTNVGGAVVTGVTAVAQKTVEGAGSIAAATGFVKKD

QLGKNEEGAPQEGILEDMPVDPDNEAYEMPSEEGYQDYEPEA.

The antigen can be a complete protein, a portion of a complete protein, a peptide, or the like, and can be derivatized (as discussed above) for attachment to a linker and/or mannosylating moiety, can be a variant and/or can contain conservative substitutions, particularly maintaining sequence identity, and/or can be desilylated.

F. EXAMPLES

The following examples are included to demonstrate non-limiting embodiments of the invention disclosed herein. It should be appreciated by those of skill in the art that the techniques disclosed in the examples which follow represent techniques discovered by the inventor to function well in the practice of the embodiments of the invention. However, those of skill in the art should, in light of the present disclosure, appreciate that many changes can be made in the specific embodiments which are disclosed and still obtain a like or similar result without departing from the spirit and scope of the embodiments of the invention disclosed herein.

Example 1

Polymer and Conjugate Synthesis

All reactions were carried out at room temperature unless specified. Unless otherwise stated, chemicals were reagent grade and purchased from Sigma-Aldrich (Saint Louis, Mo., USA). Size exclusion chromatography was carried out on an ÄKTA protein purification system (General Electric Healthcare Lifesciences), using a Superdex 200 10/300 column (General Electric Healthcare Lifesciences). All NMR spectra were collected on a Bruker Avance-II 400 MHz NMR, unless otherwise noted, and NMR spectra were analyzed with MnovaNMR (Mestrelab). High pressure size exclusion chromatography was performed on a Dionex Ultimate 3000 UHPLC (Thermo Fisher Scientific). Gels were imaged using a Biorad Universal Hood Gel Doc 2000 System (Biorad). Antigens conjugated to polymers as disclosed in the Examples are non-limiting examples of tolerogenic antigens according to embodiments disclosed herein, including embodiments using immunogenic fragments of antigens.

Compound 1: 1-(2-chloroethyl)-α-D-mannose

Acetyl chloride (4.35 mL, 61.05 mmol) was added dropwise to the ice-cold solution of D-mannose (10.0 g, 55.51 mmol) in chloroethanol (40 mL, 413.68 mmol). The mixture was stirred for 15 minutes at 4° C. and then was transferred to the oil bath at 70° C. The reaction was then stirred for 4 h. After cooling to room temperature, a dark brown solution was poured into a 400 mL solution of ethyl acetate and DCM (3:1, v/v) in order to remove excess chloroethanol. The mixture was placed at −20° C. for 30 minutes and then a dark brown sticky precipitate was collected from the supernatant. The precipitate was dissolved in anhydrous ethanol and 3 spoons of activated charcoal was added. The suspension was mixed for 1.5 h and then filtered through Celite and washed with ethanol. In the last step, ethanol was evaporated via rotary evaporation to provide 12.8 g (95.24%) of product: $C_8H_{15}ClO_6$, ESI-MS $[M+Na]^+_{theor}$=m/z 265.0455, $[M+Na]^+_{found}$=m/z 265.0458; $^1H$ NMR (400 MHz, $D_2O$) δ 4.86 (s, C1, 1H), 3.92 (dd, C2, 1H), 3.62-3.85 (multiple signals from 7H: C3, C4, C5, C6, C6', ethoxy group); $^{13}C$ NMR (100 MHz, $D_2O$) δ 99.84, 76.32, 72.94, 70.52, 69.94, 69.65, 67.76, 66.75, 60.96, 43.39.

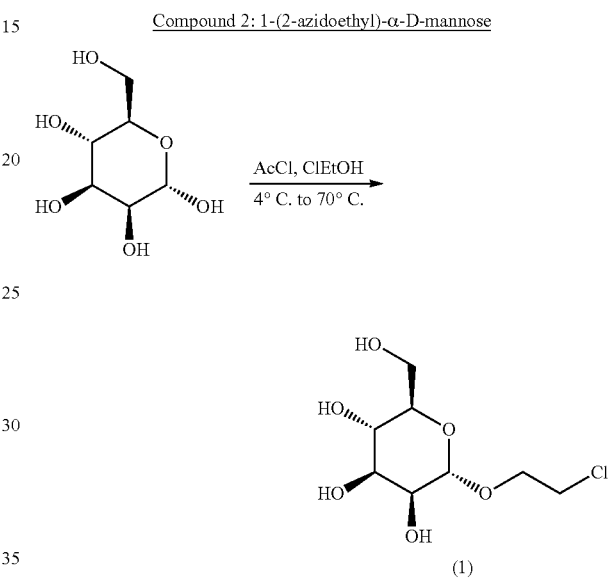

Compound 2: 1-(2-azidoethyl)-α-D-mannose

Compound 1 (12.7 g, 52.48 mmol) was dissolved in 15 mL of N,N-dimethylformamide. To that solution, sodium azide was added (5.0 g, 76.92 mmol) and the suspension was placed in an oil bath and stirred over night at 90° C. After 16 h, the reaction mixture was filtered through Celite and the solvent was then removed via rotary evaporation to provide a oily, brown substance. The residual was adsorbed on silica gel and purified using flash chromatography (DCM:MeOH 92:8, v/v) to yield 5.6 g (42.86%) of pure product: $C_8H_{15}N_3O_6$, ESI-MS $[M+Na]^+_{theor}$=m/z 272.2578, $[M+Na]^+_{found}$=m/z 272.0850; $^1H$ NMR (400 MHz, $D_2O$) δ 4.84 (s, C1, 1H), 3.91 (dd, C2, 1H), 3.39-3.87 (multiple signals from 7H: C3, C4, C5, C6, C6', ethoxy group); $^{13}C$ NMR (100 MHz, $D_2O$) δ 99.85, 72.94, 70.44, 69.98, 66.73, 66.34, 50.24.

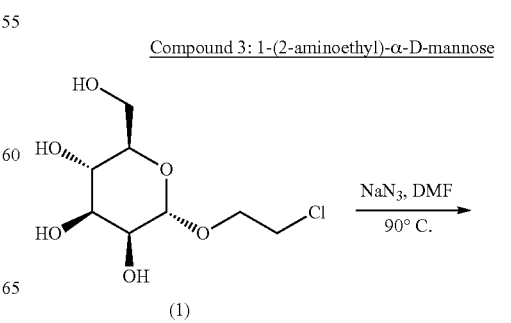

Compound 3: 1-(2-aminoethyl)-α-D-mannose

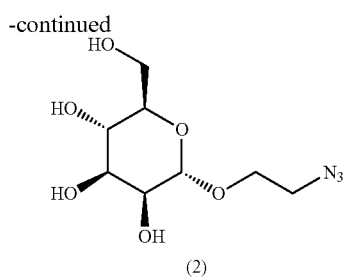

(2)

A suspension of 2 (5.5 g, 22.09 mmol) and 10% palladium on carbon (one spoon, ca. 500 mg) in 10 mL of ethanol was hydrogenated in a Shlenk flask with an initial pressure of 2 bars of hydrogen gas. The reduction process was monitored by TLC. After 3 h reaction was completed and the suspension was filtered through Celite. The solvent was evaporated in vacuo to give 4.9 g (99.48%) of product: C8H17NO6, ESI-MS [M+Na]+theor=m/z 246.0954, [M+Na]+found=m/z 246.0955; 1H NMR (400 MHz, D2O) δ 4.80 (s, C1, 1H), 3.89 (dd, C2, 1H), 3.83-3.44 (multiple signals from 7H: C3, C4, C5, C6, C6', ethoxy group); 13C NMR (100 MHz, D2O) δ 99.87, 72.74, 70.55, 70.03, 68.82, 66.81, 60.97, 39.94.

Compound 4: N-[2-(α-D-mannose)ethyl] methacylamide

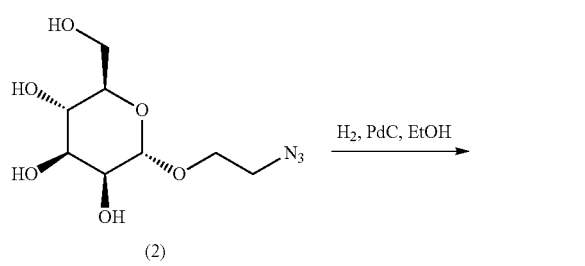

Compound 3 (4.5 g, 20.17 mmol) was dissolved in 10 mL of N,N-dimethylformamide. To that solution, triethylamine (3 mL, 22.28 mmol) was added and the mixture was cooled down to 4° C. Subsequently, pentafluorophenyl methacrylate (4.38 mL, 24.21 mmol) was added drop-wise with constant stirring. After 30 minutes, ice-bath was removed and the reaction was allowed to stir at room temperature for the next 4 h. Next, the solvent was evaporated and the residual was adsorbed on silica gel. The purification of crude material using flash chromatography (DCM:MeOH 95:5, v/v) provided 3.8 g (64.73%) of mannose monomer: C12H21NO7, ESI-MS [M+Na]+theor=m/z 314.1216, [M+Na]+found=m/z 314.1208; 1H NMR (400 MHz, D2O) δ 5.6 (s, 1H), 5.38 (s, 1H), 4.78 (s, 1H), 3.84 (s, C2, 1H), 3.77-3.34 (multiple signals from 7H: C3, C4, C5, C6, C6', ethoxy group), 1.85 (s, 3H); 13C NMR (100 MHz, D2O) δ 172.06, 139.06, 121.00, 99.63, 72.78, 70.47, 69.99, 66.58, 65.73, 60.78, 39.04, 17.68.

Compound 17: 2-(2-(2-(2-hydroxyethoxy)ethoxy)ethoxy)ethyl 4-methylbenzenesulfonate

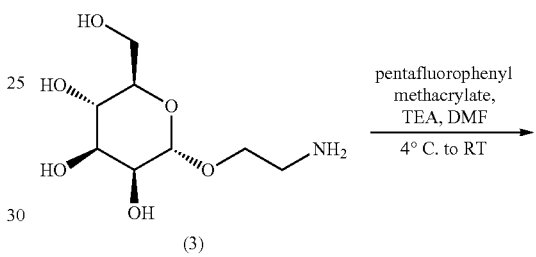

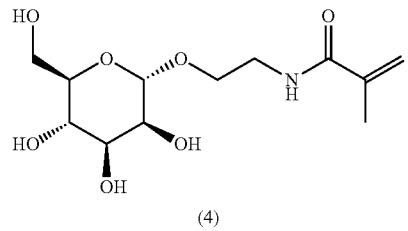

(4)

Tetraethylene glycol (2.5 g, 12.9 mmol) and pyridine (1.0 g, 12.6 mmol) were added to 50 mL of DCM and stirred for 20 minutes at 0° C. To that solution, p-toluenesulfonyl chloride (2.37 g, 10 mmol) in 15 mL of DCM was added slowly. The reaction mixture was then stirred for 2 h at 0° C. followed by 4 h at room temperature. After that time, the solvent was evaporated and crude product was purified via flash chromatography (ethyl acetate:hexane 6:4, v/v). The final yield was 1.95 g (72.22%): C15H24O7S, ESI-MS [M+H]+theor=m/z 349.1321, [M+H]+found=m/z 349.1325; 1H NMR (400 MHz, CDCl3) δ 7.68 (d, 2H), 7.24 (d, 2H), 4.00-4.12 (m, 2H), 3.42-3.70 (m, 14H), 2.89 (t, 1H), 2.33 (s, 3H); 13C NMR (100 MHz, DMSO-d6) δ 144.68, 132.76, 129.68, 127.73, 72.34, 70.46, 70.41, 70.22, 70.10, 69.17, 68.44, 61.40, 21.41.

Compound 18: 2-(2-(2-(2-azidoethoxy)ethoxy)ethoxy)ethan-1-ol

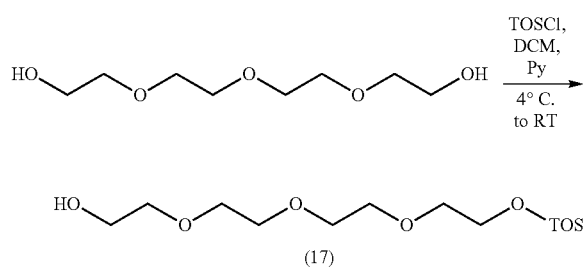

Sodium azide (1.5 g, 23.1 mmol) was added to a solution of 17 (1.5 g, 4.3 mmol) in N,N-dimethylformamide (75 mL) at room temperature. The reaction mixture was stirred overnight at 90° C. The reaction was then filtered and the solvent was removed in vacuo. The resulting viscous liquid was then purified by flash column chromatography (ethyl acetate:hexane 6:4, v/v) to yield a pure product (1.25 g, 83%): C8H17N3O4, ESI-MS [M+Na]+theor=m/z 242.1117, [M+Na]+found=m/z 242.1171; 1H NMR (400 MHz, DMSO-d6) δ 3.49-3.65 (m, 14H), 3.30 (t, 2H), 2.91 (t, 1H); 13C NMR (100 MHz, DMSO-d6) δ 72.43, 70.56, 70.52, 70.46, 70.21, 69.91, 61.51, 50.54.

Compound 19: 2-(2-(2-(2-azidoethoxy)ethoxy)ethoxy)ethyl 4-cyano-4(((dodecylthio)carbonthioyl) thio)pentanoate

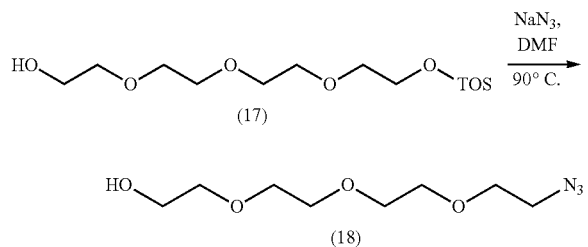

4-Cyano-4-[(dodecylsulfanylthiocarbonyl)sulfanyl]pentanoic acid (500 mg, 1.24 mmol), compound 18 (226 mg, 1.03 mmol) and DCC (255 mg, 1.24 mmol) were dissolved in 4 mL of DCM. The solution was placed in an ice bath and let stir for 30 minutes. After that time, 4-dimethylaminopyridine (12.6 mg, 0.10 mmol) dissolved in 1 mL of DCM was added drop-wise. The solution was stirred at 0° C. for 2 h and then at room temperature for 1 hour. Once reaction was completed, DCM was evaporated in vacuum. The crude product was purified via column chromatography (DCM:ethyl acetate 97:3, v/v) to yield 300 mg (88.57%) of the pure product: C27H48N4O5S3, ESI-MS [M+H]+theor=m/z 604.2865 [M+H]+found=m/z 604.2862; 1H NMR (400 MHz, CDCl3) δ 4.26 (t, 2H), 3.76-3.65 (m, 12H), 3.39 (t, 2H), 3.33 (t, 2H), 2.66 (dd, 2H), 2.53 (m, 1H), 2.38 (m, 1H), 1.88 (s, 3H), 1.69 (dt, 2H), 1.38 (m, 2H), 1.26 (s, 16H), 0.88 (t, 3H); 13C NMR (100 MHz, CDCl3) δ 216.92, 171.46, 119.00, 70.72, 70.68, 70.61, 70.07, 68.96, 64.16, 50.69, 46.35, 37.06, 33.81, 31.91, 29.71, 29.62, 29.54, 29.42, 29.34, 29.07, 28.93, 27.68, 24.84, 22.69, 14.13.

Compound 21: p (Man)

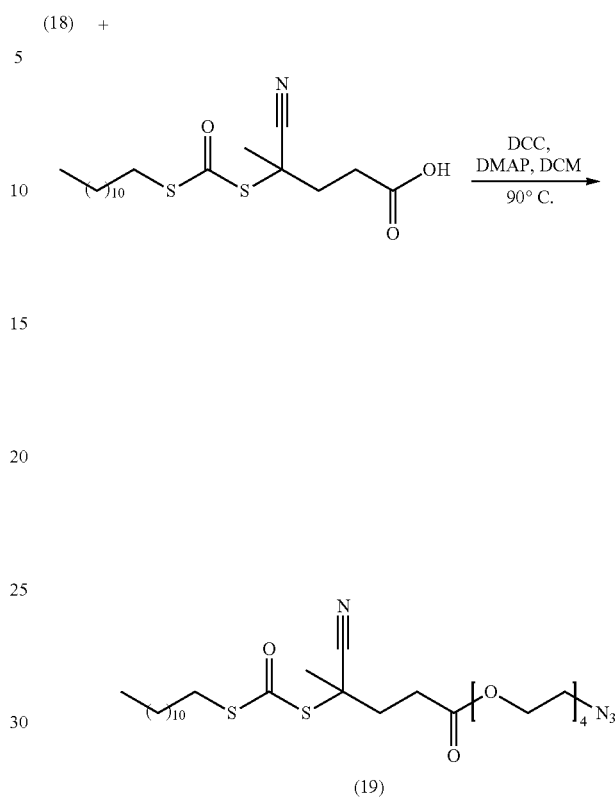

The mannose monomer (4) (150.0 mg, 0.51 mmol) and (20) (130.0 mg, 1.03 mmol) were dissolved in 600 μl of anhydrous DMF and added to a schlenk tube. Then, RAFT agent (19) (18.5 mg, 0.03 mmol) in 100 μl of DMF and AIBN (1 mg, 0.006 mmol) in 10 μl of DMF were added to the schlenk tube. The tube was degassed via four freeze-pump-thaw cycles and then immersed in an oil bath preheated at 70° C. to initiate polymerization. The reaction was left stirring for 14 hours. After that time, the polymer was precipitated by transferring its viscous solution into 20 mL of cold acetone. The light-yellow suspension was placed in the freezer for 30 minutes. The precipitate was then centrifuged and re-suspended in fresh acetone. The processed was repeated 3 times. In the final step, the resultant glycopolymer (150 mg, 47.6%) was dried in a vacuum oven at reduced pressure and characterized by means of 1H NMR and GPC. The p(HPMA-TLR7) used in the biological studies had a number average molecular weight of 15,425 Da, as determined by size exclusion chromatography, using a dextran standard, a degree of polymerization of 82.1, and were composed of a 1:2.25 molar ratio of Mannose:HPMA, as determined by 1H NMR.

Compound 25: Ethanol disulfanyl polyethylene glycol amine

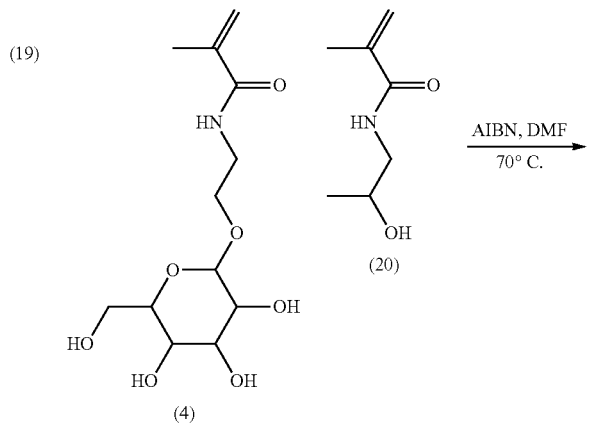

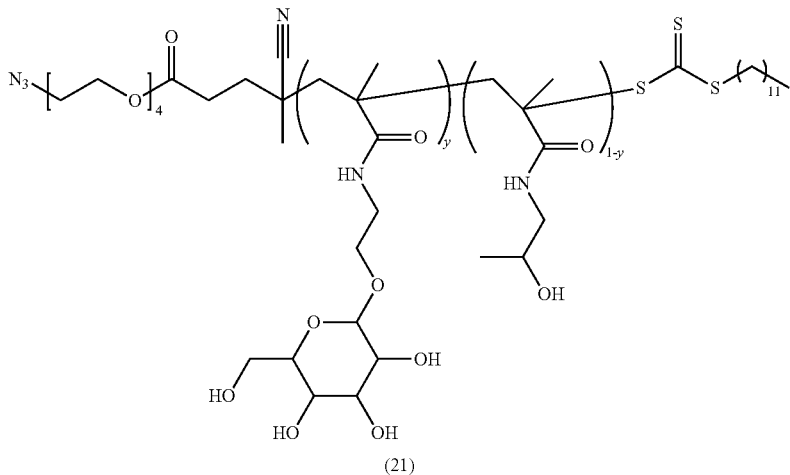

A solution of thiol polyethylene glycol amine (JenKem Technology, USA) (1.0 g, 0.5 mmol) in DCM (5 ml) was added dropwise to a stirred solution of 2-(2-pyridinyldithio) ethanol (24) (467.5 mg, 2.5 mmol) in MeOH (3 ml). The solution was stirred at room temperature for 10 h then approximately half the solvent was removed via rotary evaporation. The remaining crude product was then decanted into ice cold hexanes (40 ml) and placed at −20° C. for 4 h. The precipitate and solvent mixture was centrifuged at 2000 g for 3 min. The solvent was then decanted and excess solvent was removed from the pelleted precipitate under reduced pressure. The crude product was then used in the next step without further purification (65% crude yield). The final structure was characterized by 1H NMR and reverse phase chromatography.

Compound 26: Ethanol disulfanyl polyethylene glycol (1R,8S,9s)-Bicyclo[6.1.0]non-4-yn-9-ylmethyl carbamate

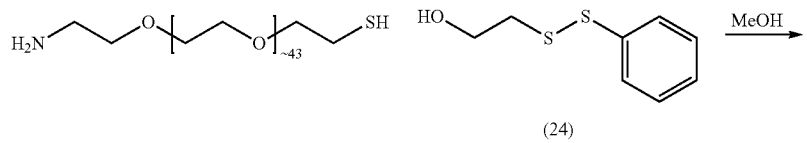

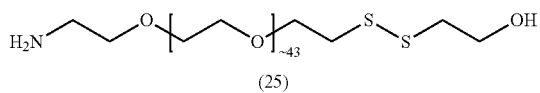

A solution of (1R,8S,9s)-Bicyclo[6.1.0]non-4-yn-9-ylmethyl N-succinimidyl carbonate (90 mg, 0.30 mmol) in DCM (0.5 ml) was added dropwise to an ice-cooled stirred solution of ethanol disulfanyl polyethylene glycol amine 25 (0.5 g, 0.24 mmol) and trimethylamine (48 mg, 0.48 mmol) in DCM (5 ml). After the addition of (1R,8S,9s)-Bicyclo[6.1.0]non-4-yn-9-ylmethyl N-succinimidyl carbonate, the reaction was allowed to come to room temperature and stirred for another 6 h. The reaction mixture was then poured into ice-cold hexanes (40 ml) and placed at −20° C. for 4 h. The precipitate and solvent mixture was centrifuged at 2000 g for 3 min. The solvent was then decanted and excess solvent was removed from the pelleted precipitate under reduced pressure. The crude product was then used in the next step without further purification (75% crude yield). The final structure was characterized by 1H NMR and reverse phase chromatography.

Compound 27: N-succinimidyl carboamate Ethanol disulfanyl polyethylene glycol (1R,8S,9s)-Bicyclo[6.1.0]non-4-yn-9-ylmethyl carbamate (Self-immolative Linker)

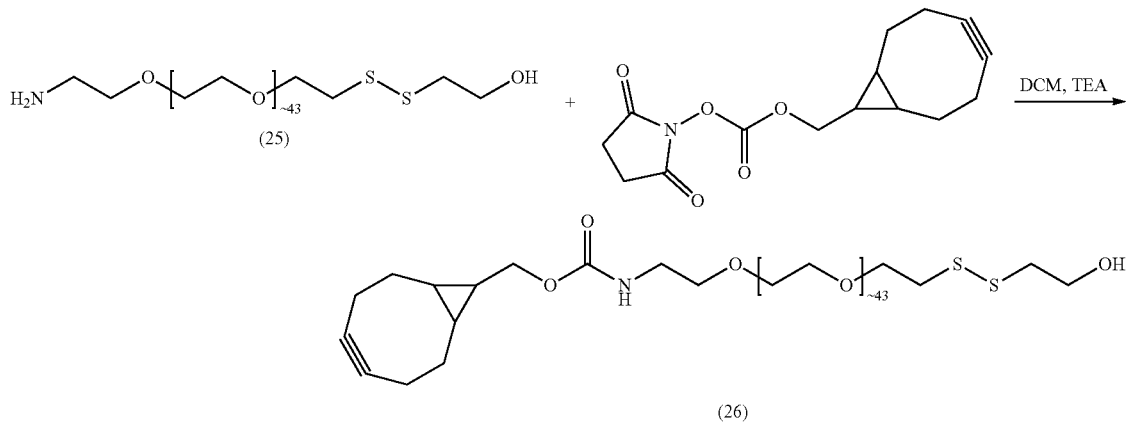

A solution of Ethanol disulfanyl polyethylene glycol (1R,8S,9s)-Bicyclo[6.1.0]non-4-yn-9-ylmethyl carbamate (300 mg, 0.13 mmol) in anhydrous acetonitrile (ACN) (1.5 ml) was added dropwise to a stirred solution of N,N'-Disuccinimidyl carbonate 26 (0.5 g, 0.24 mmol) and trimethylamine (48 mg, 0.48 mmol) in anhydrous ACN (5 ml). The reaction mixture was stirred overnight and was then poured into ice-cold hexanes (40 ml) and placed at −20° C. for 4 h. The precipitate and solvent mixture was centrifuged at 2000 g for 3 min. The solvent was then decanted and excess solvent was removed from the pelleted precipitate under reduced pressure. The crude product was purified via silica gel flash chromatography trough a thin pad of silica DCM:MeOH (85:15) (yield: 43%, 129 mg). The final structure was characterized by 1H NMR and reverse phase chromatography.

Compound 28: General procedure for OVA-, asparaginase-self-immolative linker conjugates

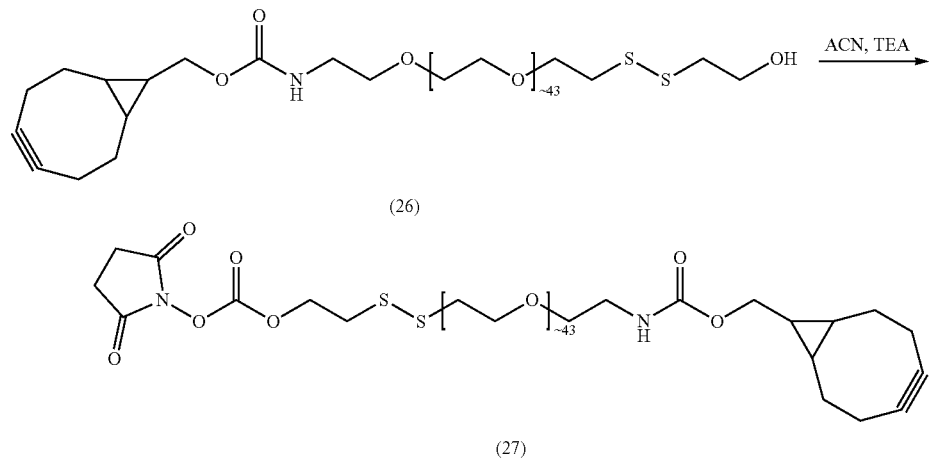

EndoGrade® Ovalbumin (OVA) (Hyglos) (10 mg, 222.2 nmol), recombinant asparaginase (7.2 mg, 222.2 nmol) and self-immolative Linker (27) (5 mg) were added to an endotoxin free tube. Phosphate buffer at pH 7.7 (200 µL) was added to the tube and the tube was stirred at 1 h at room temperature. The reaction mixture was then filtered (0.22 µM) and the conjugates were purified via Zeba Spin Desalting Columns with a 30 kDa cutoff limit (Thermo Fisher). Chemical conjugation was verified via gel electrophoresis and high pressure size exclusion chromatography.

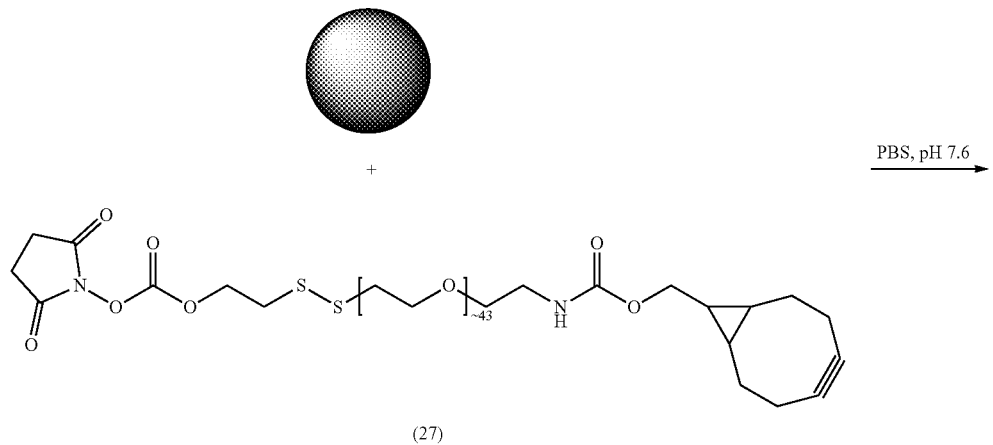

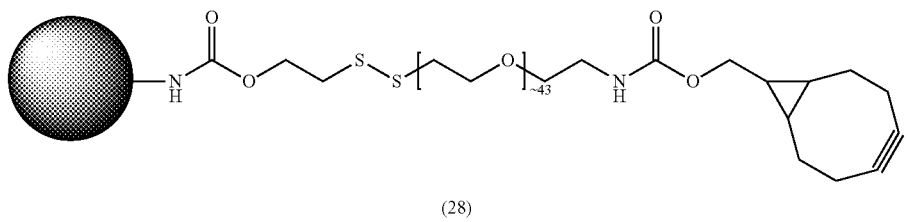

Compound 28 in PBS, prepared as described above, was added to an endotoxin free tube and p(Man) (21) (30 mg) was added and the reaction was stirred for 30 min at room temperature. The reaction mixture was then filtered (0.22 µM) and the final product was purified via size exclusion chromatography. Chemical conjugation was verified via gel electrophoresis and high pressure size exclusion chromatography.

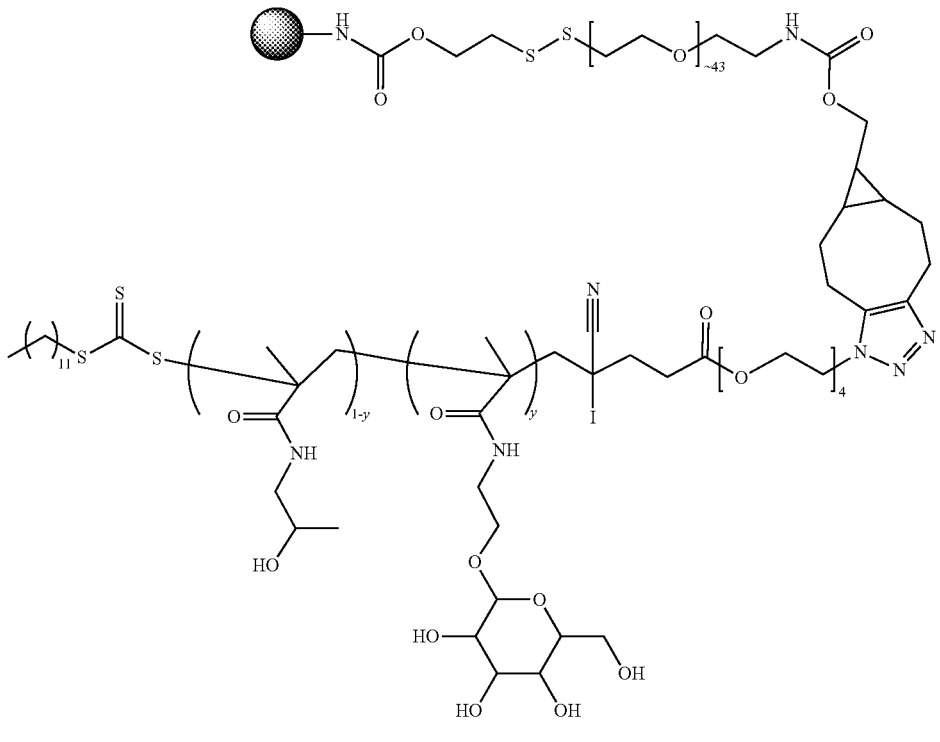

Example 2

OTI/OTII Challenge to Tolerance Model

BLK6 mice were treated with saline, or 10 μg of OVA (as a non-limiting example of an immunogenic antigen) in the form of free OVA or OVA conjugated to p(Man) (OVA-p(Man)) one day and 7 days after an adoptive transfer of $7.0 \times 10^5$ OTI and OTII T cells. These mice were challenged with an intradermal injection of LPS and OVA 14 days after the initial OTI and OTII T cell transfer and then the immune response in the draining lymph nodes (dLNs) was assessed on day 19 and compared to mice that were treated with saline, but did not receive the challenge of LPS and OVA (No-challenge).

Profound tolerance was induced in the CD4+ T cell compartment, as shown in FIGS. 1-2. In terms of total cell frequencies, both dosing regimens of both OVA-p(Man) resulted in equivalent low levels of OTII cells after challenge, statistically lower than by treatment of OVA (* indicates p<0.05, ** indicates p<0.01), as shown in FIG. 1. When the cells that remained were analyzed by flow cytometry for the presence of the transcription factor FoxP3 and the receptor CD25, the numbers of FoxP3+CD25+ cells (markers of T regulatory cells) was statistically significantly elevated compared to treatment with OVA alone, as shown in FIG. 1. Additionally, the spleens of animals treated with OVA-p(Man) contained a lower percentage of T follicular helper cells (Tfh) as compared to other groups that were challenged with LPS and OVA. When the cells that remained were analyzed by flow cytometry for the expression of IFN-γ after exposure to OVA antigen, the frequency of CD4+ T cells expressing this inflammatory cytokine was decreased in the groups receiving OVA-p(Man), as shown in FIG. 2.

Profound tolerance was also induced in the CD8+ T cell compartment, as shown in FIG. 1. In terms of total cell frequencies, OVA-p(Man) resulted in equivalent low levels of OTI cells after challenge, statistically lower than by treatment of OVA (* indicates p<0.05, ** and indicates p<0.01), as shown in FIG. 1. When the cells that remained were analyzed by flow cytometry for the expression of IFN-γ after exposure to SIINFEKLE antigen, the frequency of CD8+ T cells expressing this inflammatory cytokine was decreased in the groups receiving OVA-p(Man), as shown in FIG. 2.

Example 3

Tolerance Induction to Intravenously Administered Asparaginase

Five BALB/c mice per group were injected with 2.5 μg of asparaginase (as a non-limiting example of an immunogenic antigen) formulated as free asparaginase (ASNase) or conjugated to p(Man) (ASNase-p(Man)) once a week for 3 weeks and then, at week 4, were switched to 15 μg of ASNase i.v. once a week for 8 weeks. During the initial 3 weeks ASNase-p(Man) was administered via either i.v. or subcutaneous injection. Sera was taken from the mice and monitored weekly for the presence of αASNase.

Upon intravenous injection of ASNase at week 4, animals treated with saline and subcutaneously administered ASNase-p(Man) experienced a rapid increase in serum αASNase IgG (FIG. 3), animals treated with i.v. administered ASNase-p(Man) did not incur an increase in serum αASNase IgG for the duration of the experiment. Furthermore, after 38 days of treatment, animals treated with ASNase-p(Man) via intravenous infusion, experienced significantly lower αASNase IgG subclass titers (FIG. 3).

At week 22 (3 weeks of tolerization, 8 weeks of ASNase treatment, and 11 weeks after last dose of Asnase), animals treated with saline and ASNase-p(Man) via intravenous infusion were sacrificed and the spleens, livers, and bone marrow of these animals was collected and processed into single cell suspensions. The cells from these organs were stimulated in vitro with recombinant ASNase lacking activity for 3 days. After three days the cells were analyzed via flow cytometry for the existence of αASNase producing cells (plasma cells) and IL-10 producing B regulatory cells. The results show that the bone marrow of animals treated with ASNase-p(Man) had a fewer αASNase plasma cells than animals that were treated with ASNase (FIG. 4). On the contrary, the spleens of animals treated with ASNase-p(Man) had a greater percentage of IL-10 producing B regulatory cells.

Example 4

Effect on Anti-Asparaginase (Anti-ASNase) Humoral Immune Response

To assess the ability of p(Man)-protein conjugates to prevent an anti-asparaginase (anti-ASNase) humoral immune response and thus avoid the loss of efficacy that is the result of rapid antibody-mediated clearance of biological therapeutics form the serum, mice were treated on days −21, −14, and −7 with saline or 2.5 µg of ASNase conjugated to p(Man) (p(Man)-ASNase) via iv infusion (n=5 animals per group). After 7 days, the mice were then treated with weekly iv infusions of 15 µg of wt ASNase for 4 weeks. The mice were then treated with 15 µg of wt ASNase on day 49. On day 70, mice that had been treated with saline on days −21, −14, −7, 0, 14, 21, and 49 were treated with 15 µg of wt ASNase to assess the efficacy of ASNase in naïve mice (FIG. 6). On day 70, the mice that had received saline or p(Man)-ASNase then treated with wt ASNase were also administered 15 µg of wt ASNase. The serum asparagine concentration of each animal was assessed on days 71, 73, and 76.

The results show that one day after being treated with ASNase, animals in each group have a similar serum concentration of asparagine. However, three days after being administered asparagine on day 7, animals treated with only saline or p(Man)-ASNase have a significantly lower serum asparagine concentration as compared to animals that had been treated with saline and then administered wt ASNase on days 0, 7, 14, 21, and 49 (FIG. 7A). In addition, animals treated with p(Man)-ASNase had significantly lower asparagine serum concentrations on day 76 than the animals in other groups. When serum asparagine concentration is plotted against the anti-ASNase titer for each animal in the study, a strong correlation (r=0.8) between serum asparagine concentration and anti-ASNase titer becomes evident (FIG. 7B). These results demonstrate that p(Man)-ASNase inhibits the loss of efficacy associated with an anti-ASNase immune response.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A compound of Formula 1:

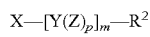   Formula 1 where:
- X comprises an antigen, a tolerogenic portion thereof, or a mimetic thereof;
- Y comprises a linker moiety;
- Z comprises a moiety that specifically targets a mannose receptor;
- p is an integer from 2 to 250;
- m is an integer from 1 to 100;
- $R^2$ is any of functional groups I-III:

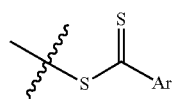  I

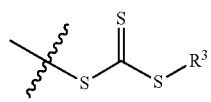  II

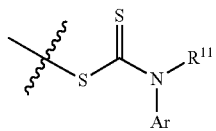  III where Ar is a substituted or unsubstituted aromatic group and one or more of:
- $R^3$ is $C_{1-6}$-alkyl; or
- $R^{11}$ is $C_{1-6}$-alkyl.

2. The compound of claim 1, wherein the moiety that specifically targets a mannose receptor is selected from the group consisting of α-linked mannose, β-linked mannose, substituted mannose, mannose-6-phosphate, N-acetyl mannosamine, and mannan having β(1-4), α(1-6), α(1-2), and/or α(1-3) linkages.

3. The compound of claim 1, wherein Y is a linker resulting from reaction of at least one of a N-hydroxysuccinamidyl linker, maleimide linker, PEG linker, vinylsulfone linker, pyridyl di-thiol-poly (ethylene glycol) linker, pyridyl di-thiol linker, n-nitrophenyl carbonate linker, NHS-ester linker, and nitrophenoxy poly (ethylene glycol) ester linker.

4. The compound of claim 3, wherein Y is covalently bound to X.

5. The compound of claim 1, wherein —[Y(Z)$_p$]— is represented by one of Formula Ya to Yr:

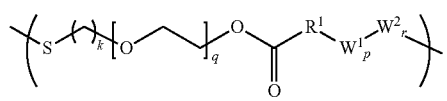  Ya

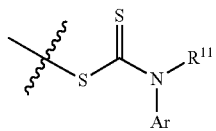  Yb

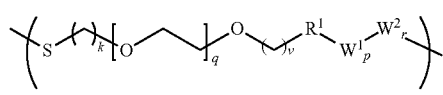  Yc

Yd

Ye

Yf

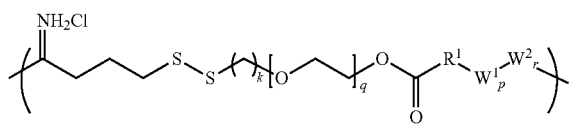  Yg

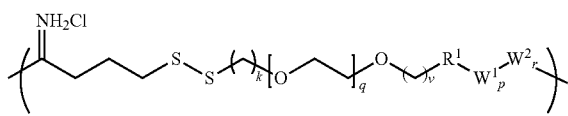  Yh

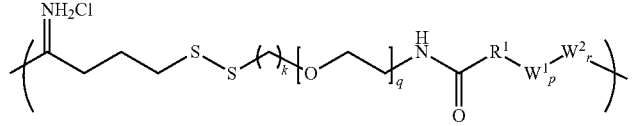  Yi

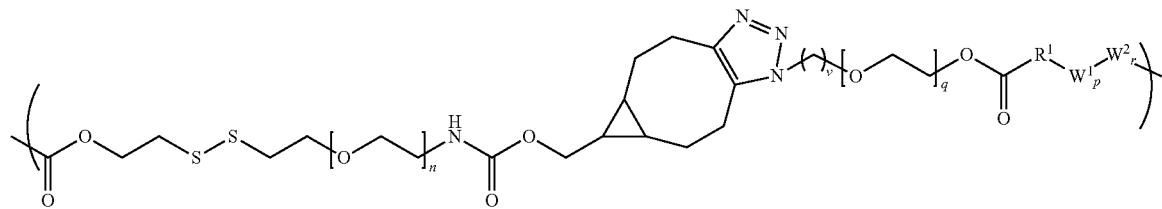
Yj
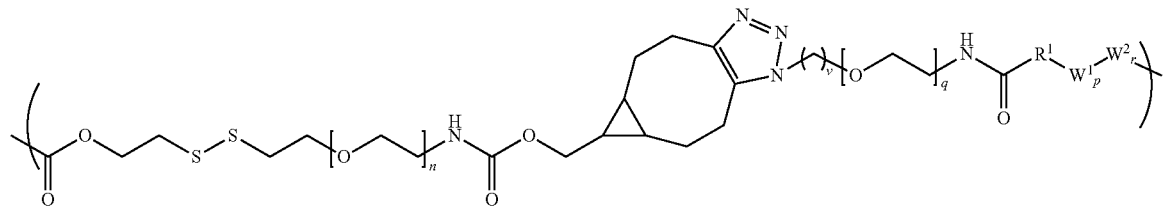
Yk
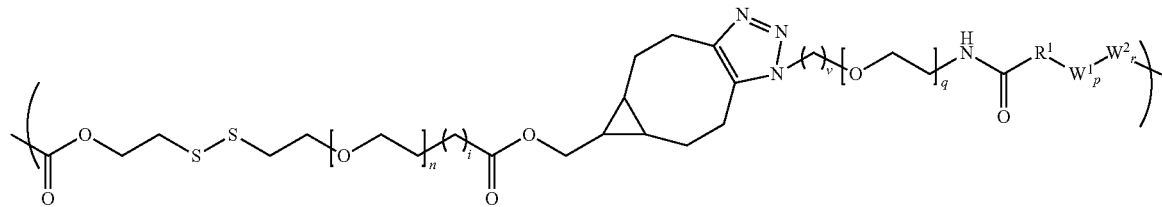
Yl
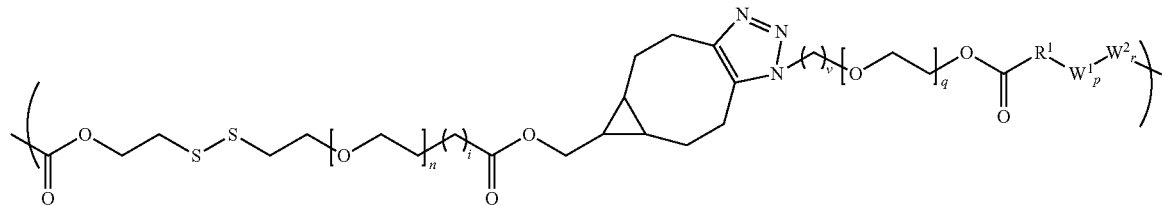
Ym
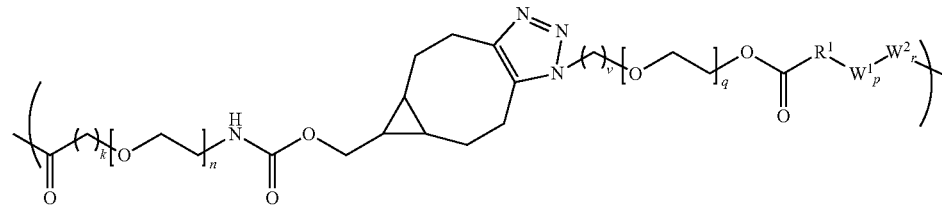
Yn
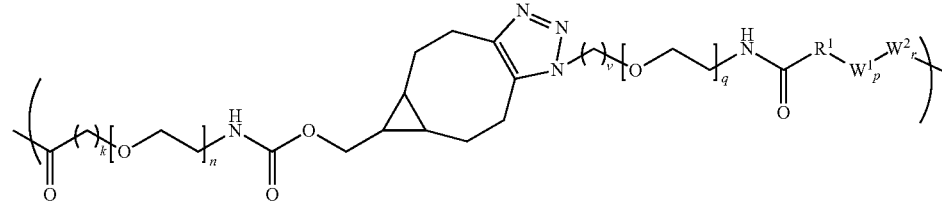
Yo
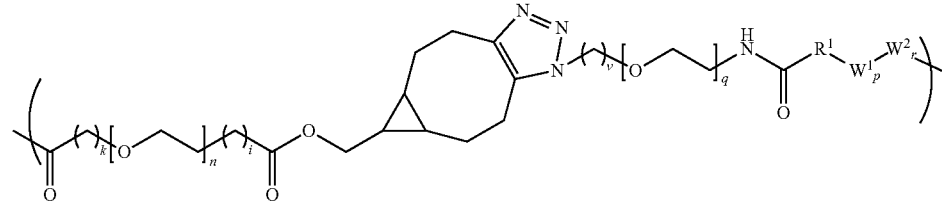
Yp -continued

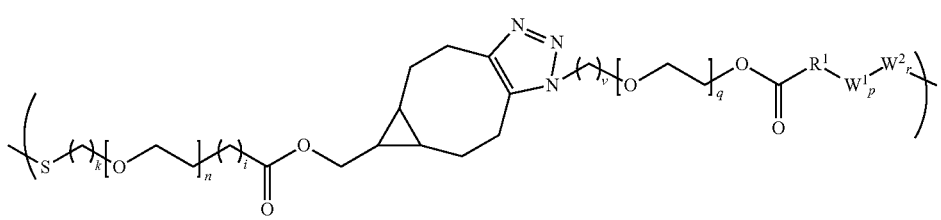
Yq

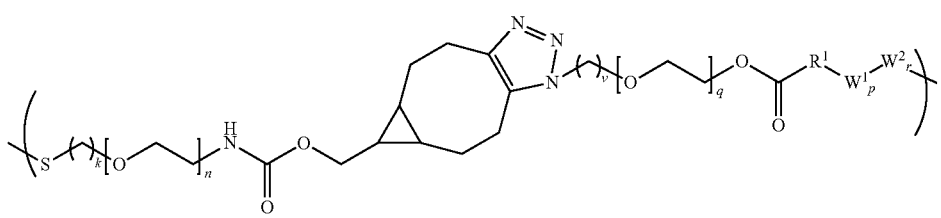
Yr where
n is an integer from 1 to 100;
q is an integer from 1 to 44;
k is an integer from 1 to 12;
i is an integer from 0 to 20;
v is an integer from 1 to 4;
p is an integer from 2 to 250;
r is an integer from 0 to 250;
$R_1$ is —$CH_2$—, —$(CH_2)_2$—$C(CH_3)(CN)$—, —$(CH_2)_2$—$C(CH_3)(CH_3)$—, —$(CH_2)_2$—$CH(CH_3)$— or —$CH(CH_3)$—;
$W^1$ and $W^2$ are as defined below:

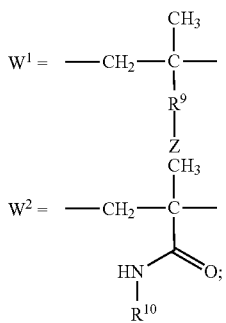

$R^9$ is a direct bond, —(CH2)2-NH—C(O)— (an ethylaceetamido group or "EtAcN") or —(CH2)2-(O—CH2-CH2)t-NH—C(O)— (a pegylated ethylacetamido group or "Et-PEGt-AcN")
t is an integer from 1 to 5;
Z is mannose or a mannose receptor-targeting moiety; and
$R^{10}$ is an aliphatic group, an alcohol, an aliphatic amine-containing group, or an aliphatic alcohol.

6. The compound of claim 1, wherein Y is an antibody, antibody fragment, peptide or other ligand that binds to X.

7. The compound of claim 1, wherein X is an antigen against which a patient may develop or has developed an unwanted immune response.

8. The compound of claim 7, wherein the antigen is a foreign transplant antigen, an alloantigen, an autoimmune antigen, a food antigen, an animal antigen, a plant antigen, an environmental antigen, a therapeutic antigen, a synthetic self-antigen, or a tolerogenic portion thereof.

9. The compound of claim 8, wherein X is an asparaginase antigen or an ovalbumin antigen.

10. The compound of claim 1, wherein the mannose receptor is mannose-6-phosphate receptor.

11. The compound of claim 1, wherein Y and X are connected through a bond configured to cleave when the compound reaches a target area.

12. The compound of claim 1, wherein Ar is selected from:

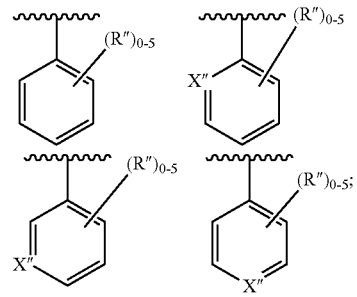

where each instance of R", where present, is independently selected from an optionally substituted $C_{1-6}$-alkyl, optionally substituted $C_{1-6}$ alkoxy, optionally substituted amino, OH, or halogen and wherein, X" is a heteroatom.

13. The compound of claim 12 wherein X" is N.

14. The compound of claim 1, wherein $R^{11}$ is —$CH_3$.

15. A composition comprising the compound of claim 1.

16. A method of inducing immunological tolerance to an antigen target comprising administering to a subject a composition Formula 1:

$$X—[Y(Z)_p]_m—R^2 \quad \text{Formula 1}$$

where:
X comprises an antigen, a tolerogenic portion thereof, or a mimetic thereof;
Y comprises a linker moiety;
Z comprises a moiety that specifically targets a mannose receptor;
p is an integer from 2 to 250;
m is an integer from 1 to 100;

$R^2$ is any of functional groups I-III:

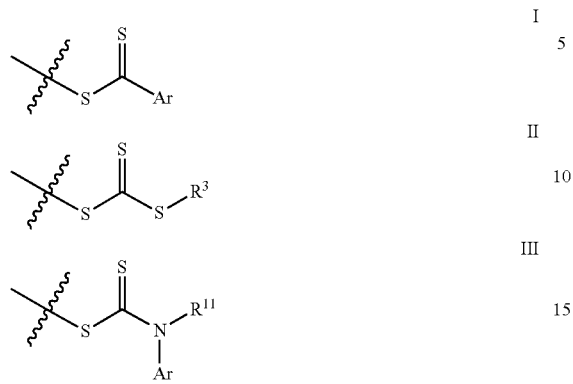

I

II

III where Ar is a substituted or unsubstituted aromatic group and one or more of:
$R^3$ is $C_{1-6}$-alkyl; or
$R^{11}$ is $C_{1-6}$-alkyl.

17. The method of claim 16, wherein the moiety that specifically targets a mannose receptor is selected from the group consisting of α-linked mannose, β-linked mannose, substituted mannose, mannose-6-phosphate, N-acetyl mannosamine, and mannan having β(1-4), α(1-6), α(1-2), and/or α(1-3) linkages.

* * * * *

SEQUENCE LISTING

```
<160> NUMBER OF SEQ ID NOS: 62

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 585
<212> TYPE: PRT
```

<213> ORGANISM: Homo sapiens

<400> SEQUENCE: 2

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
    355                 360                 365

Gly Gly Leu Leu Met Ser Arg Lys His Lys Trp Lys Leu Ser Gly Val
370                 375                 380

Glu Arg Ala Asn Ser Val Thr Trp Asn Pro His Lys Met Met Gly Val
385                 390                 395                 400
```

```
Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 3
<211> LENGTH: 355
<212> TYPE: PRT
<213> ORGANISM: Homo sapiens

<400> SEQUENCE: 3

Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
            20                  25                  30

Gly Asp Pro Arg Asn Ile Phe Phe Ile Tyr Phe Pro Leu Cys Phe Gln
        35                  40                  45

Phe Asn Gln Thr Val Gly Thr Lys Met Ile Trp Val Ala Val Ile Gly
    50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
        115                 120                 125

Ala Ala Leu Ser His Thr Val Cys Gly Met Asp Lys Phe Ser Ile Thr
    130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190
```

```
Phe Glu His Thr Pro Gly Ile Gln Thr Ala Ser Leu Gly Thr Tyr Leu
        195                 200                 205

Lys Thr Asn Leu Phe Leu Phe Leu Phe Ala Val Gly Phe Tyr Leu Leu
210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
                260                 265                 270

Ile Asn Ser Glu Met Phe Leu Ser Cys Arg Gly Gly Asn Asn Tyr
                275                 280                 285

Thr Leu Ser Phe Arg Leu Leu Cys Ala Leu Thr Ser Leu Thr Ile Leu
            290                 295                 300

Gln Leu Tyr His Phe Leu Gln Ile Pro Thr His Glu Glu His Leu Phe
305                 310                 315                 320

Tyr Val Leu Ser Phe Cys Lys Ser Ala Ser Ile Pro Leu Thr Val Val
                325                 330                 335

Ala Phe Ile Pro Tyr Ser Val His Met Leu Met Lys Gly Ser Gly Lys
                340                 345                 350

Lys Ser Gln
        355

<210> SEQ ID NO 4
<211> LENGTH: 86
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 5
<211> LENGTH: 70
<212> TYPE: PRT
<213> ORGANISM: Homo sapiens

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60
```

-continued

```
Arg Gly Ile Val Glu Gln
65                  70

<210> SEQ ID NO 6
<211> LENGTH: 62
<212> TYPE: PRT
<213> ORGANISM: Homo sapiens

<400> SEQUENCE: 6

Ser His Leu Val Glu Ala Leu Tyr Leu Val Cys Gly Glu Arg Gly Phe
1               5                   10                  15

Phe Tyr Thr Pro Lys Thr Arg Arg Glu Ala Glu Asp Leu Gln Val Gly
            20                  25                  30

Gln Val Glu Leu Gly Gly Gly Pro Gly Ala Gly Ser Leu Gln Pro Leu
        35                  40                  45

Ala Leu Glu Gly Ser Leu Gln Lys Arg Gly Ile Val Glu Gln
    50                  55                  60

<210> SEQ ID NO 7
<211> LENGTH: 30
<212> TYPE: PRT
<213> ORGANISM: Homo sapiens

<400> SEQUENCE: 7

Ser His Leu Val Glu Ala Leu Tyr Leu Val Cys Gly Glu Arg Gly Phe
1               5                   10                  15

Phe Tyr Thr Pro Lys Thr Arg Arg Glu Ala Glu Asp Leu Gln
            20                  25                  30

<210> SEQ ID NO 8
<211> LENGTH: 38
<212> TYPE: PRT
<213> ORGANISM: Homo sapiens

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln
        35

<210> SEQ ID NO 9
<211> LENGTH: 15
<212> TYPE: PRT
<213> ORGANISM: Homo sapiens

<400> SEQUENCE: 9

Ser His Leu Val Glu Ala Leu Tyr Leu Val Cys Gly Glu Arg Gly
1               5                   10                  15

<210> SEQ ID NO 10
<211> LENGTH: 27
<212> TYPE: PRT
<213> ORGANISM: Homo sapiens

<400> SEQUENCE: 10

Gly Gly Gly Pro Gly Ala Gly Ser Leu Gln Pro Leu Ala Leu Glu Gly
1               5                   10                  15

Ser Leu Gln Lys Arg Gly Ile Val Glu Gln Cys
            20                  25
```

<210> SEQ ID NO 11
<211> LENGTH: 11
<212> TYPE: PRT
<213> ORGANISM: Homo sapiens

<400> SEQUENCE: 11

Leu Ala Leu Glu Gly Ser Leu Gln Lys Arg Gly
1               5                   10

<210> SEQ ID NO 12
<211> LENGTH: 18
<212> TYPE: PRT
<213> ORGANISM: Homo sapiens

<400> SEQUENCE: 12

Gly Ser Leu Gln Pro Leu Ala Leu Glu Gly Ser Leu Gln Lys Arg Gly
1               5                   10                  15

Ile Val

<210> SEQ ID NO 13
<211> LENGTH: 20
<212> TYPE: PRT
<213> ORGANISM: Homo sapiens

<400> SEQUENCE: 13

Gly Gly Gly Pro Gly Ala Gly Ser Leu Gln Pro Leu Ala Leu Glu Gly
1               5                   10                  15

Ser Leu Gln Lys
            20

<210> SEQ ID NO 14
<211> LENGTH: 28
<212> TYPE: PRT
<213> ORGANISM: Homo sapiens

<400> SEQUENCE: 14

Ser His Leu Val Glu Ala Leu Tyr Leu Val Cys Gly Glu Arg Gly Phe
1               5                   10                  15

Phe Tyr Thr Pro Lys Thr Arg Arg Glu Ala Glu Asp
            20                  25

<210> SEQ ID NO 15
<211> LENGTH: 17
<212> TYPE: PRT
<213> ORGANISM: Homo sapiens

<400> SEQUENCE: 15

Gln Pro Leu Ala Leu Glu Gly Ser Leu Gln Lys Arg Gly Ile Val Glu
1               5                   10                  15

Gln

<210> SEQ ID NO 16
<211> LENGTH: 65
<212> TYPE: PRT
<213> ORGANISM: Homo sapiens

<400> SEQUENCE: 16

Ala Tyr Gln Ala Glu Pro Asn Thr Cys Ala Thr Ala Gln Gly Glu Gly
1               5                   10                  15

Asn Ile Lys Lys Asn Arg His Pro Asp Phe Leu Pro Tyr Asp His Ala
            20                  25                  30

```
Arg Ile Lys Leu Lys Val Glu Ser Pro Ser Arg Ser Asp Tyr Ile
            35                  40                  45

Asn Ala Ser Pro Ile Ile Glu His Asp Pro Arg Met Pro Ala Tyr Ile
 50                  55                  60

Ala
 65

<210> SEQ ID NO 17
<211> LENGTH: 35
<212> TYPE: PRT
<213> ORGANISM: Homo sapiens

<400> SEQUENCE: 17

Gly Pro Leu Ser His Thr Ile Ala Asp Phe Trp Gln Met Val Trp Glu
 1               5                  10                  15

Ser Gly Cys Thr Val Ile Val Met Leu Thr Pro Leu Val Glu Asp Gly
            20                  25                  30

Val Lys Gln
        35

<210> SEQ ID NO 18
<211> LENGTH: 56
<212> TYPE: PRT
<213> ORGANISM: Homo sapiens

<400> SEQUENCE: 18

Gly Ala Ser Leu Tyr His Val Tyr Glu Val Asn Leu Val Ser Glu His
 1               5                  10                  15

Ile Trp Cys Glu Asp Phe Leu Val Arg Ser Phe Tyr Leu Lys Asn Val
            20                  25                  30

Gln Thr Gln Glu Thr Arg Thr Leu Thr Gln Phe His Phe Leu Ser Trp
        35                  40                  45

Pro Ala Glu Gly Thr Pro Ala Ser
 50                  55

<210> SEQ ID NO 19
<211> LENGTH: 39
<212> TYPE: PRT
<213> ORGANISM: Homo sapiens

<400> SEQUENCE: 19

Glu His Val Arg Asp Gln Arg Pro Gly Leu Val Arg Ser Lys Asp Gln
 1               5                  10                  15

Phe Glu Phe Ala Leu Thr Ala Val Ala Glu Glu Val Asn Ala Ile Leu
            20                  25                  30

Lys Ala Leu Pro Gln Cys Gly
        35

<210> SEQ ID NO 20
<211> LENGTH: 304
<212> TYPE: PRT
<213> ORGANISM: Homo sapiens

<400> SEQUENCE: 20

Met Gly Asn His Ala Gly Lys Arg Glu Leu Asn Ala Glu Lys Ala Ser
 1               5                  10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
```

```
            35                  40                  45
Ala Asp Ala Asn Gln Asn Asn Gly Thr Ser Ser Gln Asp Thr Ala Val
 50                  55                  60

Thr Asp Ser Lys Arg Thr Ala Asp Pro Lys Asn Ala Trp Gln Asp Ala
 65                  70                  75                  80

His Pro Ala Asp Pro Gly Ser Arg Pro His Leu Ile Arg Leu Phe Ser
                 85                  90                  95

Arg Asp Ala Pro Gly Arg Glu Asp Asn Thr Phe Lys Asp Arg Pro Ser
                100                 105                 110

Glu Ser Asp Glu Leu Gln Thr Ile Gln Glu Asp Ser Ala Ala Thr Ser
                115                 120                 125

Glu Ser Leu Asp Val Met Ala Ser Gln Lys Arg Pro Ser Gln Arg His
            130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
                180                 185                 190

Asp Ser His His Pro Ala Arg Thr Ala His Tyr Gly Ser Leu Pro Gln
                195                 200                 205

Lys Ser His Gly Arg Thr Gln Asp Glu Asn Pro Val Val His Phe Phe
210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
                260                 265                 270

Lys Gly Phe Lys Gly Val Asp Ala Gln Gly Thr Leu Ser Lys Ile Phe
                275                 280                 285

Lys Leu Gly Gly Arg Asp Ser Arg Ser Gly Ser Pro Met Ala Arg Arg
            290                 295                 300

<210> SEQ ID NO 21
<211> LENGTH: 247
<212> TYPE: PRT
<213> ORGANISM: Homo sapiens

<400> SEQUENCE: 21

Met Ala Ser Leu Ser Arg Pro Ser Leu Pro Ser Cys Leu Cys Ser Phe
 1               5                  10                  15

Leu Leu Leu Leu Leu Gln Val Ser Ser Ser Tyr Ala Gly Gln Phe
             20                  25                  30

Arg Val Ile Gly Pro Arg His Pro Ile Arg Ala Leu Val Gly Asp Glu
         35                  40                  45

Val Glu Leu Pro Cys Arg Ile Ser Pro Gly Lys Asn Ala Thr Gly Met
     50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
                100                 105                 110
```

```
Arg Ile Arg Asn Val Arg Phe Ser Asp Glu Gly Gly Phe Thr Cys Phe
            115                 120                 125

Phe Arg Asp His Ser Tyr Gln Glu Ala Ala Met Glu Leu Lys Val
130                 135                 140

Glu Asp Pro Phe Tyr Trp Val Ser Pro Gly Val Leu Val Leu Ala
145                 150                 155                 160

Val Leu Pro Val Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
            195                 200                 205

Ile Thr Leu Phe Val Ile Val Pro Val Leu Gly Pro Leu Val Ala Leu
210                 215                 220

Ile Ile Cys Tyr Asn Trp Leu His Arg Arg Leu Ala Gly Gln Phe Leu
225                 230                 235                 240

Glu Glu Leu Arg Asn Pro Phe
            245

<210> SEQ ID NO 22
<211> LENGTH: 277
<212> TYPE: PRT
<213> ORGANISM: Homo sapiens

<400> SEQUENCE: 22

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
                20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
        50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
210                 215                 220

Leu Ser Ile Cys Lys Thr Ala Glu Phe Gln Met Thr Phe His Leu Phe
225                 230                 235                 240
```

```
Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275

<210> SEQ ID NO 23
<211> LENGTH: 20
<212> TYPE: PRT
<213> ORGANISM: Homo sapiens

<400> SEQUENCE: 23

Lys Tyr Leu Ala Thr Ala Ser Thr Met Asp His Ala Arg His Gly Phe
1               5                   10                  15

Leu Pro Arg His
            20

<210> SEQ ID NO 24
<211> LENGTH: 16
<212> TYPE: PRT
<213> ORGANISM: Homo sapiens

<400> SEQUENCE: 24

Glu Asn Pro Trp His Phe Phe Lys Asn Ile Val Thr Pro Arg Thr Pro
1               5                   10                  15

<210> SEQ ID NO 25
<211> LENGTH: 19
<212> TYPE: PRT
<213> ORGANISM: Homo sapiens

<400> SEQUENCE: 25

Leu Ser Arg Phe Ser Trp Gly Ala Glu Gly Gln Arg Pro Gly Phe Gly
1               5                   10                  15

Tyr Gly Gly

<210> SEQ ID NO 26
<211> LENGTH: 25
<212> TYPE: PRT
<213> ORGANISM: Homo sapiens

<400> SEQUENCE: 26

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 27
<211> LENGTH: 20
<212> TYPE: PRT
<213> ORGANISM: Homo sapiens

<400> SEQUENCE: 27

Gly Gln Phe Arg Val Ile Gly Pro Arg His Pro Ile Arg Ala Leu Val
1               5                   10                  15

Gly Asp Glu Val
            20

<210> SEQ ID NO 28
<211> LENGTH: 20
```

-continued

```
<212> TYPE: PRT
<213> ORGANISM: Homo sapiens

<400> SEQUENCE: 28

Met Glu Val Gly Trp Tyr Arg Pro Pro Phe Ser Arg Trp His Leu Tyr
1               5                   10                  15

Arg Asn Gly Lys
            20

<210> SEQ ID NO 29
<211> LENGTH: 16
<212> TYPE: PRT
<213> ORGANISM: Homo sapiens

<400> SEQUENCE: 29

His Cys Leu Gly Lys Trp Leu Gly His Pro Asp Lys Phe Val Gly Ile
1               5                   10                  15

<210> SEQ ID NO 30
<211> LENGTH: 31
<212> TYPE: PRT
<213> ORGANISM: Homo sapiens

<400> SEQUENCE: 30

Lys Asn Ala Thr Gly Met Glu Val Gly Trp Tyr Arg Ser Pro Phe Ser
1               5                   10                  15

Arg Val Val His Leu Tyr Arg Asn Gly Lys Asp Gln Asp Ala Glu
            20                  25                  30

<210> SEQ ID NO 31
<211> LENGTH: 17
<212> TYPE: PRT
<213> ORGANISM: Homo sapiens

<400> SEQUENCE: 31

Glu Asn Pro Val Val His Phe Phe Lys Asn Ile Val Thr Pro Arg Thr
1               5                   10                  15

Pro

<210> SEQ ID NO 32
<211> LENGTH: 21
<212> TYPE: PRT
<213> ORGANISM: Homo sapiens

<400> SEQUENCE: 32

Met Glu Val Gly Trp Tyr Arg Pro Pro Phe Ser Arg Val Val His Leu
1               5                   10                  15

Tyr Arg Asn Gly Lys
            20

<210> SEQ ID NO 33
<211> LENGTH: 17
<212> TYPE: PRT
<213> ORGANISM: Homo sapiens

<400> SEQUENCE: 33

Asp Glu Asn Pro Val Val His Phe Phe Lys Asn Ile Val Thr Pro Arg
1               5                   10                  15

Thr

<210> SEQ ID NO 34
<211> LENGTH: 18
```

```
<212> TYPE: PRT
<213> ORGANISM: Homo sapiens

<400> SEQUENCE: 34

Asp Glu Asn Pro Val Val His Phe Phe Lys Asn Ile Val Thr Pro Arg
1               5                   10                  15

Thr Pro

<210> SEQ ID NO 35
<211> LENGTH: 25
<212> TYPE: PRT
<213> ORGANISM: Homo sapiens

<400> SEQUENCE: 35

Asp Glu Asn Pro Val Val His Phe Phe Lys Asn Ile Val Thr Pro Arg
1               5                   10                  15

Thr Pro Pro Pro Ser Gln Gly Lys Gly
            20                  25

<210> SEQ ID NO 36
<211> LENGTH: 20
<212> TYPE: PRT
<213> ORGANISM: Homo sapiens

<400> SEQUENCE: 36

Val His Phe Phe Lys Asn Ile Val Thr Pro Arg Thr Pro Pro Pro Ser
1               5                   10                  15

Gln Gly Lys Gly
            20

<210> SEQ ID NO 37
<211> LENGTH: 25
<212> TYPE: PRT
<213> ORGANISM: Homo sapiens

<400> SEQUENCE: 37

Ala Ser Asp Tyr Lys Ser Ala His Lys Gly Leu Lys Gly Val Asp Ala
1               5                   10                  15

Gln Gly Thr Leu Ser Lys Ile Phe Lys
            20                  25

<210> SEQ ID NO 38
<211> LENGTH: 18
<212> TYPE: PRT
<213> ORGANISM: Homo sapiens

<400> SEQUENCE: 38

Gly Thr Glu Lys Leu Ile Glu Thr Tyr Phe Ser Lys Asn Tyr Gln Asp
1               5                   10                  15

Tyr Glu

<210> SEQ ID NO 39
<211> LENGTH: 18
<212> TYPE: PRT
<213> ORGANISM: Homo sapiens

<400> SEQUENCE: 39

Gly Phe Tyr Thr Thr Gly Ala Val Arg Gln Ile Phe Gly Asp Tyr Lys
1               5                   10                  15

Thr Thr
```

-continued

```
<210> SEQ ID NO 40
<211> LENGTH: 22
<212> TYPE: PRT
<213> ORGANISM: Homo sapiens

<400> SEQUENCE: 40

Ala Val Arg Gln Ile Phe Gly Asp Tyr Lys Thr Thr Ile Cys Gly Lys
1               5                   10                  15

Gly Leu Ser Ala Thr Val
            20

<210> SEQ ID NO 41
<211> LENGTH: 20
<212> TYPE: PRT
<213> ORGANISM: Homo sapiens

<400> SEQUENCE: 41

Asn Thr Trp Thr Thr Cys Gln Ser Ile Ala Phe Pro Ser Lys Thr Ser
1               5                   10                  15

Ala Ser Ile Gly
            20

<210> SEQ ID NO 42
<211> LENGTH: 20
<212> TYPE: PRT
<213> ORGANISM: Homo sapiens

<400> SEQUENCE: 42

Ser Lys Thr Ser Ala Ser Ile Gly Ser Leu Cys Ala Asp Ala Arg Met
1               5                   10                  15

Tyr Gly Val Leu
            20

<210> SEQ ID NO 43
<211> LENGTH: 20
<212> TYPE: PRT
<213> ORGANISM: Homo sapiens

<400> SEQUENCE: 43

Pro Ile Arg Ala Leu Val Gly Asp Glu Val Glu Leu Pro Cys Arg Ile
1               5                   10                  15

Ser Pro Gly Lys
            20

<210> SEQ ID NO 44
<211> LENGTH: 20
<212> TYPE: PRT
<213> ORGANISM: Homo sapiens

<400> SEQUENCE: 44

Glu Leu Pro Cys Arg Ile Ser Pro Gly Lys Asn Ala Thr Gly Met Glu
1               5                   10                  15

Val Gly Trp Tyr
            20

<210> SEQ ID NO 45
<211> LENGTH: 23
<212> TYPE: PRT
<213> ORGANISM: Homo sapiens

<400> SEQUENCE: 45

Glu Tyr Arg Gly Arg Thr Glu Leu Leu Lys Asp Ala Ile Gly Glu Gly
1               5                   10                  15
```

```
Lys Val Thr Leu Arg Ile Arg
            20

<210> SEQ ID NO 46
<211> LENGTH: 62
<212> TYPE: PRT
<213> ORGANISM: Homo sapiens

<400> SEQUENCE: 46

Gly Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala
    50                  55                  60

<210> SEQ ID NO 47
<211> LENGTH: 63
<212> TYPE: PRT
<213> ORGANISM: Homo sapiens

<400> SEQUENCE: 47

Ser His Gly Arg Thr Gln Asp Glu Asn Pro Val Val His Phe Phe Lys
1               5                   10                  15

Asn Ile Val Thr Pro Arg Thr Pro Pro Ser Gln Gly Lys Gly Arg
            20                  25                  30

Gly Leu Ser Leu Ser Arg Phe Ser Trp Gly Ala Glu Gly Gln Arg Pro
        35                  40                  45

Gly Phe Gly Tyr Gly Gly Arg Ala Ser Asp Tyr Lys Ser Cys Gly
    50                  55                  60

<210> SEQ ID NO 48
<211> LENGTH: 118
<212> TYPE: PRT
<213> ORGANISM: Homo sapiens

<400> SEQUENCE: 48

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
            115

<210> SEQ ID NO 49
<211> LENGTH: 529
```

<212> TYPE: PRT
<213> ORGANISM: Homo sapiens

<400> SEQUENCE: 49

```
Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
        50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
                100                 105                 110

Thr Glu Arg Arg Leu Leu Val Arg Arg Asn Ile Phe Asp Leu Ser Ala
            115                 120                 125

Pro Glu Lys Asp Lys Phe Phe Ala Tyr Leu Thr Leu Ala Lys His Thr
        130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
                180                 185                 190

Glu Ile Trp Arg Asp Ile Asp Phe Ala His Glu Ala Pro Ala Phe Leu
            195                 200                 205

Pro Trp His Arg Leu Phe Leu Leu Arg Trp Glu Gln Glu Ile Gln Lys
        210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
                260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
        290                 295                 300

Asp Lys Ser Arg Thr Pro Arg Leu Pro Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
                340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
        370                 375                 380

Ile Phe Leu Leu His His Ala Phe Val Asp Ser Ile Phe Glu Gln Trp
385                 390                 395                 400
```

```
Leu Arg Arg His Arg Pro Leu Gln Glu Val Tyr Pro Glu Ala Asn Ala
            405                 410                 415

Pro Ile Gly His Asn Arg Glu Ser Tyr Met Val Pro Phe Ile Pro Leu
        420                 425                 430

Tyr Arg Asn Gly Asp Phe Phe Ile Ser Ser Lys Asp Leu Gly Tyr Asp
        435                 440                 445

Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
            485                 490                 495

Ser Leu Leu Cys Arg His Lys Arg Lys Gln Leu Pro Glu Glu Lys Gln
                500                 505                 510

Pro Leu Leu Met Glu Lys Glu Asp Tyr His Ser Leu Tyr Gln Ser His
            515                 520                 525

Leu

<210> SEQ ID NO 50
<211> LENGTH: 661
<212> TYPE: PRT
<213> ORGANISM: Homo sapiens

<400> SEQUENCE: 50

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240
```

```
Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
                355                 360                 365

Ala Glu Ser Thr Gly Met Thr Pro Glu Lys Val Pro Val Ser Glu Val
        370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Gly Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655
```

```
Ser Gly Gln Gln Val
            660

<210> SEQ ID NO 51
<211> LENGTH: 323
<212> TYPE: PRT
<213> ORGANISM: Homo sapiens

<400> SEQUENCE: 51

Met Ser Asp Arg Pro Thr Ala Arg Arg Trp Gly Lys Cys Gly Pro Leu
1               5                  10                  15

Cys Thr Arg Glu Asn Ile Met Val Ala Phe Lys Gly Val Trp Thr Gln
                20                  25                  30

Ala Phe Trp Lys Ala Val Thr Ala Glu Phe Leu Ala Met Leu Ile Phe
            35                  40                  45

Val Leu Leu Ser Leu Gly Ser Thr Ile Asn Trp Gly Gly Thr Glu Lys
50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
                100                 105                 110

Ala Lys Ser Val Phe Tyr Ile Ala Ala Gln Cys Leu Gly Ala Ile Ile
            115                 120                 125

Gly Ala Gly Ile Leu Tyr Leu Val Thr Pro Pro Ser Val Val Gly Gly
        130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
                180                 185                 190

Ile Gly Phe Ser Val Ala Ile Gly His Leu Phe Ala Ile Asn Tyr Thr
            195                 200                 205

Gly Ala Ser Met Asn Pro Ala Arg Ser Phe Gly Pro Ala Val Ile Met
        210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
                260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
        290                 295                 300

Asp Arg Gly Glu Glu Lys Lys Gly Lys Asp Gln Ser Gly Glu Val Leu
305                 310                 315                 320

Ser Ser Val

<210> SEQ ID NO 52
<211> LENGTH: 405
<212> TYPE: PRT
<213> ORGANISM: Homo sapiens
```

<400> SEQUENCE: 52

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
                20                  25                  30

Arg Asp Tyr Ile Asp His Val Ser Gln Val Gln Pro Val Asp Gly Val
            35                  40                  45

Val Leu Val Asp Pro Asp Leu Val Lys Gly Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
                115                 120                 125

Tyr Leu Pro Cys Ser Val Met Leu Gln Pro Ala Pro Gln Asp Ser Gly
130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405
```

-continued

```
<210> SEQ ID NO 53
<211> LENGTH: 1247
<212> TYPE: PRT
<213> ORGANISM: Homo sapiens

<400> SEQUENCE: 53
```

| | | | | | | | | | | | | | | |
|---|---|---|---|---|---|---|---|---|---|---|---|---|---|---|
| Met | Met | Arg | Glu | Trp | Val | Leu | Met | Ser | Val | Leu | Leu | Cys | Gly | Leu |
| 1 | | | | 5 | | | | | 10 | | | | | 15 |
| Ala | Gly | Pro | Thr | His | Leu | Phe | Gln | Pro | Ser | Leu | Val | Leu | Asp | Met | Ala |
| | | | 20 | | | | | 25 | | | | | 30 | | |
| Lys | Val | Leu | Leu | Asp | Asn | Tyr | Cys | Phe | Pro | Glu | Asn | Leu | Leu | Gly | Met |
| | | | 35 | | | | | 40 | | | | | 45 | | |
| Gln | Glu | Ala | Ile | Gln | Gln | Ala | Ile | Lys | Ser | His | Glu | Ile | Leu | Ser | Ile |
| | 50 | | | | | 55 | | | | | 60 | | | | |
| Ser | Asp | Pro | Gln | Thr | Leu | Ala | Ser | Val | Leu | Thr | Ala | Gly | Val | Gln | Ser |
| 65 | | | | | 70 | | | | | 75 | | | | | 80 |
| Ser | Leu | Asn | Asp | Pro | Arg | Leu | Val | Ile | Ser | Tyr | Glu | Pro | Ser | Thr | Pro |
| | | | | 85 | | | | | 90 | | | | | 95 | |
| Glu | Pro | Pro | Pro | Gln | Val | Pro | Ala | Leu | Thr | Ser | Leu | Ser | Glu | Glu | Glu |
| | | | 100 | | | | | 105 | | | | | 110 | | |
| Leu | Leu | Ala | Trp | Leu | Gln | Arg | Gly | Leu | Arg | His | Glu | Val | Leu | Glu | Gly |
| | | | 115 | | | | | 120 | | | | | 125 | | |
| Asn | Val | Gly | Tyr | Leu | Arg | Val | Asp | Ser | Val | Pro | Gly | Gln | Glu | Val | Leu |
| | | | 130 | | | | | 135 | | | | | 140 | | |
| Ser | Met | Met | Gly | Glu | Phe | Leu | Val | Ala | His | Val | Trp | Gly | Asn | Leu | Met |
| 145 | | | | | 150 | | | | | 155 | | | | | 160 |
| Gly | Thr | Ser | Ala | Leu | Val | Leu | Asp | Leu | Arg | His | Cys | Thr | Gly | Gly | Gln |
| | | | | 165 | | | | | 170 | | | | | 175 | |
| Val | Ser | Gly | Ile | Pro | Tyr | Ile | Ile | Ser | Tyr | Leu | His | Pro | Gly | Asn | Thr |
| | | | 180 | | | | | 185 | | | | | 190 | | |
| Ile | Leu | His | Val | Asp | Thr | Ile | Tyr | Asn | Arg | Pro | Ser | Asn | Thr | Thr | Thr |
| | | | 195 | | | | | 200 | | | | | 205 | | |
| Glu | Ile | Trp | Thr | Leu | Pro | Gln | Val | Leu | Gly | Glu | Arg | Tyr | Gly | Ala | Asp |
| | | 210 | | | | | 215 | | | | | 220 | | | |
| Lys | Asp | Val | Val | Leu | Thr | Ser | Ser | Gln | Thr | Arg | Gly | Val | Ala | Glu |
| 225 | | | | | 230 | | | | | 235 | | | | | 240 |
| Asp | Ile | Ala | His | Ile | Leu | Lys | Gln | Met | Arg | Arg | Ala | Ile | Val | Val | Gly |
| | | | | 245 | | | | | 250 | | | | | 255 | |
| Glu | Arg | Thr | Gly | Gly | Gly | Ala | Leu | Asp | Leu | Arg | Lys | Leu | Arg | Ile | Gly |
| | | | 260 | | | | | 265 | | | | | 270 | | |
| Glu | Ser | Asp | Phe | Phe | Phe | Thr | Val | Pro | Val | Ser | Arg | Ser | Leu | Gly | Pro |
| | | 275 | | | | | 280 | | | | | 285 | | | |
| Leu | Gly | Gly | Gly | Ser | Gln | Thr | Trp | Glu | Gly | Ser | Gly | Val | Leu | Pro | Cys |
| | 290 | | | | | 295 | | | | | 300 | | | | |
| Val | Gly | Thr | Pro | Ala | Glu | Gln | Ala | Leu | Glu | Lys | Ala | Leu | Ala | Ile | Leu |
| 305 | | | | | 310 | | | | | 315 | | | | | 320 |
| Thr | Leu | Arg | Ser | Ala | Leu | Pro | Gly | Val | Val | His | Cys | Leu | Gln | Glu | Val |
| | | | | 325 | | | | | 330 | | | | | 335 | |
| Leu | Lys | Asp | Tyr | Tyr | Thr | Leu | Val | Asp | Arg | Val | Pro | Thr | Leu | Leu | Gln |
| | | | 340 | | | | | 345 | | | | | 350 | | |
| His | Leu | Ala | Ser | Met | Asp | Phe | Ser | Thr | Val | Val | Ser | Glu | Glu | Asp | Leu |
| | | | 355 | | | | | 360 | | | | | 365 | | |
| Val | Thr | Lys | Leu | Asn | Ala | Gly | Leu | Gln | Ala | Ala | Ser | Glu | Asp | Pro | Arg |

```
            370                 375                 380
Leu Leu Val Arg Ala Ile Gly Pro Thr Glu Thr Pro Ser Trp Pro Ala
385                 390                 395                 400

Pro Asp Ala Ala Glu Asp Ser Pro Gly Val Ala Pro Glu Leu Pro
                405                 410                 415

Glu Asp Glu Ala Ile Arg Gln Ala Leu Val Asp Ser Val Phe Gln Val
                420                 425                 430

Ser Val Leu Pro Gly Asn Val Gly Tyr Leu Arg Phe Asp Ser Phe Ala
            435                 440                 445

Asp Ala Ser Val Leu Gly Val Leu Ala Pro Tyr Val Leu Arg Gln Val
450                 455                 460

Trp Glu Pro Leu Gln Asp Thr Glu His Leu Ile Met Asp Leu Arg His
465                 470                 475                 480

Asn Pro Gly Gly Pro Ser Ser Ala Val Pro Leu Leu Leu Ser Tyr Phe
                485                 490                 495

Gln Gly Pro Glu Ala Gly Pro Val His Leu Phe Thr Thr Tyr Asp Arg
                500                 505                 510

Arg Thr Asn Ile Thr Gln Glu His Phe Ser His Met Glu Leu Pro Gly
            515                 520                 525

Pro Arg Tyr Ser Thr Gln Arg Gly Val Tyr Leu Leu Thr Ser His Arg
            530                 535                 540

Thr Ala Thr Ala Ala Glu Glu Phe Ala Phe Leu Met Gln Ser Leu Gly
545                 550                 555                 560

Trp Ala Thr Leu Val Gly Glu Ile Thr Ala Gly Asn Leu Leu His Thr
                565                 570                 575

Arg Thr Val Pro Leu Leu Asp Thr Pro Glu Gly Ser Leu Ala Leu Thr
                580                 585                 590

Val Pro Val Leu Thr Phe Ile Asp Asn His Gly Glu Ala Trp Leu Gly
            595                 600                 605

Gly Gly Val Val Pro Asp Ala Ile Val Leu Ala Glu Glu Ala Leu Asp
610                 615                 620

Lys Ala Gln Glu Val Leu Glu Phe His Gln Ser Leu Gly Ala Leu Val
625                 630                 635                 640

Glu Gly Thr Gly His Leu Leu Glu Ala His Tyr Ala Arg Pro Glu Val
                645                 650                 655

Val Gly Gln Thr Ser Ala Leu Leu Arg Ala Lys Leu Ala Gln Gly Ala
                660                 665                 670

Tyr Arg Thr Ala Val Asp Leu Glu Ser Leu Ala Ser Gln Leu Thr Ala
            675                 680                 685

Asp Leu Gln Glu Val Ser Gly Asp His Arg Leu Leu Val Phe His Ser
            690                 695                 700

Pro Gly Glu Leu Val Val Glu Glu Ala Pro Pro Pro Pro Ala Val
705                 710                 715                 720

Pro Ser Pro Glu Glu Leu Thr Tyr Leu Ile Glu Ala Leu Phe Lys Thr
                725                 730                 735

Glu Val Leu Pro Gly Gln Leu Gly Tyr Leu Arg Phe Asp Ala Met Ala
                740                 745                 750

Glu Leu Glu Thr Val Lys Ala Val Gly Pro Gln Leu Val Arg Leu Val
            755                 760                 765

Trp Gln Gln Leu Val Asp Thr Ala Ala Leu Val Ile Asp Leu Arg Tyr
            770                 775                 780

Asn Pro Gly Ser Tyr Ser Thr Ala Ile Pro Leu Leu Cys Ser Tyr Phe
785                 790                 795                 800
```

Phe Glu Ala Glu Pro Arg Gln His Leu Tyr Ser Val Phe Asp Arg Ala
            805                 810                 815

Thr Ser Lys Val Thr Glu Val Trp Thr Leu Pro Gln Val Ala Gly Gln
            820                 825                 830

Arg Tyr Gly Ser His Lys Asp Leu Tyr Ile Leu Met Ser His Thr Ser
            835                 840                 845

Gly Ser Ala Ala Glu Ala Phe Ala His Thr Met Gln Asp Leu Gln Arg
            850                 855                 860

Ala Thr Val Ile Gly Glu Pro Thr Ala Gly Gly Ala Leu Ser Val Gly
865                 870                 875                 880

Ile Tyr Gln Val Gly Ser Ser Pro Leu Tyr Ala Ser Met Pro Thr Gln
            885                 890                 895

Met Ala Met Ser Ala Thr Thr Gly Lys Ala Trp Asp Leu Ala Gly Val
            900                 905                 910

Glu Pro Asp Ile Thr Val Pro Met Ser Glu Ala Leu Ser Ile Ala Gln
            915                 920                 925

Asp Ile Val Ala Leu Arg Ala Lys Val Pro Thr Val Leu Gln Thr Ala
            930                 935                 940

Gly Lys Leu Val Ala Asp Asn Tyr Ala Ser Ala Glu Leu Gly Ala Lys
945                 950                 955                 960

Met Ala Thr Lys Leu Ser Gly Leu Gln Ser Arg Tyr Ser Arg Val Thr
            965                 970                 975

Ser Glu Val Ala Leu Ala Glu Ile Leu Gly Ala Asp Leu Gln Met Leu
            980                 985                 990

Ser Gly Asp Pro His Leu Lys Ala Ala His Ile Pro Glu Asn Ala Lys
            995                 1000                1005

Asp Arg Ile Pro Gly Ile Val Pro Met Gln Ile Pro Ser Pro Glu
            1010                1015                1020

Val Phe Glu Glu Leu Ile Lys Phe Ser Phe His Thr Asn Val Leu
            1025                1030                1035

Glu Asp Asn Ile Gly Tyr Leu Arg Phe Asp Met Phe Gly Asp Gly
            1040                1045                1050

Glu Leu Leu Thr Gln Val Ser Arg Leu Leu Val Glu His Ile Trp
            1055                1060                1065

Lys Lys Ile Met His Thr Asp Ala Met Ile Ile Asp Met Arg Phe
            1070                1075                1080

Asn Ile Gly Gly Pro Thr Ser Ser Ile Pro Ile Leu Cys Ser Tyr
            1085                1090                1095

Phe Phe Asp Glu Gly Pro Pro Val Leu Leu Asp Lys Ile Tyr Ser
            1100                1105                1110

Arg Pro Asp Asp Ser Val Ser Glu Leu Trp Thr His Ala Gln Val
            1115                1120                1125

Val Gly Glu Arg Tyr Gly Ser Lys Lys Ser Met Val Ile Leu Thr
            1130                1135                1140

Ser Ser Val Thr Ala Gly Thr Ala Glu Glu Phe Thr Tyr Ile Met
            1145                1150                1155

Lys Arg Leu Gly Arg Ala Leu Val Ile Gly Glu Val Thr Ser Gly
            1160                1165                1170

Gly Cys Gln Pro Pro Gln Thr Tyr His Val Asp Asp Thr Asn Leu
            1175                1180                1185

Tyr Leu Thr Ile Pro Thr Ala Arg Ser Val Gly Ala Ser Asp Gly
            1190                1195                1200

-continued

```
Ser Ser Trp Glu Gly Val Gly Val Thr Pro His Val Val Pro
    1205                1210                1215

Ala Glu Glu Ala Leu Ala Arg Ala Lys Glu Met Leu Gln His Asn
    1220                1225                1230

Gln Leu Arg Val Lys Arg Ser Pro Gly Leu Gln Asp His Leu
    1235                1240                1245

<210> SEQ ID NO 54
<211> LENGTH: 33
<212> TYPE: PRT
<213> ORGANISM: Homo sapiens

<400> SEQUENCE: 54

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 55
<211> LENGTH: 33
<212> TYPE: PRT
<213> ORGANISM: Homo sapiens

<400> SEQUENCE: 55

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 56
<211> LENGTH: 18
<212> TYPE: PRT
<213> ORGANISM: Homo sapiens

<400> SEQUENCE: 56

Gln Gln Tyr Pro Ser Gly Gln Gly Ser Phe Gln Pro Ser Gln Gln Asn
1               5                   10                  15

Pro Gln

<210> SEQ ID NO 57
<211> LENGTH: 12
<212> TYPE: PRT
<213> ORGANISM: Homo sapiens

<400> SEQUENCE: 57

Gln Pro Phe Pro Gln Pro Glu Gln Pro Phe Pro Trp
1               5                   10

<210> SEQ ID NO 58
<211> LENGTH: 15
<212> TYPE: PRT
<213> ORGANISM: Homo sapiens

<400> SEQUENCE: 58

Glu Leu Gln Pro Phe Pro Gln Pro Glu Leu Pro Tyr Pro Gln Pro
1               5                   10                  15

<210> SEQ ID NO 59
<211> LENGTH: 18
```

```
<212> TYPE: PRT
<213> ORGANISM: Homo sapiens

<400> SEQUENCE: 59

Gly Cys Arg Gly Gly Gly Pro Gln Pro Gln Pro Phe Pro Ser Gln Gln
1               5                   10                  15
Pro Tyr

<210> SEQ ID NO 60
<211> LENGTH: 51
<212> TYPE: PRT
<213> ORGANISM: Homo sapiens

<400> SEQUENCE: 60

Gly Cys Arg Gly Gly Gly Pro Gln Pro Gln Pro Phe Pro Ser Gln Gln
1               5                   10                  15

Pro Tyr Leu Gln Leu Gln Pro Phe Pro Gln Pro Gln Leu Pro Tyr Pro
            20                  25                  30

Gln Pro Gln Leu Pro Tyr Pro Gln Pro Gln Leu Pro Tyr Pro Gln Pro
        35                  40                  45

Gln Pro Phe
    50

<210> SEQ ID NO 61
<211> LENGTH: 51
<212> TYPE: PRT
<213> ORGANISM: Homo sapiens

<400> SEQUENCE: 61

Gly Cys Arg Gly Gly Gly Pro Gln Pro Gln Pro Phe Pro Ser Gln Gln
1               5                   10                  15

Pro Tyr Leu Gln Leu Gln Pro Phe Pro Gln Pro Glu Leu Pro Tyr Pro
            20                  25                  30

Gln Pro Glu Leu Pro Tyr Pro Gln Pro Glu Leu Pro Tyr Pro Gln Pro
        35                  40                  45

Gln Pro Phe
    50

<210> SEQ ID NO 62
<211> LENGTH: 140
<212> TYPE: PRT
<213> ORGANISM: Homo sapiens

<400> SEQUENCE: 62

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110
```

| | | | | | | | | | | | | |
|---|---|---|---|---|---|---|---|---|---|---|---|---|
| Leu | Glu | Asp | Met | Pro | Val | Asp | Pro | Asp | Asn | Glu | Ala | Tyr | Glu | Met | Pro |
| | | 115 | | | | 120 | | | | 125 | | |
| Ser | Glu | Glu | Gly | Tyr | Gln | Asp | Tyr | Glu | Pro | Glu | Ala | | | | |
| | 130 | | | | 135 | | | | 140 | | | | | | |